US008133726B2

(12) United States Patent
Cai et al.

(10) Patent No.: US 8,133,726 B2
(45) Date of Patent: Mar. 13, 2012

(54) EX-VIVO PRIMING FOR GENERATING CYTOTOXIC T LYMPHOCYTES SPECIFIC FOR NON-TUMOR ANTIGENS TO TREAT AUTOIMMUNE AND ALLERGIC DISEASE

(75) Inventors: Zeling Cai, San Diego, CA (US); Michael R. Jackson, Del Mar, CA (US); Per A. Peterson, Basking Ridge, NJ (US); Wei-Xing Shi, San Diego, CA (US); Yan Kong, Belle Mead, NJ (US); Juli DeGraw, San Diego, CA (US)

(73) Assignee: Ortho-McNeil Pharmaceutical Corp., Raritan, NJ (US)

( * ) Notice: Subject to any disclaimer, the term of this patent is extended or adjusted under 35 U.S.C. 154(b) by 0 days.

(21) Appl. No.: 12/899,069

(22) Filed: Oct. 6, 2010

(65) Prior Publication Data

US 2011/0065187 A1   Mar. 17, 2011

Related U.S. Application Data

(60) Division of application No. 11/935,486, filed on Nov. 6, 2007, now Pat. No. 7,842,501, which is a continuation of application No. 11/580,358, filed on Oct. 13, 2006, now abandoned, which is a division of application No. 10/144,188, filed on May 13, 2002, now Pat. No. 7,811,816.

(60) Provisional application No. 60/291,300, filed on May 15, 2001.

(51) Int. Cl.
    C12N 5/08    (2006.01)
(52) U.S. Cl. .......................................... 435/372
(58) Field of Classification Search .................. None
    See application file for complete search history.

(56) References Cited

U.S. PATENT DOCUMENTS

| | | | |
|---|---|---|---|
| 5,614,611 | A | 3/1997 | Chang |
| 5,645,837 | A | 7/1997 | Jameson et al. |
| 5,734,023 | A | 3/1998 | Nag et al. |
| 5,827,737 | A | 10/1998 | Peterson et al. |
| 5,994,523 | A | 11/1999 | Kawakami et al. |
| 6,228,621 | B1 | 5/2001 | Williams et al. |

FOREIGN PATENT DOCUMENTS

| | | |
|---|---|---|
| EP | 0814838 | 5/2003 |
| WO | WO 9402156 | 2/1994 |
| WO | WO 0023053 | 4/2000 |
| WO | WO 0025722 | 5/2000 |

OTHER PUBLICATIONS

Aarnoudse et al. Int. J Cancer, 2002, vol. 99, pp. 7-13.
Albert et al., "Dendritic Cells Acquire Antigen from Apoptotic Cells and Induce Class I-Restricted CTLs", Nature, 1998, 392: pp. 86-89.
Alderson, M.R., et al. "Interleukin 7 Enhances Cytolytic T Lymphocyte Generation and Induces Lymphokine-activated Killer Cells from Human Peripheral Blood", 1990. J. Exp. Med. 172: pp. 577-587.
Alters et al. "Immunotherapy of Cncer: Generation of CEA Specific CTL Using CEA Peptide Pulsed Dendritic Cells", Dendritic Cells in Fundamental and Clinical Immunology, vol. 417, pp. 519-524, 1997.
Angelichio et al al, "Comparison of Several Promoters and Polyadenylation Signals for Use in Heterologous Gene Expression in Cultured Drosophilia Cells", Nucleic. Acids Research, vol. 19, No. 18, pp. 5037-5043, 1991.
Bakker, et al., "Melanocyte Lineage-Specific Antigen gp100 is Recognized by Melanoma-derived Tumor-infiltrating Lymphocytes", J. of Experimental Medicine, vol. 179, Mar. 1994, pp. 1005-1009.
Bellone et al, "In Vitro Priming of Cytotoxic T Lymphocytes against Poorly Immunogenic Epitopes by Engineered antigen-presenting Cells", Eur. J. Immunology 24: pp. 2691-2698, 1994.
Cai, et al, "Influence of Antigen Dose and Costimulation on the Primary Response of CD8+ T Cells in Vitro," J. Exp. Med. 1996, 183, pp. 2247-2257.
Cai et al "Probing the activation requirements for naïve CD8+ T cells with Drosophilia Cell Transfectants as Antigen Presenting Cells," Immunological Reviews, 1998, 165, pp. 249-265.
Cai et al., "Requirements for Peptide-Induced T Cell Receptor Down-regulation on Nïve CD8+ T Cells", J. Exp. Med, vol. 185, No. 4, Feb. 17, 1997 pp. 641-651.
Cai, et al, "Transfected Drosophila Cells as a Probe for Defining the Minimal Requirements for Stimulating Unprimed CD8+ T Cells", Proc. Natl. Acad. Sci. USA, vol. 93, pp. 14736-14741, Dec. 1996.
Chen et al., "Costimulation of T Cells for Tumor Immunity", Imm. Today vol. 14, No. 10:1993 pp. 483-485.
De Wall Malefyt et al., "CD2/LFA-3 or LFA-1/1CAM-1 but not CD28/B7 Interactions can Augment Cytotoxicity by Virus-Specific CD8+ Cytotoxic T Lymphocytes", Eur. J. Immunol. 1993, 23: pp. 418-424.
Flesch et al. "Monocyte Inflammatory Protein-1 Alpha Facilities Priming of CD8+ Cell Responses to Exogenous Viral Antigen", Int. Immunol., vol. 12, No. 9, pp. 1365-1370, 2000.
Gagliardi, et al, "Presentation of Peptides by Cultured Monocytes or Activated T Cells Allows Specific Priming of Human Cytotoxic T Lymphocytes in vitro," Int. Immunol. 1995, 7(11), pp. 1741-1752.
Godeau, F., et al, "Expression of a Mouse Class I MHC Molecule in Insect Cells Using a Baculovirus Vector", Journal of Cell Biology, 107( ): Abstract # 2092, 1988.

(Continued)

Primary Examiner — Michail Belyavskyi

(57) ABSTRACT

Cytotoxic T lymphocytes (CTLs) specific for antigenic peptides derived from IgE molecule can be generated in vitro by stimulating resting naive CD8 T cells with IgE peptides presented by artificial antigen presenting cells. The IgE specific CTLs lyse the target cells loaded with IgE peptides in vitro and inhibit antigen specific IgE response in vivo. In addition, adoptive transfer of the IgE specific CTL to an asthmatic mouse model can inhibit the development of lung inflammation and airway hypersensitivity. IgE specific CTL provides a treatment for allergic asthma and other IgE-mediated allergic diseases. Antigenic peptides identified from non-tumor self-antigens induce specific cytotoxic T lymphocyte (CTL) in vitro. The CTL induced by peptides identified from CD40L can kill activated CD4 T cells. In vitro generated CTL specific for CD40L inhibit CD4-dependent antibody responses of all isotypes in vivo. In contrast, CTL induced by antigenic peptides derived from IgE specifically inhibit IgE responses, and adoptive transfer of CD40L-specific CTL to NOD mice at early age delay the development of diabetes in NOD mice. In vitro generated CTL specific for non-tumor self-antigens expressed on activated CD4 T cells regulate immune responses in vivo.

1 Claim, 26 Drawing Sheets

OTHER PUBLICATIONS

Goldsby et al. Immunology, 5th Edition, Freeman and Company, NY 2003, pp. 9-21 and pp. 362-365.

Grewal et al. "CD40 and CD154 in Cell-Mediated Immunity", Annual Reviews in Immunology, vol. 16, 1998, pp. 111-135.

Guelly et al,"Activation Requirements of Circulating Antigen-Specific Human CD8+ Memory T Cells Probed with Insect Cell-based Artificial Antigen-Presenting Cells", Eur. J. Immunol. 2002, 32: pp. 182-192.

Ho, et al, "Adoptive Therapy with CD8+ T Cells: It May Get by with a Little Help from its Friends", J. of Clinical Investigation, Nov. 2002, vol. 110: No. 10, pp. 1415-1417.

Hortsch, et al., "Sticky Molecules in Not-So-Sticky Cells", TIBS 16, Aug. 1991, pp. 283-287.

Huang et al., "TCR-Mediated Internalization of Peptide-MHC Complexes Acquired by T Cells", Science, Oct. 29, 1999, vol. 286, pp. 952-954.

Hwang, et al., "T Cells Can Use Either T Cell Receptor or CD28 Receptors to Absorb and Internalize Cell Surface Molecules Derived from Antigen-presenting Cells", J. Exp. Med. vol. 191, No. 7, Apr. 3, 2000 pp. 1137-1148.

Jackson et al, "Empty and Peptide-Containing Conformers of Class I Major Histocompatibility Complex Molecules Expressed in Drosophila Melanogaster Cells", Proceedings of the National Academy of Sciences USA 89: pp. 12117-12121 Dec. 1992.

Kawakami, Y. et al, "Recognition of Multiple Epitopes in the Human Melanoma Antigen gp100 by Tumor-Infiltrating T Lymphocytes Associated with In Vivo Tumor Regression", The American Association of Immunologists, Jan. 1995, pp. 3961-3968.

Lanzavecchia, A., "License to Kill", Nature, vol. 393: Jun. 4, 1998 pp. 413-414.

Latouche, et al., "Induction of Human Cytotoxic T Lymphocytes by Artificial Antigen-Presenting Cells," Nature Biotech (2000) 18: pp. 405-409.

Lustgarten, J. et al., "Specific elimination of IgE Production Using T Cell Lines Expressing Chimeric T cell Receptor Genes", Eur. J. Immunol., 1995, 25, pp. 2985-2991.

Luxembourg, Alain, et al., "Biomagnetic Isolation of Antigen-Specific CD8+T Cells Usable in Immunotherapy", Nature Biotechnology, vol. 16, Mar. 1998, pp. 281-285.

Mackensen et al., "Phase I Study in Melanoma Patients of a Vaccine with Peptide-Pulsed Dendritic Cells Generated in Vitro From CD34+Hematopoletic Progenitor Cells", Int. J. Cancer: 86, pp. 385-392 (2000).

Matsumara, et al., "In Vitro Peptide Binding to Soluble Empty Class I Major Histocompatibility Complex Molecules Isolated from Transfected Drosophila Melanogaster Cells", J. of Biological Chemistry, 1992, vol. 267, No. 33, pp. 23589-23595.

Miescher, et al, "Preferential Clonogenic Deficit of CD8-Positive T-Lymphocytes Infiltrating Human Solid Tumors", Cancer Research 48, pp. 6992-6998, Dec. 15, 1988.

Mitchell, et al., Phase I Trial of Adoptive Immunotherapy with Cytolytic T Lymphocytes Immunized Against a Tyrosinase Epitope, J. Clinical Oncology, vol. 20, No. 4 (Feb. 15, 2002): pp. 1075-1086.

Monks, et al., "Three-Dimensional Segregation of Supramolecular Activation Clusters in T Cells", Nature, vol. 395, Sep. 3, 1998: pp. 82-86.

Montagna, et al., "Dendritic Cells Pulsed with Leukemia Blasts Elicit in Vitro Potent Anti-Leukemia Cytotoxic T-Cell Response in Patients given Allogeneic Bone Marrow Transplantation and in their Donors", Blood, 2000, vol. 96: 175a, Poster Abstract #753.

Montagna, et al., Ex Vivo Priming for Long-Term Maintenance of Antileukemia Human Cytotoxic T Cells suggests a General Procedure for pp. 3359-3366, 2001, v.98.

Moskophidis, et al., "Virus Persistence in Acutely Infected Immunocompetent Mice by Exhaustion of Antiviral Cytotoxic Effector T Cells", Nature, vol. 32, Apr. 22, 1993: pp. 758-761.

Mulders, et al, "Presentation of Renal Tumor Antigens by Human Dendritic Cells Activates Tumor-infiltrating Lymphocytes against Autologous Tumor: Implications for Live Kidney Cancer Vaccines", Clinical Cancer Research, vol. 5, pp. 445-454, Feb. 1999.

Richards et al., "Therapeutic and Immunologic Evaluation of Autologous CTL Generated Using Transgenic Drosophila Cells as APC's for the Treatment of Melanoma", American Society of Clinical Oncology, Poster Display 1015, presented May 2001, vol. 20, Part 1 of 2, p. 254a.

Riddell et al., "Principles for Adoptive T Cell Therapy of Human Viral Diseases", Annu. Rev. Immunol. 1995, 13: pp. 545-586.

Riddell et al. "Therapeutic reconstitution of Human Viral Immunity by Adoptive Transfer of Cytotoxic T Lymphocyte Clones", Current Topics in Microbiol. and Immuol., vol. 189, 1994 pp. 9-34.

Rosenberg, S.A. et al, "Use of Tumor-Infiltrating Lymphocytes and Interleukin-2 in the Immunotherapy of Patients with Metastatic Melanoma", N. Eng. J. Med. 1988 319: pp. 1676-1680.

Schultze J.L. et al, Autologous tumor infiltrating Tcells cytotoxic for follicular lymphoma cells can be expanded in vitro. Blood May 1997, vol. 89, No. 10 pp. 3806-3816.

Sprent et al. "Constructing Artificial Antigen-Presenting Cells from Drosophila Cells", Advances in Experimental Medicine and Biology, vol. 417, pp. 249-254 (1997).

Sun et al., "Dual Function of Drosophila Cells as APCs for Naïve CD8+ T Cells: Implications for Tumor Immunotherapy", Immunity, vol. 4, pp. 555-564, Jun. 1996.

Sykulev Y. et al., "High-Affinity Reactions between Antigen-specific T-Cell Receptors and Peptides Associated with Allogeneic and Syngeneic Major Histocompatibiliy Complex Class I Proteins", Proc. Natl. Acad. Sci., vol. 91, pp. 11487-11491, Nov. 1994.

Udaka, K. et al, "Self-MHC Restricted Peptides Recognized by an Alloreactive T Lymphocyte Clone", J. of Immunology, 1996, 157: pp. 670-678.

Weber, S., et al, "Specific Low-Affinity Recognition of Major Histocompatibility Complex Plus Peptide by Soluble T-Cell Receptor", Nature, vol. 356, Apr. 30, 1992, pp. 793-796.

Wentworth et al. "In vitro Induction of Primary, Antigen-Specific CTL from Human Peripheral Blood Monocuclear Cells Simulated with Synthetic Peptides", Mol. Immunol., vol. 32, No. 9, pp. 603-612, 1995.

Whiteside, T. L, et al, "Generation and characterization of ex vivo propagated autologous CD8+Cells Used for Adoptive Immunotherapy of patients infected with human immunodeficiency virus", Blood, vol. 81, No. 8 (Apr. 15, 1993): pp. 2085-2092.

Yang, Y. et al, "Major Histocompatibility Complex (MHC)-encoded HAM2 Is Necessary for Antigenic Peptide Loading onto Class I MHC Molecules," The Journal of Biological Chemistry, Jun. 15, 1992, 267(17), pp. 11669-11672.

Yee et al., "Isolation of High Avidity Melanoma-Reactive CTL from Heterogeneous Populations Using Peptide-MHC Tetramers," The Journal of Immunology (1999) 162: pp. 2227-2234.

Yee C et al, Melanocyte Destruction after Antigen-specific Immunotherapy of Melanoma, Journal of Experimental Medicine 192(11):pp. 1637-1643, 2000.

Yee, et al., "Prospects for Adoptive T Cell Therapy", Current Opinion in Immunology 1997, 9: pp. 702-708.

Figure 1

```
                  1                                                    50
IgE-a-MM-C   (1) -------------------------------------- TVTWYSDSLNMSTVNFP
IgE-b-MM-C   (1) SIRNPQLYPLKPCKGTASMTLGCLVKDYFPNPVTVTWYSDSLNMSTVNFP 51                                                   100
IgE-a-MM-C  (18) ALGSELKVTTSQVTSWGKSAKNFTCHVTHPPSFNESRTILVRPVN-ITEP
IgE-b-MM-C  (51) ALGSELKVTTSQVTSWGKSAKNFTCHVTHPPSFNESRTILVRPVTHSLSP 101                                                   150
IgE-a-MM-C  (67) TLELLHSSCDPNAFHSTIQLYCFIYGHILNDVSVSWLMDDREITDTLAQT
IgE-b-MM-C (101) PWSYSIHRCDPNAFHSTIQLYCFIYGHILNDVSVSWLMDDREITDTLAQT 151                                                   200
IgE-a-MM-C (117) VLIKEEGKLASTCSKLNITEQQWMSESTFTCKVTSQGVDYLAHTRRCPDH
IgE-b-MM-C (151) VLIKEEGKLASTCSKLNITEQQWMSESTFTCRVTSQGVDYLAHTRRCPDH 201                                                   250
IgE-a-MM-C (167) EPRGVITYLIPPSPLDLYQNGAPKLTCLVVDLESEKNVNVTWNQEKKTSV
IgE-b-MM-C (201) EPRGAITYLIPPSPLDLYQNGAPKLTCLVVDLESEKNVNVTWNQEKKTSV 251                                                   300
IgE-a-MM-C (217) SASQWYTKHHNNATTSITSILPVVAKDWIEGYGYQCIVDHPDFPKPIVRS
IgE-b-MM-C (251) SASQWYTKHHNNATTSITSILPVVAKDWIEGYGYQCVVDRPDFPKPIVRS 301                                                   350
IgE-a-MM-C (267) ITKTPG-QRSAPEVYVFPPPEEESEDKRTLTCLIQNFFPEDISVQWLGDG
IgE-b-MM-C (301) ITLPQVSQRSAPEVYVFPPPEEESEDKRTLTCLIQNFFPEDISVQWLGDG 351                                                   400
IgE-a-MM-C (316) KLISNSQHSTTTPLKSNGSNQGFFIFSRLEVAKTLWTQRKQFTCQVIHEA
IgE-b-MM-C (351) KLISNSQHSTTTPLKSNGSNQGFFIFSRLEVAKTLWTQRKQFTCQVIHEA 401           423
IgE-a-MM-C (366) LQKPRKLEKTISTSLGNTSLRPS
IgE-b-MM-C (401) LQKPRKLEKTISTSLGNTSLRPS
```

Anti-OgE CTL (dose/mouse)

Anti-OgE CTL (dose/mouse)

Figure 5
Panel A
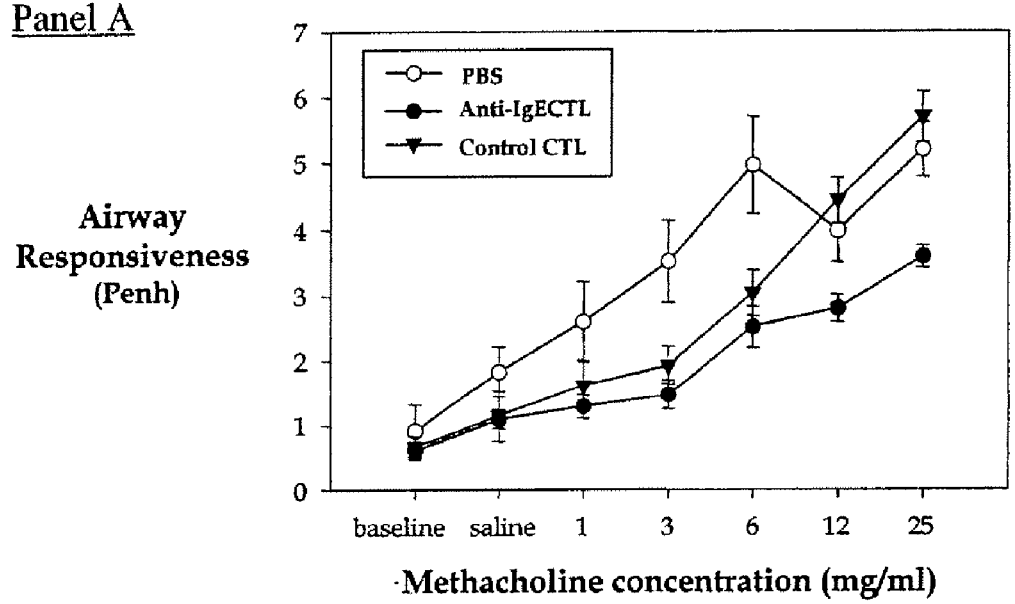
Panel B
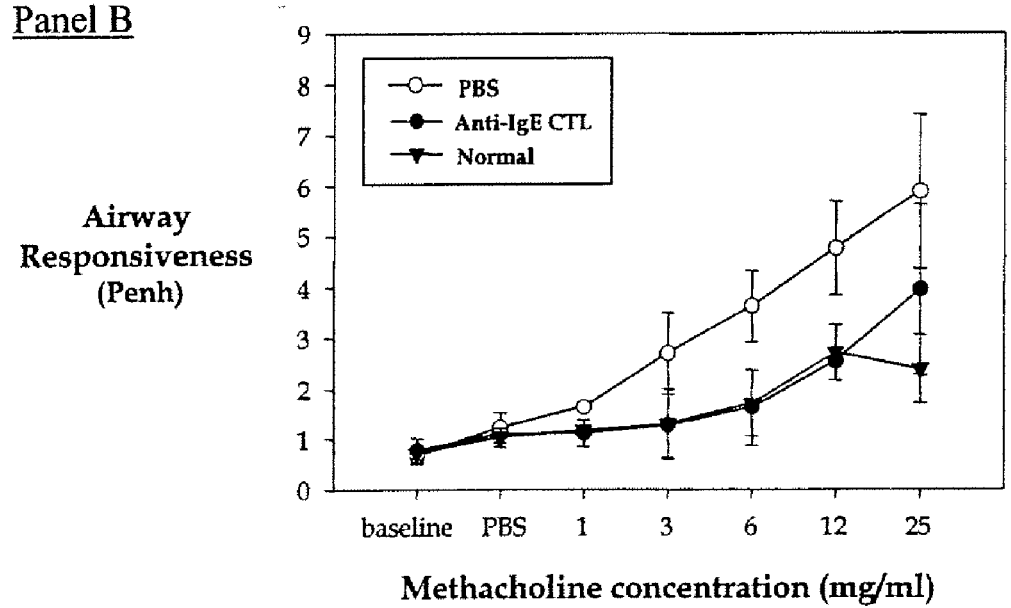

Figure 6
Panel A
No CTL
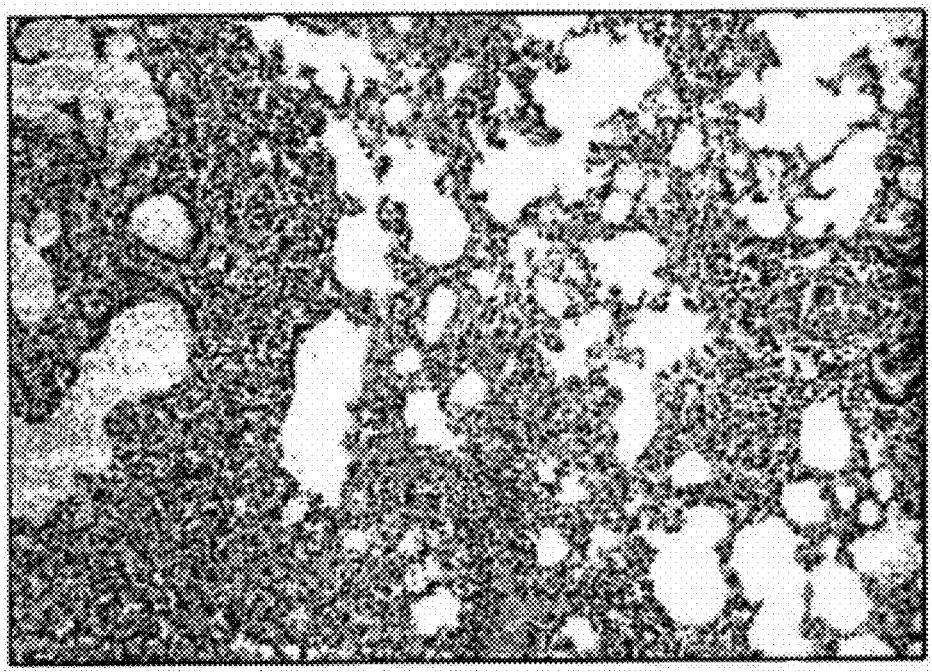
Panel B
Anti-IgE CTL
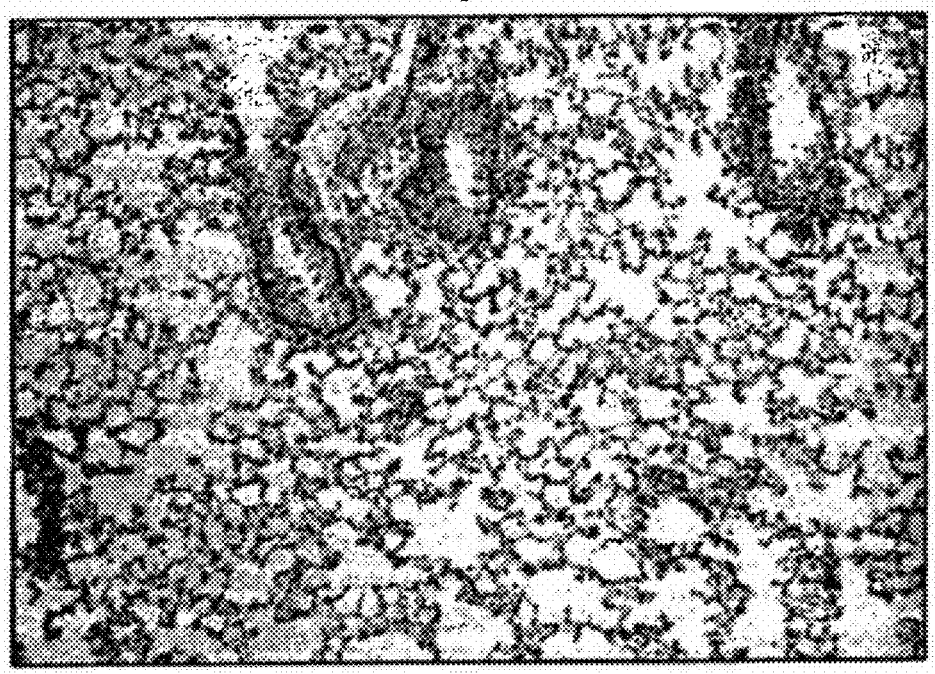

Figure 7

Human IgE Constant Region Sequence
(length = 428 residues)

```
1    ASTQSPSVFP  LTRCCKNIPS  NATSVTLGCL  ATGYFPEPVM  VTWDTGSLNG
51   TTMTLPATTL  TLSGHYATIS  LLTVSGAWAK  QMFTCRVAHT  PSSTDWVDNK
101  TFSVCSRDFT  PPTVKILQSS  CDGGGHFPPT  IQLLCLVSGY  TPGTINITWL
151  EDGQVMDVDL  STASTTQEGE  LASTQSELTL  SQKHWLSDRT  YTCQVTYQGH
201  TFEDSTKKCA  DSNPRGVSAY  LSRPSPFDLF  IRKSPTITCL  VVDLAPSKGT
251  VNLTWSRASG  KPVNHSTRKE  EKQRNGTLTV  TSTLPVGTRD  WIEGETYQCR
301  VTHPHLPRAL  MRSTTKTSGP  RAAPEVYAFA  TPEWPGSRDK  RTLACLIQNF
351  MPEDISVQWL  HNEVQLPDAR  HSTTQPRKTK  GSGFFVFSRL  EVTRAEWEQK
401  DEFICRAVHE  AASPSQTVQR  AVSVNPGK
```

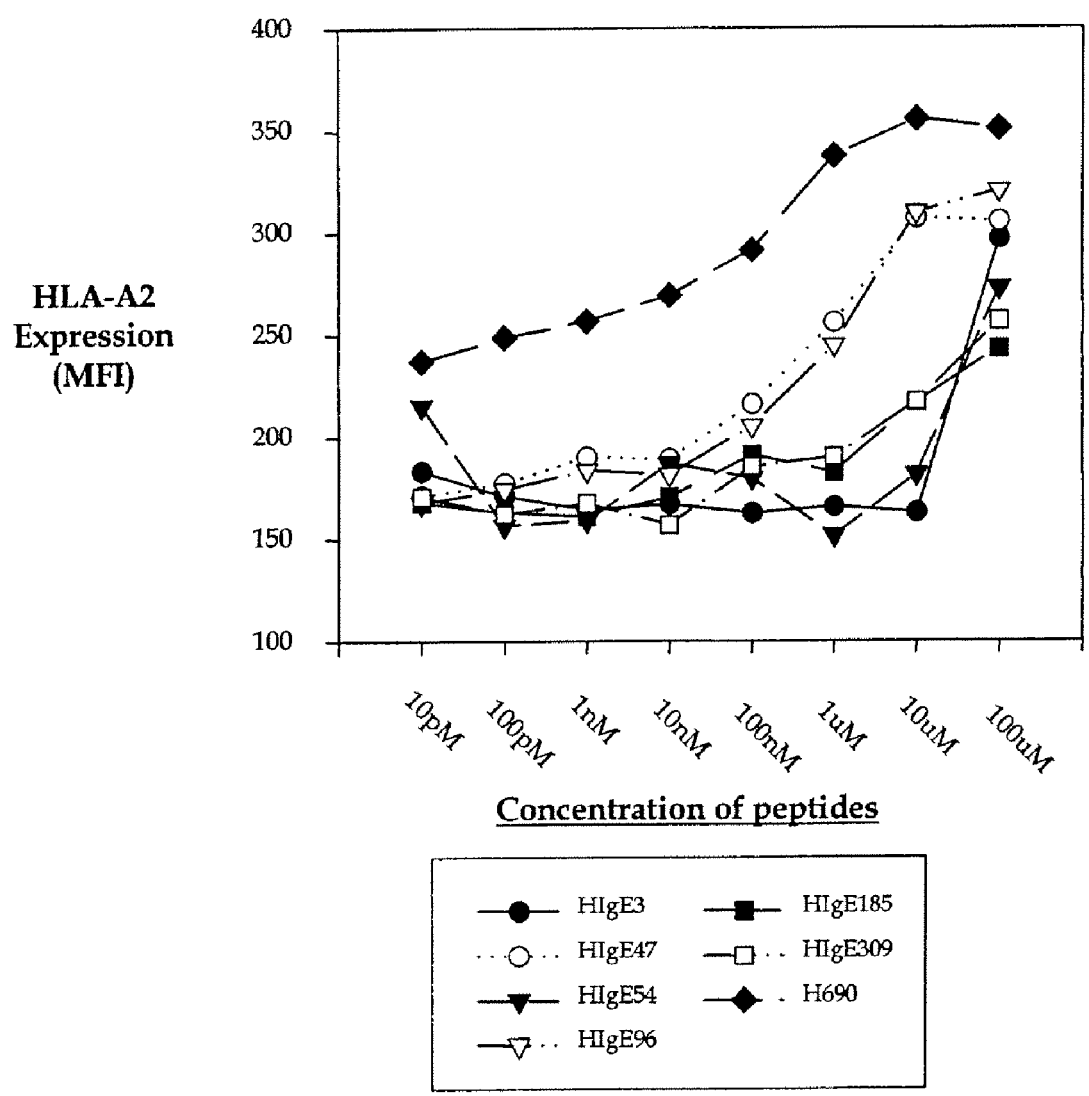

Figure 9
Panel A
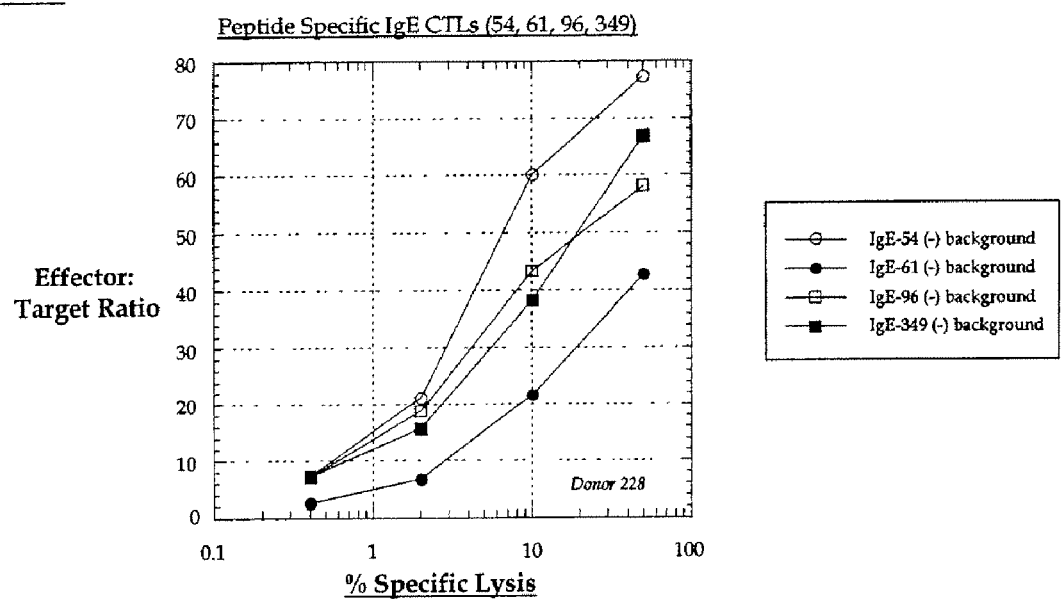
Panel B
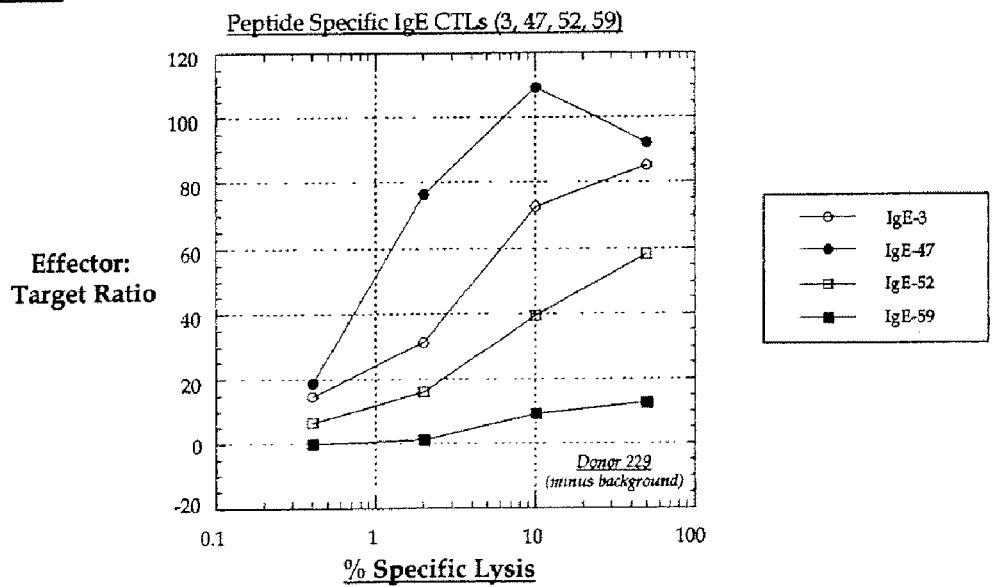

Figure 9
Panel C
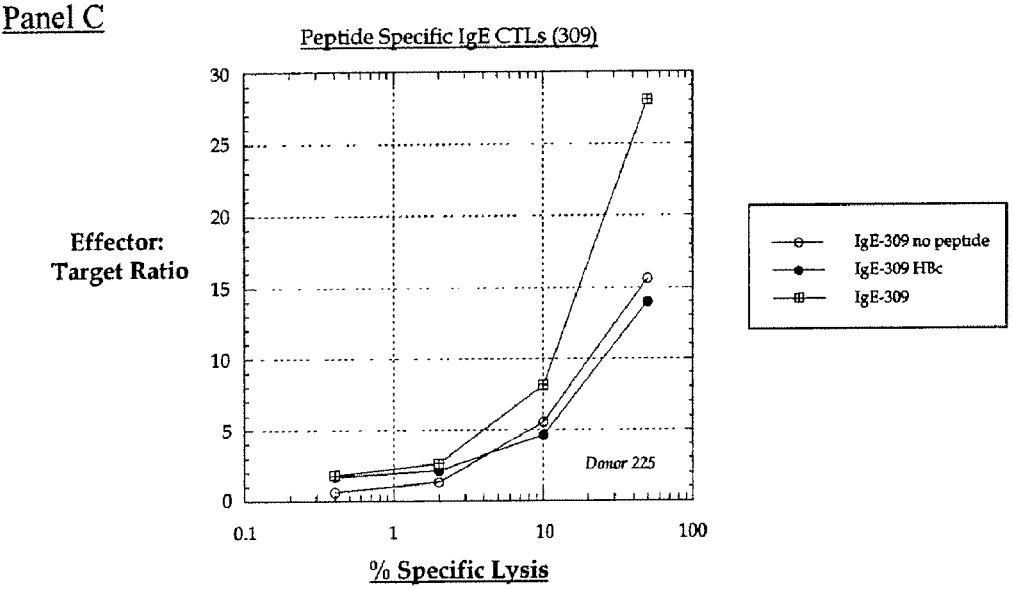
Panel D
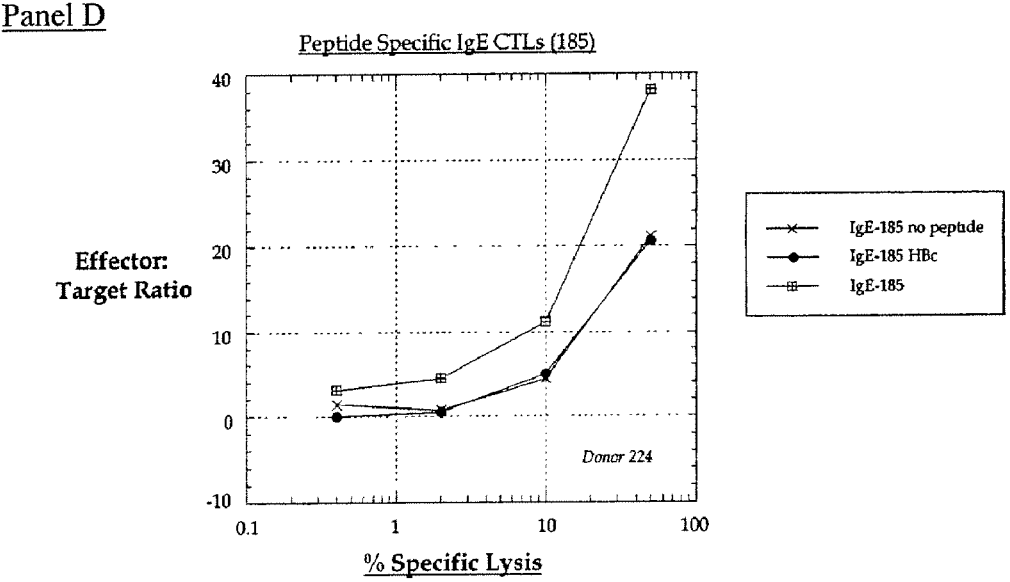

Figure 10
IgE Constant Region

AST<u>QSPSVFPL</u>TRCCK<u>NIPSNATS</u>VTLGCLATGYFPEPVMVTWDTGS<u>LNG</u>
TTMTLPATTLTLSGHYATISLLTVSGAWAKQMFTCRVAHTPSSTD<u>WVD</u>
<u>NKTFSV</u>CSRDFTPPTVKILQSSCDGGGHFPPTIQLLCLVSGYTPGTINITW
LEDGQVMDV<u>DLST</u>ASTTQEGELASTQSE<u>LTLSQKHWLSDRTYT</u>CQVTY
QHTFEDSTKKCADSNPRGVSAYLSRPSPFDLFIRKSPTITCLVVDLAPSKG
TVNLTWSRASGKPVNHSTRKEEKQRNG**TLTVTSTLPVGTRDWISTLPV
GTRDWIEGETYQCRVTHPHLPR**A<u>LMRSTTKTS</u>GPRAAPEVYAFATPEWP
GSRDKRTLACLIQNFMPEDISVQWLHNEVQP<u>DARHSTT</u>QPRKTKGSGFF
VFSRLEVTRAEWEQKDEFICRAVHEAASPSQTQRAVSVNPGK

| underline | 9mers |
|---|---|
| bold | 10mers |

Panel A

Figure 14
Panel B
CD40L.PE          Fas L.PE
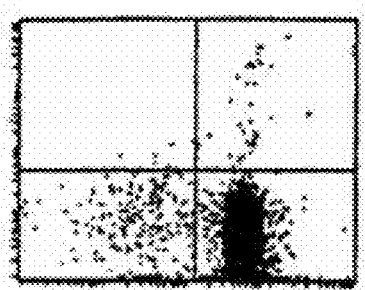 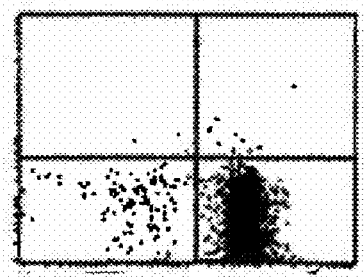
CD4.FITC
0 hours
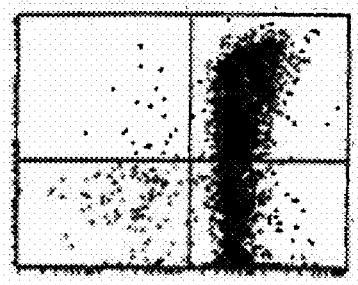 
CD4.FITC
16 hours
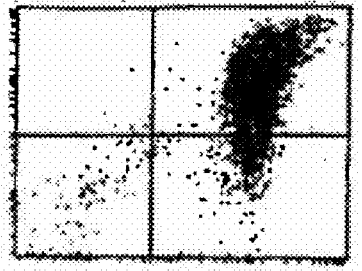 
CD4.FITC
40 hours
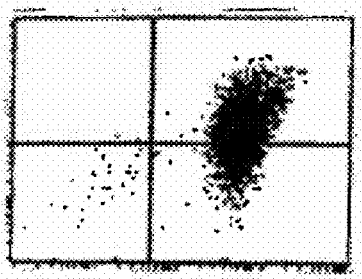 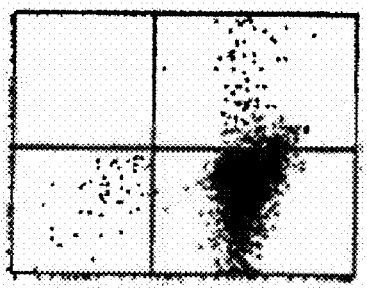
CD4.FITC
64 hours Figure 16
Panel A
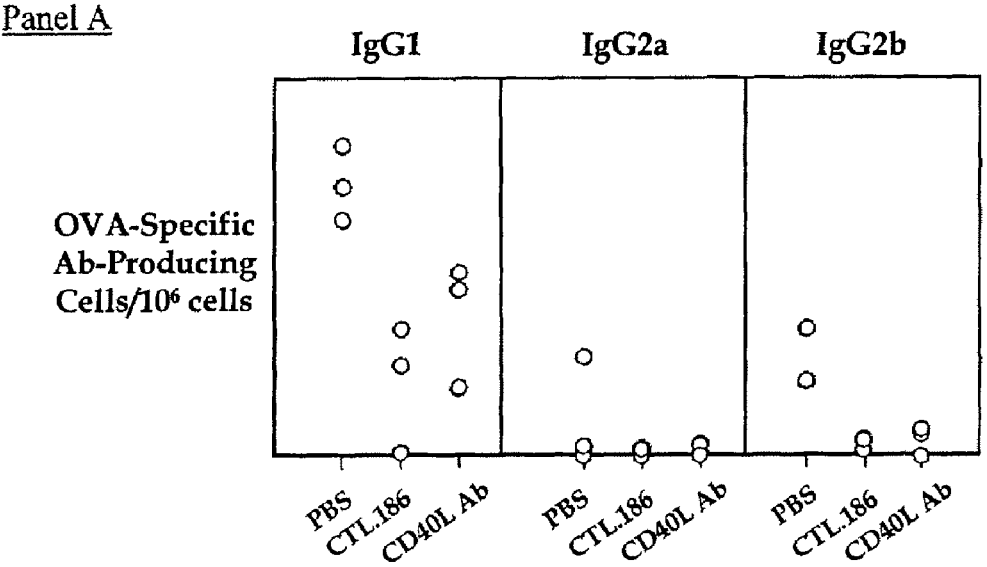
Panel B
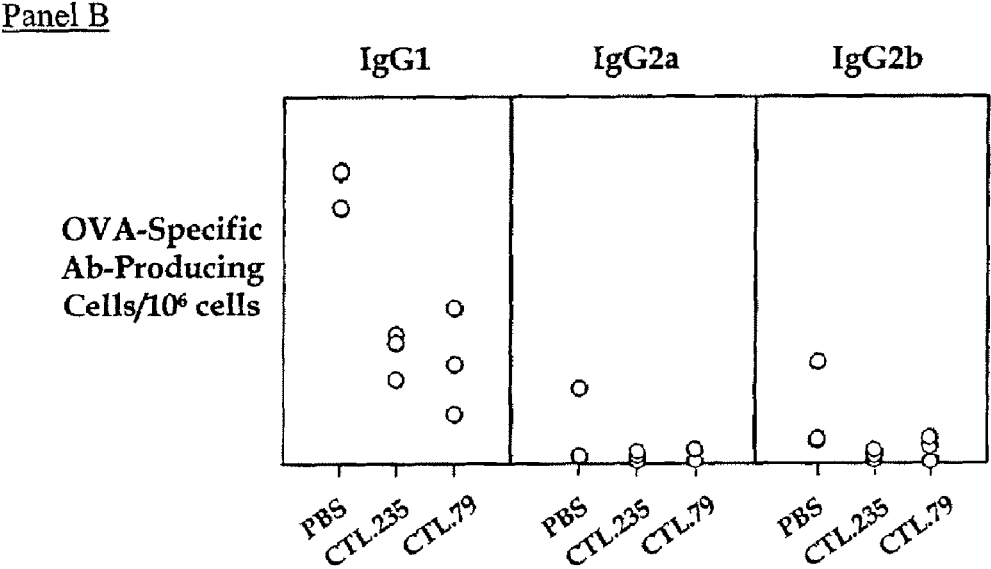

Figure 17
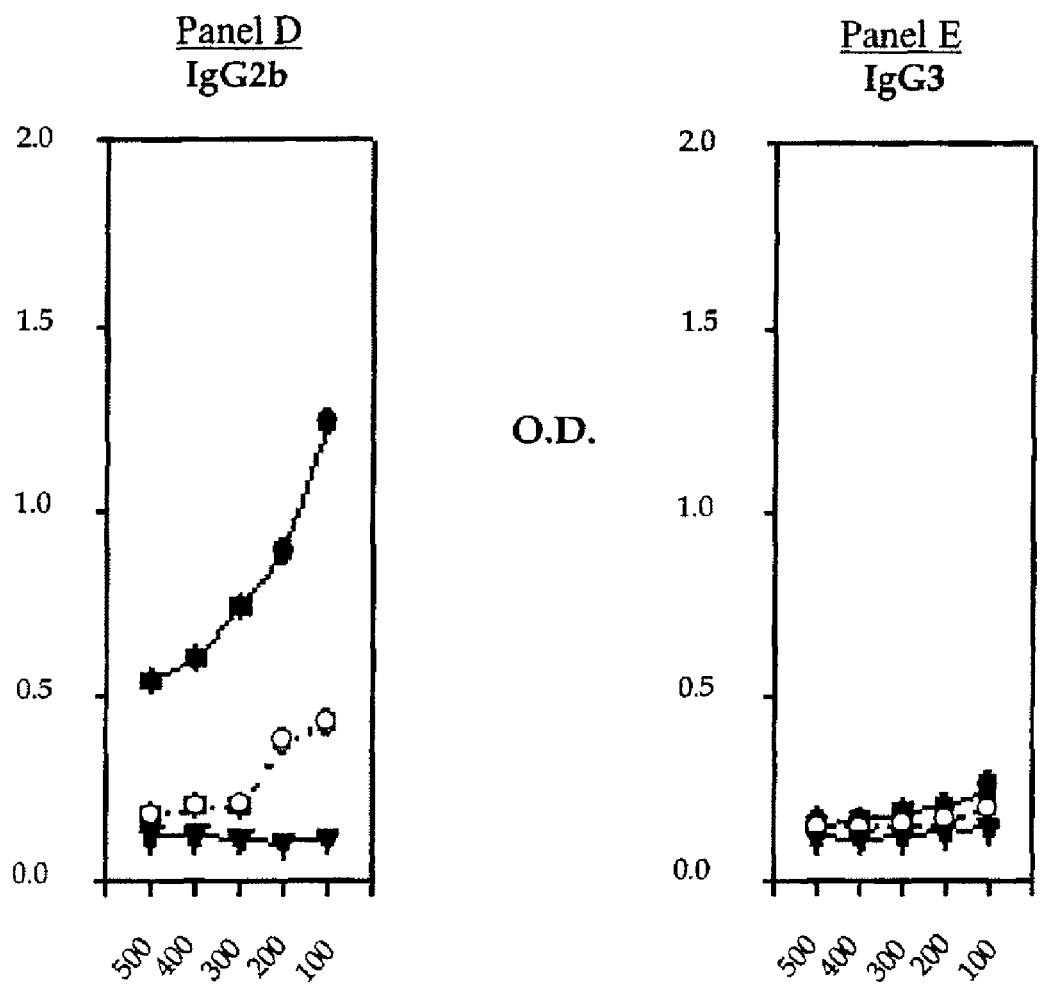
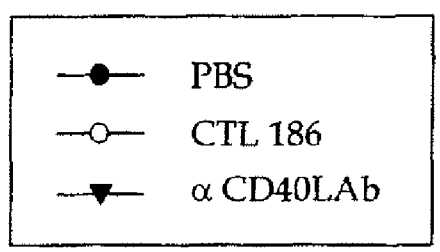

Panel C

Anti-IgE44 CTL

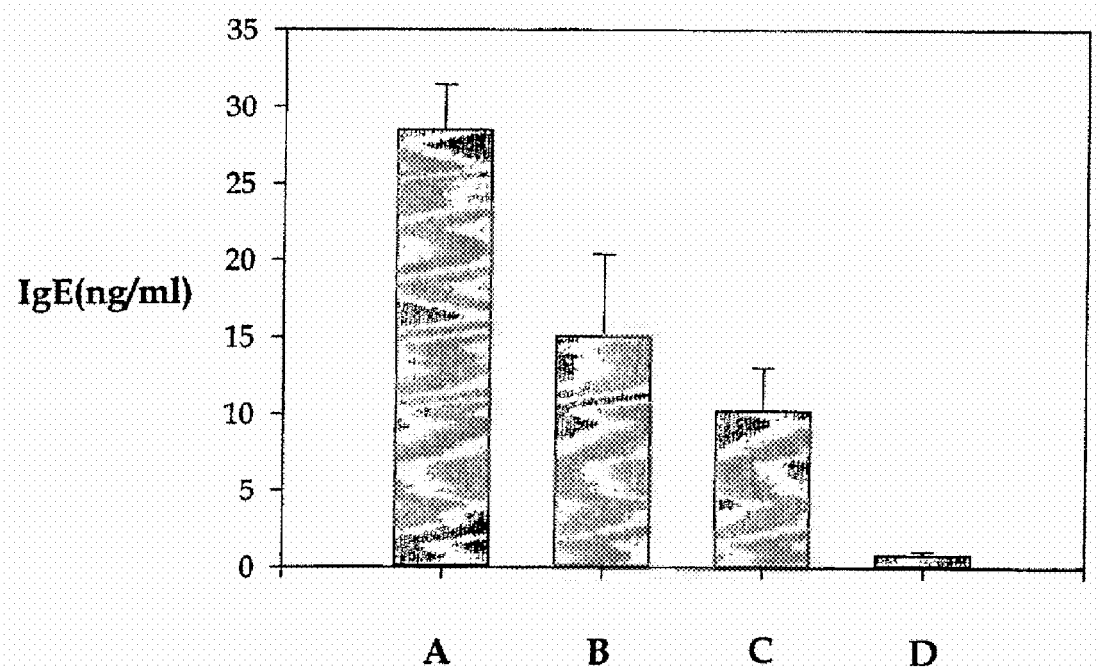

SEQUENCE LISTING

```
<160> NUMBER OF SEQ ID NOS: 105

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Pro Cys Lys Gly Thr Ala Ser Met
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Pro Pro Ser Pro Leu Asp Leu Tyr
1               5

<210> SEQ ID NO 3
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Gly Ser Asn Gln Gly Phe Phe Ile Phe
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Pro Asn Pro Val Thr Val Thr Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ser Ser Cys Asp Pro Asn Ala Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Ser Thr Ile Gln Leu Tyr Cys Phe
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ser Asn Gly Ser Asn Gln Gly Phe
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Ala Pro Glu Val Tyr Val Phe
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Ser Thr Val Asn Phe Pro Ala Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Leu Gly Asn Thr Ser Leu Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ala Ser Met Thr Leu Gly Cys Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ser Thr Cys Ser Lys Leu Asn Ile
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly His Ile Leu Asn Asp Val Ser Val
1               5

<210> SEQ ID NO 14
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Ser Ile Arg Asn Pro Gln Leu Tyr Pro Leu Lys Pro Cys Lys Gly Thr
1               5                   10                  15

Ala Ser Met Thr Leu Gly Cys Leu Val Lys Asp Tyr Glu Pro Asn Pro
            20                  25                  30

Val Thr Val Thr Trp Tyr Ser Asp Ser Leu Asn Met Ser Thr Val Asn
            35                  40                  45

Phe Pro Ala Leu Gly Ser Glu Leu Lys Val Thr Thr Ser Gln Val Thr
50                      55                  60

Ser Trp Gly Lys Ser Ala Lys Asn Phe Thr Cys His Val Thr His Pro
65                      70                  75                  80

Pro Ser Phe Asn Glu Ser Arg Thr Ile Leu Val Arg Pro Val Asn Ile
                85                  90                  95

Thr Glu Pro Thr Leu Glu Leu Leu His Ser Ser Cys Asp Pro Asn Ala
                100                 105                 110

Phe His Ser Thr Ile Gln Leu Tyr Cys Phe Ile Tyr Gly His Ile Leu
            115                 120                 125

Asn Asp Val Ser Val Ser Trp Leu Met Asp Asp Arg Glu Ile Thr Asp
        130                 135                 140

Thr Leu Ala Gln Thr Val Leu Ile Lys Glu Glu Gly Lys Leu Ala Ser
145                 150                 155                 160

Thr Cys Ser Lys Leu Asn Ile Thr Glu Gln Gln Trp Met Ser Glu Ser
                165                 170                 175

Thr Phe Thr Cys Lys Val Thr Ser Gln Gly Val Asp Tyr Leu Ala His
            180                 185                 190

Thr Arg Arg Cys Pro Asp His Glu Pro Arg Gly Val Ile Thr Tyr Leu
        195                 200                 205

Ile Pro Pro Ser Pro Leu Asp Leu Tyr Gln Asn Gly Ala Pro Lys Leu
        210                 215                 220

Thr Cys Leu Val Val Asp Leu Glu Ser Glu Lys Asn Val Asn Val Thr
225                 230                 235                 240

Trp Asn Gln Glu Lys Lys Thr Ser Val Ser Ala Ser Gln Trp Tyr Thr
                245                 250                 255

Lys His His Asn Asn Ala Thr Thr Ser Ile Thr Ser Ile Leu Pro Val
            260                 265                 270

Val Ala Lys Asp Trp Ile Glu Gly Tyr Gly Tyr Gln Cys Ile Val Asp
        275                 280                 285

His Pro Asp Phe Pro Lys Pro Ile Val Arg Ser Ile Thr Lys Thr Pro
    290                 295                 300

Gly Gln Arg Ser Ala Pro Glu Val Tyr Val Phe Pro Pro Pro Glu Glu
305                 310                 315                 320

Glu Ser Glu Asp Lys Arg Thr Leu Thr Cys Leu Ile Gln Asn Phe Phe
                325                 330                 335

Pro Glu Asp Ile Ser Val Gln Trp Leu Gly Asp Gly Lys Leu Ile Ser
            340                 345                 350

Asn Ser Gln His Ser Thr Thr Thr Pro Leu Lys Ser Asn Gly Ser Asn
        355                 360                 365

Gln Gly Phe Phe Ile Phe Ser Arg Leu Glu Val Ala Lys Thr Leu Trp
        370                 375                 380

Thr Gln Arg Lys Gln Phe Thr Cys Gln Val Ile His Glu Ala Leu Gln
385                 390                 395                 400

Lys Pro Arg Lys Leu Glu Lys Thr Ile Ser Thr Ser Leu Gly Asn Thr
                405                 410                 415

Ser Leu Pro Arg Ser
```

```
                                 420
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Pro Ala Ser Met Lys Ile Phe Met
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Pro Phe Ile Val Gly Leu Trp Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Pro Gln Ile Ala Ala His Val Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Val His Leu Gly Gly Val Phe
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Pro Arg Ser Val Ala Thr Gly Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 20

Lys Pro Ser Ile Gly Ser Glu Arg Ile
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Ser Ser Phe Gly Leu Leu Lys Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Pro Ser Pro Arg Ser Val Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Pro Ser Ser Gln Arg Pro Phe Ile
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Ser Leu Leu Asn Cys Glu Glu Met
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Met Leu Glu Asn Gly Lys Gln Leu
1               5

<210> SEQ ID NO 26
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 26

Thr Met Lys Ser Asn Leu Val Met Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Val Phe Val Asn Val Thr Glu Ala
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ser Val Leu Phe Ala Val Tyr Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ser Met Lys Ile Phe Met Tyr Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Met Tyr Leu Leu Thr Val Phe Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Leu Tyr Tyr Ile Tyr Ala Gln Val
1               5
```

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Ile Phe Met Tyr Leu Leu Thr Val
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ile Gly Ser Ala Leu Phe Ala Val
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Leu His Glu Asp Phe Val Phe Met
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Ile Tyr Ala Gln Val Thr Phe Cys
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Leu Leu Thr Val Phe Leu Ile Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Leu Gln Pro Gly Ala Ser Val Phe Val
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Leu His Arg Arg Leu Asp Lys Ile
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Met Ser Asn Asn Leu Val Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Glu Leu Gln Pro Gly Ala Ser Val
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Leu Thr Val Lys Arg Gln Gly Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Met Ile Gly Ser Ala Leu Phe Ala
1               5

<210> SEQ ID NO 43
<211> LENGTH: 9
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 43

Ser Gln Ala Pro Phe Ile Ala Ser Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Met Lys Ile Phe Met Tyr Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Thr Leu Glu Asn Gly Lys Gln Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Ile Ser Glu Ala Ser Ser Lys Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Val Phe Glu Leu Gln Pro Gly Ala
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Met Lys Ile Phe Met Tyr Leu Leu
1               5

<210> SEQ ID NO 49
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Gln Gly Leu Tyr Tyr Ile Tyr Ala
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Leu Asn Gly Thr Thr Met Thr Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Val Asp Asn Lys Thr Phe Ser Val
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Leu Ser Asp Arg Thr Tyr Thr Cys
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Leu Ser Asp Arg Thr Tyr Thr Cys
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Leu Leu Thr Val Ser Gly Ala Trp Ala
```

-continued

```
<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Leu Glu Asp Gly Gln Val Met Asp Val
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Leu Thr Val Thr Ser Thr Leu Pro Val
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Met Phe Thr Cys Arg Val Ala His Thr
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Ala Thr Ile Ser Leu Leu Thr Val
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Leu Ala Cys Leu Ile Gln Asn Phe Met
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Gln Val Met Asp Val Asp Leu Ser Thr Ala
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Glu Gly Leu Asp Thr Gln Arg Phe Ser Gly
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Leu Thr Val Ser Gly Ala Trp Ala
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Leu Pro Asp Ala Arg His Ser Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Gln Ser Pro Ser Val Phe Pro Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Leu Met Arg Ser Thr Thr Lys Thr
1               5

<210> SEQ ID NO 66
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 66

Thr Leu Thr Leu Ser Gly His Tyr Ala
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Leu Pro Ala Thr Thr Leu Thr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Leu Ser Gly His Tyr Ala Thr Ile
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Met Thr Leu Pro Ala Thr Thr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Thr Leu Ser Gln Lys His Trp Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Val Met Asp Val Asp Leu Ser Thr
1               5
```

```
<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Ile Pro Ser Asn Ala Thr Ser Val
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Leu Cys Leu Val Ser Gly Tyr Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Ile Cys Arg Ala Val His Glu Ala
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Ile Thr Cys Leu Val Val Asp Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Val Gln Trp Leu His Asn Glu Val
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

Val Met Asp Val Asp Leu Ser Thr Ala
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Pro Ser Pro Phe Asp Leu Phe Ile
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asn Phe Met Pro Glu Asp Ile Ser Val
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Trp Leu His Asn Glu Val Gln Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Tyr Phe Pro Glu Pro Val Met Val
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Leu Pro Ala Thr Thr Leu Thr
1               5

<210> SEQ ID NO 83
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 83

Asp Phe Thr Pro Pro Thr Val Lys Ile
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Phe Ile Arg Lys Ser Pro Thr Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Trp Leu Glu Asp Gly Gln Val Met
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Trp Glu Gln Lys Asp Glu Phe Ile
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Thr Val Thr Ser Thr Leu Pro Val
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Pro Pro Thr Ile Gln Leu Leu Cys Leu
1               5

<210> SEQ ID NO 89
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Leu Ala Ser Thr Gln Ser Glu Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Arg Asp Phe Thr Pro Pro Thr Val
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asn Pro Arg Gly Val Ser Ala Tyr Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Leu Thr Arg Cys Cys Lys Asn Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Thr Trp Leu Glu Asp Gly Gln Val
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Pro Thr Ile Thr Cys Leu Val Val
```

```
<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Phe Val Phe Ser Arg Leu Glu Val
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Tyr Thr Pro Gly Thr Ile Asn Ile
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly His Phe Pro Pro Thr Ile
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Pro Ser Lys Gly Thr Val Asn Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr His Pro His Leu Pro Arg Ala Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 100

Leu Pro Val Gly Thr Arg Asp Trp Ile
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Thr Lys Gly Ser Gly Phe Phe Val
1               5

<210> SEQ ID NO 102
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Thr Val Thr Trp Tyr Ser Asp Ser Leu Asn Met Ser Thr Val Asn Phe
1               5                   10                  15

Pro Ala Leu Gly Ser Glu Leu Lys Val Thr Thr Ser Gln Val Thr Ser
            20                  25                  30

Trp Gly Lys Ser Ala Lys Asn Phe Thr Cys His Val Thr His Pro Pro
        35                  40                  45

Ser Phe Asn Glu Ser Arg Thr Ile Leu Val Arg Pro Val Asn Ile Thr
    50                  55                  60

Glu Pro Thr Leu Glu Leu Leu His Ser Ser Cys Asp Pro Asn Ala Phe
65                  70                  75                  80

His Ser Thr Ile Gln Leu Tyr Cys Phe Ile Tyr Gly His Ile Leu Asn
                85                  90                  95

Asp Val Ser Val Ser Trp Leu Met Asp Asp Arg Glu Ile Thr Asp Thr
            100                 105                 110

Leu Ala Gln Thr Val Leu Ile Lys Glu Glu Gly Lys Leu Ala Ser Thr
        115                 120                 125

Cys Ser Lys Leu Asn Ile Thr Glu Gln Gln Trp Met Ser Glu Ser Thr
    130                 135                 140

Phe Thr Cys Lys Val Thr Ser Gln Gly Val Asp Tyr Leu Ala His Thr
145                 150                 155                 160

Arg Arg Cys Pro Asp His Glu Pro Arg Gly Val Ile Thr Tyr Leu Ile
                165                 170                 175

Pro Pro Ser Pro Leu Asp Leu Tyr Gln Asn Gly Ala Pro Lys Leu Thr
            180                 185                 190

Cys Leu Val Val Asp Leu Glu Ser Glu Lys Asn Val Asn Val Thr Trp
        195                 200                 205

Asn Gln Glu Lys Lys Thr Ser Val Ser Ala Ser Gln Trp Tyr Thr Lys
    210                 215                 220

His His Asn Asn Ala Thr Thr Ser Ile Thr Ser Ile Leu Pro Val Val
225                 230                 235                 240

Ala Lys Asp Trp Ile Glu Gly Tyr Gly Tyr Gln Cys Ile Val Asp His
                245                 250                 255

Pro Asp Phe Pro Lys Pro Ile Val Arg Ser Ile Thr Lys Thr Pro Gly

```
                     260                 265                 270
Gln Arg Ser Ala Pro Glu Val Tyr Val Phe Pro Pro Glu Glu Glu
            275                 280                 285

Ser Glu Asp Lys Arg Thr Leu Thr Cys Leu Ile Gln Asn Phe Phe Pro
290                 295                 300

Glu Asp Ile Ser Val Gln Trp Leu Gly Asp Gly Lys Leu Ile Ser Asn
305                 310                 315                 320

Ser Gln His Ser Thr Thr Thr Pro Leu Lys Ser Asn Gly Ser Asn Gln
                325                 330                 335

Gly Phe Phe Ile Phe Ser Arg Leu Glu Val Ala Lys Thr Leu Trp Thr
                340                 345                 350

Gln Arg Lys Gln Phe Thr Cys Gln Val Ile His Glu Ala Leu Gln Lys
            355                 360                 365

Pro Arg Lys Leu Glu Lys Thr Ile Ser Thr Ser Leu Gly Asn Thr Ser
370                 375                 380

Leu Arg Pro Ser
385

<210> SEQ ID NO 103
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ser Ile Arg Asn Pro Gln Leu Tyr Pro Leu Lys Pro Cys Lys Gly Thr
1               5                   10                  15

Ala Ser Met Thr Leu Gly Cys Leu Val Lys Asp Tyr Phe Pro Asn Pro
            20                  25                  30

Val Thr Val Thr Trp Tyr Ser Asp Ser Leu Asn Met Ser Thr Val Asn
        35                  40                  45

Phe Pro Ala Leu Gly Ser Glu Leu Lys Val Thr Thr Ser Gln Val Thr
    50                  55                  60

Ser Trp Gly Lys Ser Ala Lys Asn Phe Thr Cys His Val Thr His Pro
65                  70                  75                  80

Pro Ser Phe Asn Glu Ser Arg Thr Ile Leu Val Arg Pro Val Thr His
                85                  90                  95

Ser Leu Ser Pro Pro Trp Ser Tyr Ser Ile His Arg Cys Asp Pro Asn
            100                 105                 110

Ala Phe His Ser Thr Ile Gln Leu Tyr Cys Phe Ile Tyr Gly His Ile
        115                 120                 125

Leu Asn Asp Val Ser Val Ser Trp Leu Met Asp Asp Arg Glu Ile Thr
    130                 135                 140

Asp Thr Leu Ala Gln Thr Val Leu Ile Lys Glu Glu Gly Lys Leu Ala
145                 150                 155                 160

Ser Thr Cys Ser Lys Leu Asn Ile Thr Glu Gln Gln Trp Met Ser Glu
                165                 170                 175

Ser Thr Phe Thr Cys Arg Val Thr Ser Gln Gly Val Asp Tyr Leu Ala
            180                 185                 190

His Thr Arg Arg Cys Pro Asp His Glu Pro Arg Gly Ala Ile Thr Tyr
        195                 200                 205

Leu Ile Pro Pro Ser Pro Leu Asp Leu Tyr Gln Asn Gly Ala Pro Lys
    210                 215                 220

Leu Thr Cys Leu Val Val Asp Leu Glu Ser Glu Lys Asn Val Asn Val
```

```
                    225                 230                 235                 240

Thr Trp Asn Gln Glu Lys Lys Thr Ser Val Ser Ala Ser Gln Trp Tyr
                245                 250                 255

Thr Lys His His Asn Asn Ala Thr Thr Ser Ile Thr Ser Ile Leu Pro
                260                 265                 270

Val Val Ala Lys Asp Trp Ile Glu Gly Tyr Gly Tyr Gln Cys Val Val
                275                 280                 285

Asp Arg Pro Asp Phe Pro Lys Pro Ile Val Arg Ser Ile Thr Leu Pro
                290                 295                 300

Gln Val Ser Gln Arg Ser Ala Pro Glu Val Tyr Val Phe Pro Pro Pro
305                 310                 315                 320

Glu Glu Glu Ser Glu Asp Lys Arg Thr Leu Thr Cys Leu Ile Gln Asn
                325                 330                 335

Phe Phe Pro Glu Asp Ile Ser Val Gln Trp Leu Gly Asp Gly Lys Leu
                340                 345                 350

Ile Ser Asn Ser Gln His Ser Thr Thr Thr Pro Leu Lys Ser Asn Gly
                355                 360                 365

Ser Asn Gln Gly Phe Phe Ile Phe Ser Arg Leu Glu Val Ala Lys Thr
                370                 375                 380

Leu Trp Thr Gln Arg Lys Gln Phe Thr Cys Gln Val Ile His Glu Ala
385                 390                 395                 400

Leu Gln Lys Pro Arg Lys Leu Glu Lys Thr Ile Ser Thr Ser Leu Gly
                405                 410                 415

Asn Thr Ser Leu Arg Pro Ser
                420

<210> SEQ ID NO 104
<211> LENGTH: 428
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ser Thr Gln Ser Pro Ser Val Phe Pro Leu Thr Arg Cys Cys Lys
1               5                  10                   15

Asn Ile Pro Ser Asn Ala Thr Ser Val Thr Leu Gly Cys Leu Ala Thr
                20                 25                   30

Gly Tyr Phe Pro Glu Pro Val Met Val Thr Trp Asp Thr Gly Ser Leu
            35                 40                  45

Asn Gly Thr Thr Met Thr Leu Pro Ala Thr Thr Leu Thr Leu Ser Gly
50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
                100                 105                 110

Thr Val Lys Ile Leu Gln Ser Ser Cys Asp Gly Gly His Phe Pro
                115                 120                 125

Pro Thr Ile Gln Leu Leu Cys Leu Val Ser Gly Tyr Thr Pro Gly Thr
            130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
```

```
                165                 170                 175
Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
            195                 200                 205

Cys Ala Asp Ser Asn Pro Arg Gly Val Ser Ala Tyr Leu Ser Arg Pro
            210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
            245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
            290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
            325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
            370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ser Pro Ser Gln
            405                 410                 415

Thr Val Gln Arg Ala Val Ser Val Asn Pro Gly Lys
            420                 425

<210> SEQ ID NO 105
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
            35                  40                  45

Asn Gly Thr Thr Met Thr Leu Pro Ala Thr Thr Leu Thr Leu Ser Gly
        50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
            85                  90                  95

Val Asp Asn Lys Thr Phe Ser Val Cys Ser Arg Asp Phe Thr Pro Pro
```

```
                100             105             110
Thr Val Lys Ile Leu Gln Ser Ser Cys Asp Gly Gly Gly His Phe Pro
            115                 120                 125
Pro Thr Ile Gln Leu Leu Cys Leu Val Ser Gly Tyr Thr Pro Gly Thr
            130                 135                 140
Ile Asn Ile Thr Trp Leu Glu Asp Gly Gln Val Met Asp Val Asp Leu
145                 150                 155                 160
Ser Thr Ala Ser Thr Thr Gln Glu Gly Glu Leu Ala Ser Thr Gln Ser
                165                 170                 175
Glu Leu Thr Leu Ser Gln Lys His Trp Leu Ser Asp Arg Thr Tyr Thr
            180                 185                 190
Cys Gln Val Thr Tyr Gln His Thr Phe Glu Asp Ser Thr Lys Lys Cys
            195                 200                 205
Ala Asp Ser Asn Pro Arg Gly Val Ser Ala Tyr Leu Ser Arg Pro Ser
            210                 215                 220
Pro Phe Asp Leu Phe Ile Arg Lys Ser Pro Thr Ile Thr Cys Leu Val
225                 230                 235                 240
Val Asp Leu Ala Pro Ser Lys Gly Thr Val Asn Leu Thr Trp Ser Arg
            245                 250                 255
Ala Ser Gly Lys Pro Val Asn His Ser Thr Arg Lys Glu Glu Lys Gln
            260                 265                 270
Arg Asn Gly Thr Leu Thr Val Thr Ser Thr Leu Pro Val Gly Thr Arg
            275                 280                 285
Asp Trp Ile Ser Thr Leu Pro Val Gly Thr Arg Asp Trp Ile Glu Gly
            290                 295                 300
Glu Thr Tyr Gln Cys Arg Val Thr His Pro His Leu Pro Arg Ala Leu
305                 310                 315                 320
Met Arg Ser Thr Thr Lys Thr Ser Gly Pro Arg Ala Ala Pro Glu Val
            325                 330                 335
Tyr Ala Phe Ala Thr Pro Glu Trp Pro Gly Ser Arg Asp Lys Arg Thr
            340                 345                 350
Leu Ala Cys Leu Ile Gln Asn Phe Met Pro Glu Asp Ile Ser Val Gln
            355                 360                 365
Trp Leu His Asn Glu Val Gln Pro Asp Ala Arg His Ser Thr Thr Gln
    370                 375                 380
Pro Arg Lys Thr Lys Gly Ser Gly Phe Phe Val Phe Ser Arg Leu Glu
385                 390                 395                 400
Val Thr Arg Ala Glu Trp Glu Gln Lys Asp Glu Phe Ile Cys Arg Ala
            405                 410                 415
Val His Glu Ala Ala Ser Pro Ser Gln Thr Gln Arg Ala Val Ser Val
            420                 425                 430
Asn Pro Gly Lys
            435
```

EX-VIVO PRIMING FOR GENERATING CYTOTOXIC T LYMPHOCYTES SPECIFIC FOR NON-TUMOR ANTIGENS TO TREAT AUTOIMMUNE AND ALLERGIC DISEASE

CROSS REFERENCE TO RELATED APPLICATIONS

This application is a divisional application of U.S. application Ser. No. 11/935,486 filed Nov. 6, 2007 now U.S. Pat. No. 7,842,501, which is a continuation of U.S. application Ser. No. 11/580,358 filed Oct. 13, 2006 now abandoned which is a divisional of U.S. application Ser. No. 10/144,188 filed May 13, 2002 now U.S. Pat. No. 7,811,816, which claims priority to U.S. Provisional application Ser. No. 60/291,300 filed May 15, 2001, the entire disclosures of which are hereby incorporated in their entirety.

BACKGROUND OF THE INVENTION

Immune responses to foreign antigens such as those found in bacteria and virus protect from and eliminate infections. However, aberrant immune responses can cause allergic diseases and autoimmune diseases. Immune responses to foreign, sometimes innocuous, substances such as pollen, dust mites, food antigens and bee sting can result in allergic diseases such as hay fever, asthma and systemic anaphylaxis. Immune responses to self-antigens such as pancreatic islet antigens and cartilage antigens can lead to diabetes and arthritis, respectively. The hallmark of the allergic diseases is activation of CD4 T cells and high production of IgE by B cells, whereas the salient feature of autoimmune diseases are activation of CD4 T cells and over production of inflammation cytokines. The current therapies have been focused on the treatment of symptoms of allergy and autoimmune diseases and do not prevent the development and progression of the diseases.

CTLs are derived from resting naïve CD8 T cells and recognize antigenic peptides presented by Major Histocompatibility Complex (MHC) class I molecules. When resting CD8 T cells encounter antigenic peptides/MHC complex presented by professional antigen presenting cells, CD8 T cells will be activated and differentiated into armed CTL. Upon recognition of peptide/MHC complexes on the target cells, the antigen specific CTL will deliver a lethal hit and lysis the antigen-expressing target cells, such as virus infected target cells or tumor cells.

Activation of naive T cells in vivo is controlled by multiple receptor-ligand interactions between T cells and professional APC such as dendritic cells (R. M. Steinman, *Annu. Rev. Immunol.* (1991) 9:271-296). It is generally accepted that two signals are required for activation of naive T cells (C. A. Janeway and K. Bottomly, *Cell* (1994) 76:275-285). Signal 1 is induced by the interaction between TCR and MHC/peptide complexes (R. N. Germain, *Cell* (1994) 76:287-299) and is aided by binding of CD4/CD8 co-receptors to non-polymorphic regions of MHC class II/I molecules, respectively (M. C. Miceli and J. R. Parnes, *Adv. Immunol.* (1993) 53:59-122). Signal 2 is qualitatively different from Signal 1 and is delivered via T cell costimulatory molecules interacting with complementary ligands on APC, e.g. through CD28 interaction with B7 (P. S. Linsley and J. A. Ledbetter, *Annu. Rev. Immunol.* (1993) 11:191-212; Lenschow et al., *Annu. Rev. Immunol.* (1996) 14:233-258). Signals 1 and 2 function synergistically and trigger a series of signaling events which ultimately induce T cells to proliferate, produce cytokines and differentiate into effector cells (Mueller et al., *Annu. Rev. Immunol.* (1989) 7:445-480; A. Weiss and D. R. Littman, *Cell* (1994) 76:263-274). The relationship between Signals 1 and 2, however, is unclear.

Although a variety of molecules have been reported to have costimulatory function, particular attention has been focused on costimulation delivered via CD28-B7 interaction (R. H. Schwartz, *Cell* (1992) 71:1065-1068). CD28 is a molecule with a single Ig like domain and is constitutively expressed as a homodimer on T cells (P. S. Linsley and J. A. Ledbetter, (1993) supra). Through its interaction with either B7-1 or B7-2 molecules on APCs, CD28 molecules are thought to transduce unique signals that stimulate T cell to produce growth-promoting cytokines such as IL-2 (June et al., *Immunol. Today* (1994) 15:321-331), to upregulate expression of survival factors such as Bcl-$X_L$ (Boise et al., *Immunity* (1995) 3:87-98) and to prevent anergy induced by Signal 1 alone (R. H. Schwartz, *Curr. Opin. Immunol.* (1997) 9:351-357).

Another pair of molecules that has an important role in T cell activation is LFA-1/ICAM-1 (Van Seventer et al., *J. Immunol*, (1990) 144:4579-4586). ICAM-1 belongs to the Ig gene superfamily and has five Ig C like domains in the extracellular regions; it is expressed on both hemapoietic and nonhemapoietic cells. The receptor for ICAM-1 on T cells is LFA-1 (CD11/CD18), which belongs to the b2 integrin family (T. A. Springer, *Cell* (1994) 76:301-314). The interaction of LFA-1 with ICAM-1 has potent costimulatory function on T cells (Shimizu et al., *Immunol. Rev.* (1990) 114:109-143), although opinions vary on whether this function reflects a separate signaling pathways or increased adhesion between T cells and APC (Damle et al., *J. Immunol.* (1993) 151:2368-2379; Bachmann et al., *Immunity* (1997) 7:549-557).

In addition to B7 and ICAM-1 molecules, several other molecules on APCs, including CD70 (Hintzen et al., *J. Immunol.* (1995) 154:2612-2623) and heat-stable antigen (HSA) (Liu et al., *J. Exp. Med.* (1992) 175:437-445), can exert quite potent costimulatory function through their interaction with their respective ligands on T cells. The implication is that T-APC interaction is highly complex and involves multiple interactions between complementary sets of molecules on T cells and APCs. The interaction of each set of molecules could trigger specific signals which induce different cellular events. The combination of the different signals may act synergistically for optimal T cell activation and determine the final fate of T cells. Alternatively, the function of costimulation molecules may be redundant and the signals induced by each set of costimulation molecules are additive. The requirement for each set of costimulation molecules will be influenced by the strength and characteristics of Signal 1.

In considering these two possibilities, it is important to understand the minimal requirements for stimulating naive T cells. Studies with $CD28^{-/-}$ mice indicated that CD28-B7 interaction is highly important in some situations, but not in others (Shahinian et al., *Science* (1993) 261:609-612). Likewise, the requirement for LFA-1/ICAM interaction in primary responses is not an invariable finding (Shier et al., *J. Immunol.* (1996) 157:5375-5386).

CD8 T cells recognize antigenic peptides derived mainly from virus proteins and proteins expressed on tumor cells. However, it has recently been reported that newly synthesized proteins are preferentially processed by antigen-processing machinery (Schubert et al., *Nature*, (2000) 404:770-774). Upon activation, immune cells have acquired the ability to synthesize a number of new proteins, it is possible that IgE producing B cells and activated CD4 T cells would present a different sets of peptide/MHC complexes than the non-IgE producing cells and resting CD4 T cells. These peptides/MHC complexes presented on IgE producing B cells and activated CD4 T cells would be able to be recognized by CD8 T cells. Thus, CTL specific for these peptides/MHC complexes would be able to treat allergy and autoimmune diseases. However, a number of tolerance mechanisms have been able to prevent the activation the CD8 T cells towards self-antigens in vivo.

CD8 lymphocytes (CTLs) are the arm of adaptive immunity responsible for the recognition and elimination of infected cells, tumor cells, and allogeneic cells. Once primed, CTL can recognize their target antigen on a wide variety of cells and accomplish their function by lysing the target cell and/or secreting cytokines like TNF-alpha, or IFN-gamma.

Presentation of antigen to $CD8^+$ CTL (cytotoxic T lymphocytes) occurs in the context of MHC class I molecules (MHC-I), while presentation of antigen to $CD4^+$ HTL (helper T lymphocytes) occurs in the context of MHC class II molecules.

Efficient induction of $CD4^+$ T cell requires that the T cells interact with antigen presenting cells (APC) i.e. cells that express MHC class II and co-stimulatory molecules. APC are dendritic cells, macrophages and activated B cells. Although nearly all nucleated cells express MHC-I, naive CTL also require presentation of antigen (Ag) by bone marrow-derived APC for efficient priming (Dalyot-Herman et al., *J. Immunol.*, 165(12):6731-6737). Dendritic cells are highly potent inducers of CTL responses (J. Bancherean and R. M. Steinman, *Nature*, (1998) 392:245-252) and are thought to be the principal APC involved in priming CTL. Once primed, CTL can recognize their cognate Ags on a wide variety of cells and respond by lysing the target cell and/or secreting cytokines.

Although bone marrow-derived APC are required to efficiently prime CTL responses (P. J. Fink and M. J. Bevan, *Exp. Med.* (1978) 148:755-766) activated CTL are readily able to recognize and respond to Ag presented by a wide variety of cells. Induction of tumor- or viral-specific CTL immune responses in vivo have been shown to be dependent on bone marrow derived antigen-presenting cells (Paglia et al., *J. Exp. Med.* (1996) 183(1):317-322; Labeur et al., *J. Immunol.* (1999) 162(1):168-175). It is generally accepted that bone marrow derived APC, through mechanisms unique to these cells, take up cellular antigens either in the form of soluble antigen, associated with chaperone molecules or by phagocytosis.

It has long been demonstrated that responses to cellular antigens are dependent on help delivered by $CD4^+$ T cells. It has also been shown that the cellular antigen had to be presented on the same APC for recognition by the CTL and the HTL. The nature of this help has been interpreted as a need of IL-2 necessary for CTL expansion. Recent studies have shown that this help results from the activation of dendritic cells by HTL and is mediated via CD40-CD40L interaction (S. R. Clarke, *J. Leukocyte Bio.* (2000) 67(5):607-614).

A likely scenario for the induction of a CD8 mediated immune response to a cellular antigen (derived from a tumor cell or an infected cell) is therefore the following: dendritic cells acquire antigens derived from tumor or infected cells. Interaction of DC-antigen with CD4 cells enable the DC to activate the CD8 cells.

SUMMARY OF THE INVENTION

Immune cells, such as IgE producing B cells and activated CD4 T cells play a central role in the pathogenesis of allergic diseases and autoimmune diseases. The present invention utilizes cytotoxic T lymphocytes (CTLs) to eliminate or inhibit the immune cells that cause the allergy and/or autoimmune diseases. Thus, the development and progression of diseases can be prevented or interrupted by the methods of the present invention.

The present invention provides a method for producing CTL specific for one or more non-tumor self antigen T cell epitopes, comprising:
  a. isolating $CD8^+$ T cells from a subject;
  b. loading antigen presenting cells (APC's) having Class I MHC molecules with the T cell epitopes;
  c. culturing the $CD8^+$ T cells with the antigen-loaded APC's for a period of time sufficient for activation of precursor $CD8^+$ T cells specific for the T cell epitopes;
  d. expanding in culture the activated $CD8^+$ T cells in the presence of components required for proliferation of the activated $CD8^+$ T cells; and,
  e. collecting $CD8^+$ T cells from the culture.

The present invention also provides $CD8^+$ T cells that are specifically cytotoxic for a disease causing target cell, wherein the target cell has on its surface one or more non-tumor self antigen T cell epitopes associated with Class I MHC molecules, and wherein the $CD8^+$ T cells have been selectively activated by interaction with Class I MHC molecules associated with the non-tumor self antigen T cell epitopes.

The present invention also provides a method for treating a disease mediated by a disease causing target cell, wherein the target cell has on its surface one or more non-tumor self antigen T cell epitopes associated with Class I MHC molecules, comprising administering to a patient in need of such treatment, activated $CD8^+$ T cells wherein the $CD8^+$ T cells have been selectively activated by interaction with Class I MHC molecules associated with the non-tumor self antigen T cell epitopes.

The present invention demonstrates that by making and using artificial antigen presenting cells, tolerance of CD8 T cells to self antigens was broken and CTLs specific for antigenic peptides identified from IgE or CD40L proteins were generated. Adoptive transfer of the in vitro generated CTLs specific for CD40L to NOD mice dramatically delayed the development of diabetes, and CTLs specific for IgE peptides inhibited the production of IgE and reduced lung inflammation in an asthmatic mouse model. The above system is potentially applicable to human diseases that are caused by CD4 T cells and by IgE producing B cells. Autoimmune diseases that caused by CD4 T cells are diabetes, rheumatoid arthritis, SLE, multiple sclerosis and psoriasis. Whereas allergic diseases mediated by IgE are systemic anaphylaxis caused by drugs, venoms and peanuts, allergic rhinitis, food allergy, and allergic asthma. In addition other self-antigens that expressed on immune cells can also be used for generation of CTLs in vitro as well in vivo for treatment of autoimmune diseases and allergic diseases. Antigenic peptides, proteins or RNA and DNA encoding the non tumor antigens expressed in non tumor cells can also be used to develop vaccines for treatment or prevention of allergy and autoimmune diseases.

BRIEF DESCRIPTION OF THE DRAWINGS

FIG. 1: The amino acid sequences of $IgE^a$ SEQ ID NO: 14 and $IgE^b$ SEQ ID NO: 50 constant regions were aligned with vector NTI software. The sequence differences between the two alleles are bold and underlined.

$CD8^+$ T cells were purified from lymph nodes of CBF1/J mice (A, B and D) or from B6, interferon γ knock out mice ($IFN\gamma^{-/-}$) or perforin ($PF^{-/-}$) knock out mice (C). The purified CD8 T cells were cultured with indicated IgE peptides presented by SC2 cells transfected with $D^b$ MHC class I, B7-1 (CD80) and ICAM-1 (CD54) molecules. Low dose of recombinant IL-2 (20 units/ml) was added to the culture at Day 3 and every other day thereafter. On Day 9, CTL activity was measured against $^{51}$Cr labeled RMAS cells loaded with or without indicated IgE peptides. In FIG. 2, Panel D, anti-$D^b$ mAb (20 µg/ml) was added at the beginning of CTL assay.

Figure 3:
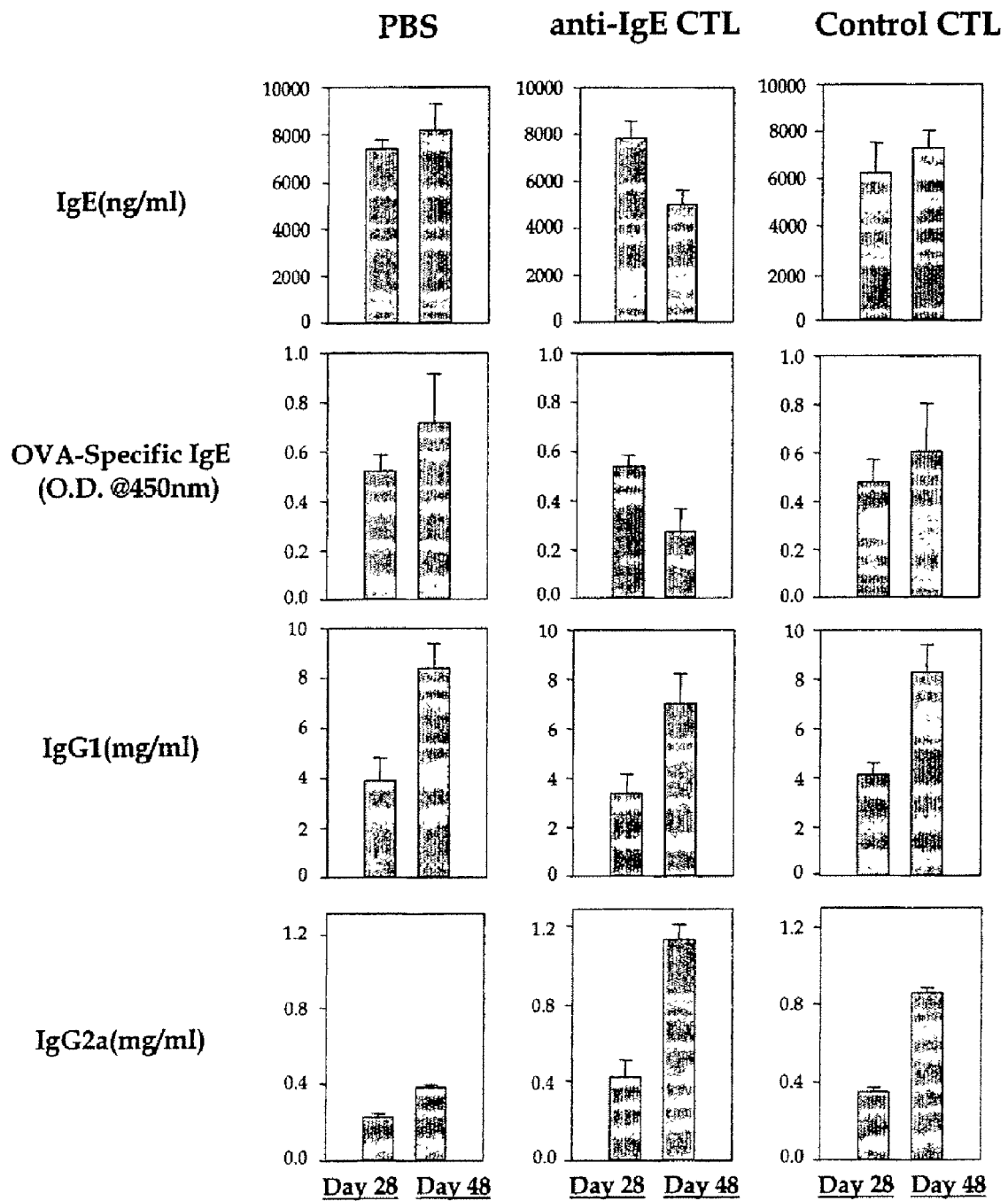
FIG. 3: Adult CBF1/J mice (8 to 12 weeks) were immunized intraperitoneally with 50 µg ovalbumin (OVA) precipitated with Alum Hydroxide on Day 1 and Day 14 respectively. Serum IgE, IgG1 and IgG2a were measured by ELISA on Day 28. Two weeks after the second immunization, the mice were challenged with OVA intranasally every other day for three treatments. IgE-specific CTLs or control CTLs ($5\times10^6$) were give intravenously one day after each challenge. Serum IgG and IgE were measured again two weeks after the last CTL therapy.
Figure 4:
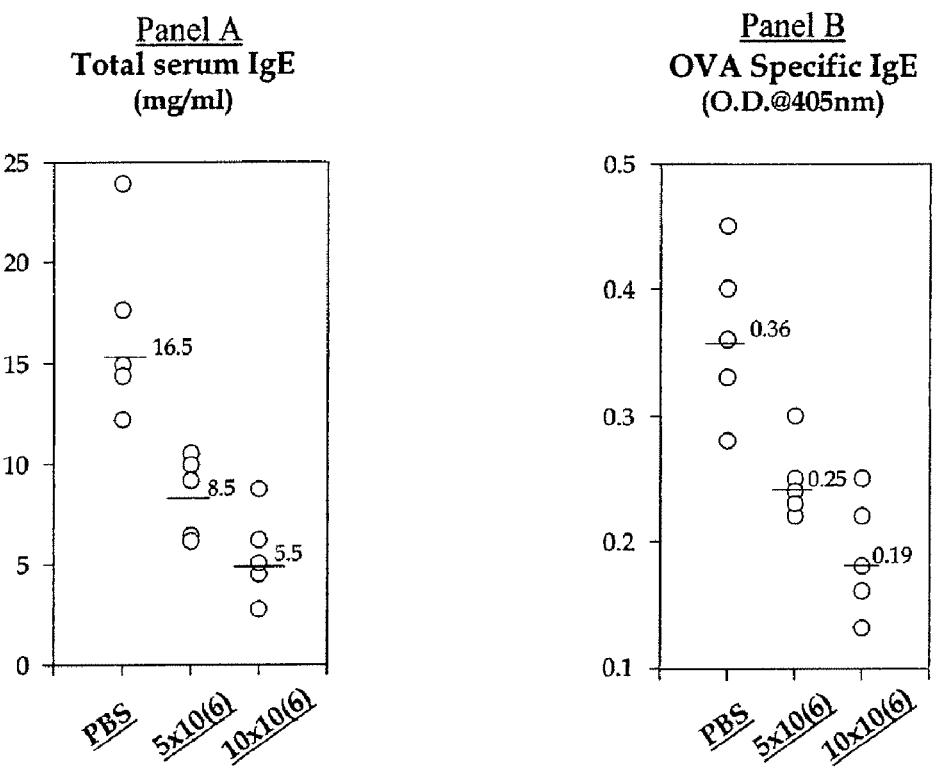
FIG. 4, Panels A, B, C and D.
Figure 4:
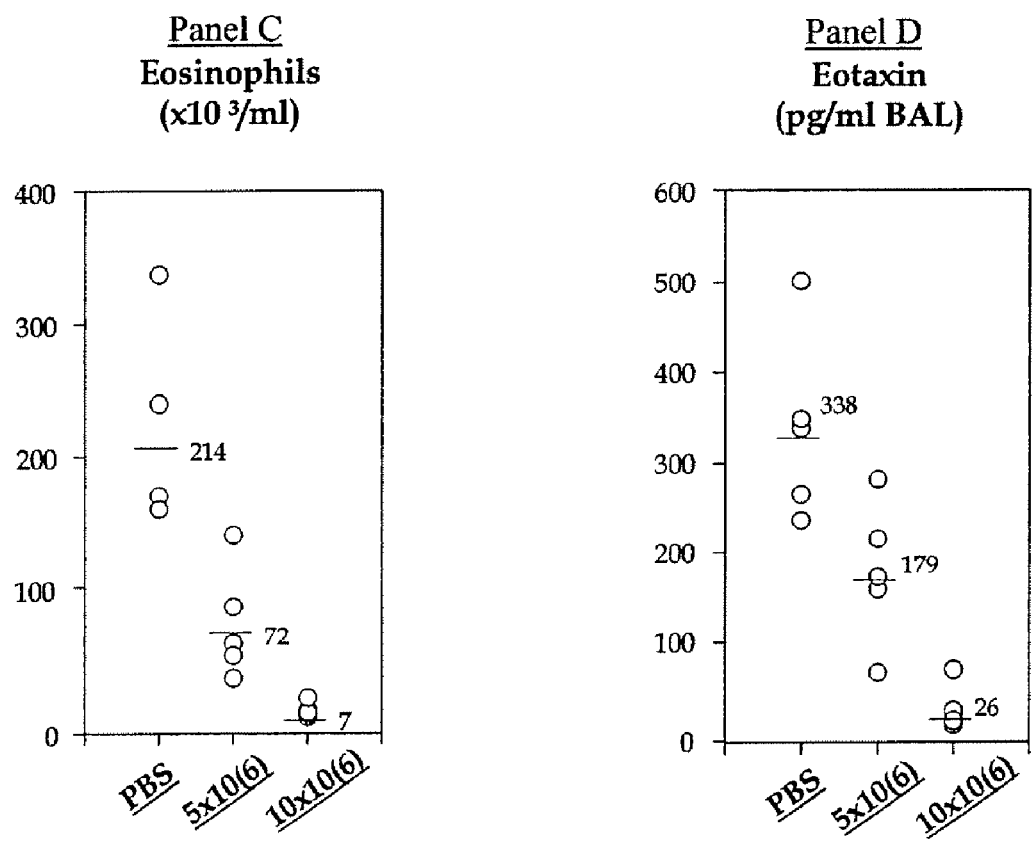

CBF1/J mice were immunized as in FIG. 3. Two weeks after the second immunization, two different doses ($5\times10^6$ and $10\times10^6$) of anti-IgE CTLs were given intravenously three times every other day. Three weeks after the CTL treatment, serum IgE and OVA-specific IgE was measured and challenged with OVA intranasally every other day for three treatments. After the last challenge, bronchial alveolar lavage (BAL) was collected and the total cells in BAL were counted. Eotaxin in the BAL was measured by ELISA and Eosinophils cells in the BAL were differentiated by HE staining.

FIG. 5, Panels A and B:

CBF1/J mice were immunized with OVA/Alum at Day 1 and Day 14. Two weeks after the second immunization, mice were injected every other day for three treatments with PBS, anti-IgE CTL or a control CTL (anti-influenza CTL) as indicated. Three weeks after the last treatment, mice were challenged with OVA intranasally every other day for three treatments. One day after the last challenge with OVA, airway responsiveness to methacholine for each mouse was measured by whole body plethrography. Two independent experiments were shown in Panels A and B respectively.

FIG. 6, Panels A and B:

Adult CBF1/J mice (8 to 12 weeks) were immunized intraperitoneally with 50 µg ovalbumin (OVA) precipitated with Alum Hydroxide on Day 1 and Day 14 respectively. Two weeks after the second immunization, the mice were given IgE-specific CTLs ($5\times10^6$) or PBS intravenously. Three weeks after the last treatment, mice were challenged with OVA intranasally every other day for two to three treatments. One day after the last challenge with OVA, the BAL was prepared from each mouse and the lung from each mouse was fixed and stained with IgE. A representative HE staining of lung tissue from mice received PBS (Panel A) or from mice received anti-IgE CTL (Panel B) was shown.

FIG. 7: The amino acid sequence deduced from cDNA encoding the human IgE constant region. Total RNA was prepared from U266 cell line, which produces human IgE. The total RNA was reverse transcribed and amplified by PCR with two oligoes encoding the 5' and 3' human IgE constant region respectively. The cDNA was cloned into pcDNA3 vector and sequenced.

FIG. 8: Drosophila cells transfected with human HLA-A2 class I cDNA were cultured with a titrated concentration of indicated IgE peptides or control peptide (H690) overnight at room temperature and further cultured at 37° C. for an additional two hours. The cells were washed and stained with anti-HLA-A2 mAb and analyzed by flow cytometry. The mean fluorescence intensity was indicated at Y axis and the peptide concentration was indicated at X axis.

FIG. 9, Panels A, B, C and D:

CD8 T cells were purified from individual donors and cultured with Drosophila cells transfected with HLA-A2, hB7-1, hB7-2, hICAM-1 and hLFA-3 molecules in the presence of indicated peptides. After being cultured for six days, low doses of hIL-2 was added to the culture and re-stimulated with peptides loaded autologous adherent cells for an additional seven days. The CTLs were then harvested and the specific killing activities were tested with $^{51}$Cr labeled T2 cells that loaded with indicated peptides by a standard chromium release assay.

FIG. 10: The amino acid sequence of human IgE was derived as described as in FIG. 6. The antigenic peptides that contain nine amino acids were underlines and the antigenic peptides that contain ten amino acids were shown in bold.

Figure 11:
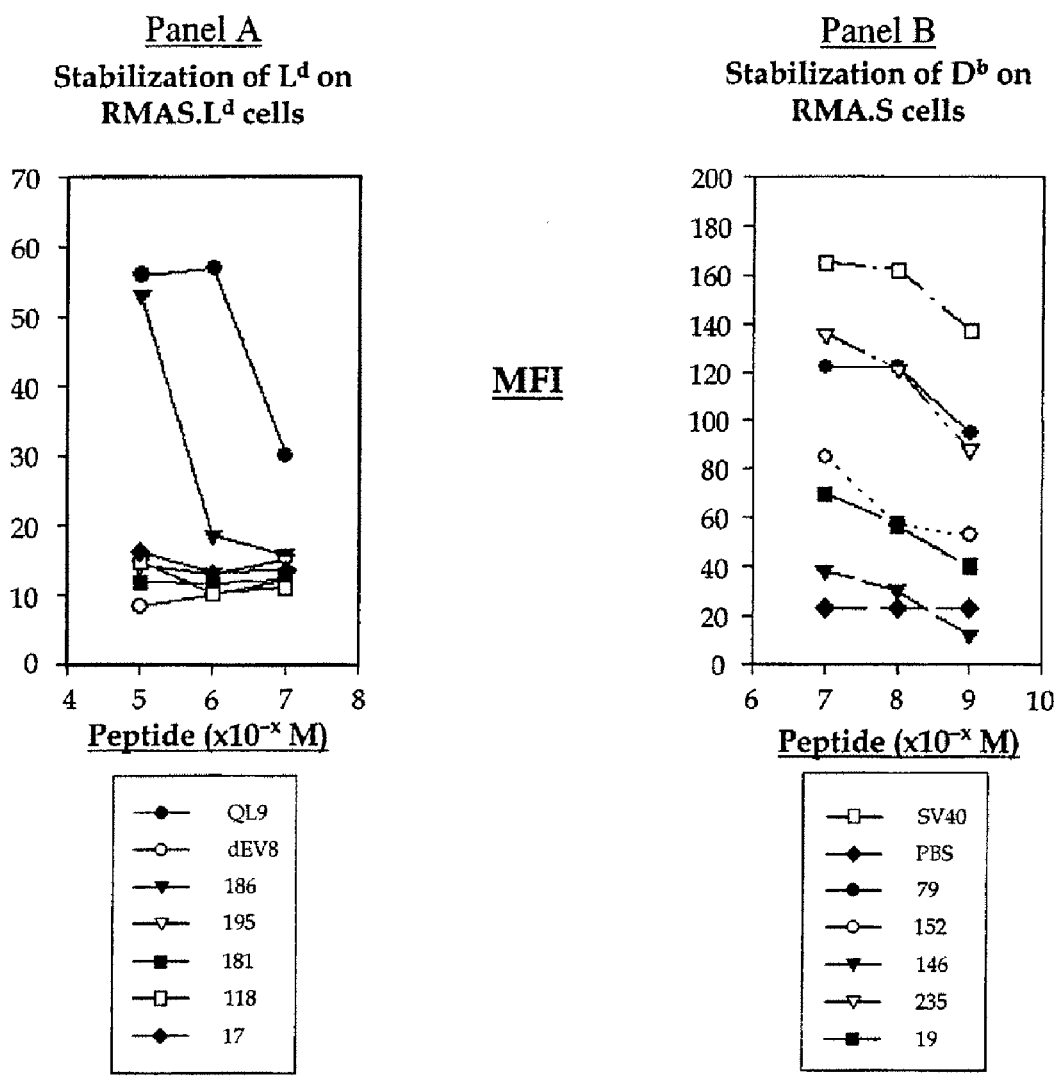

FIG. 11: TAP 2 deficient RMA.S cells (right panel) or $L^d$ transfected RMA.S cells (left panel) were incubated with indicated concentration of peptides at 28° C. overnight and then incubated at 37° C. for two to four hours. The cells were harvested and stained with mAb specific for $L^d$ (right panel) or for $D^b$ (left panel) and analyzed with FACScan.

Figure 12:
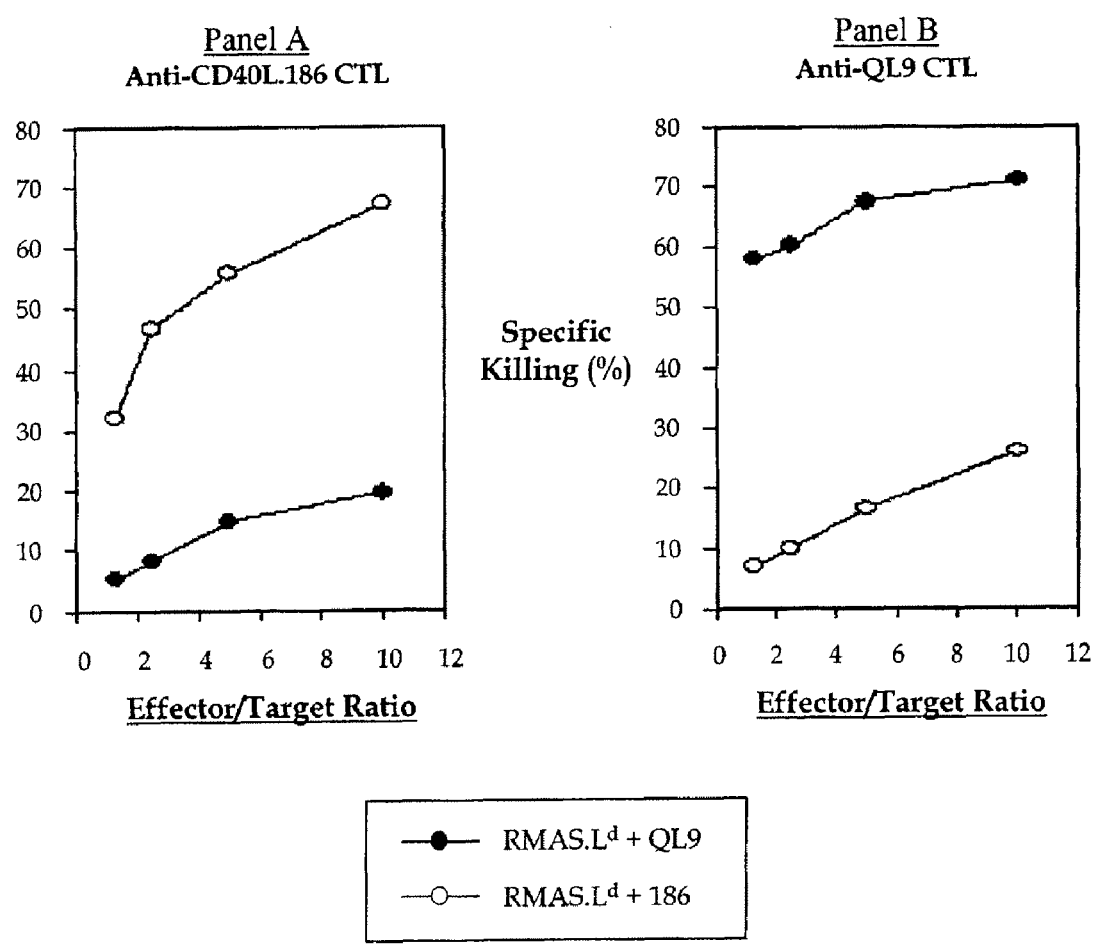

FIG. 12: CD8$^+$ T cells were purified from LN of B10.D2 mice and cultured with Drosophila cells transfected with $L^d$, B7-1 and ICAM-1 in the presence of CD40L.186 peptide (left panel) or QL9 peptide (right panel). IL-2 (20 U/ml) was added to the culture at Days 3 and 5. On Day 7, CTL activity was measured against $^{51}$Cr labeled RMAS.$L^d$ target cells in the presence of indicated peptides.

Figure 13:
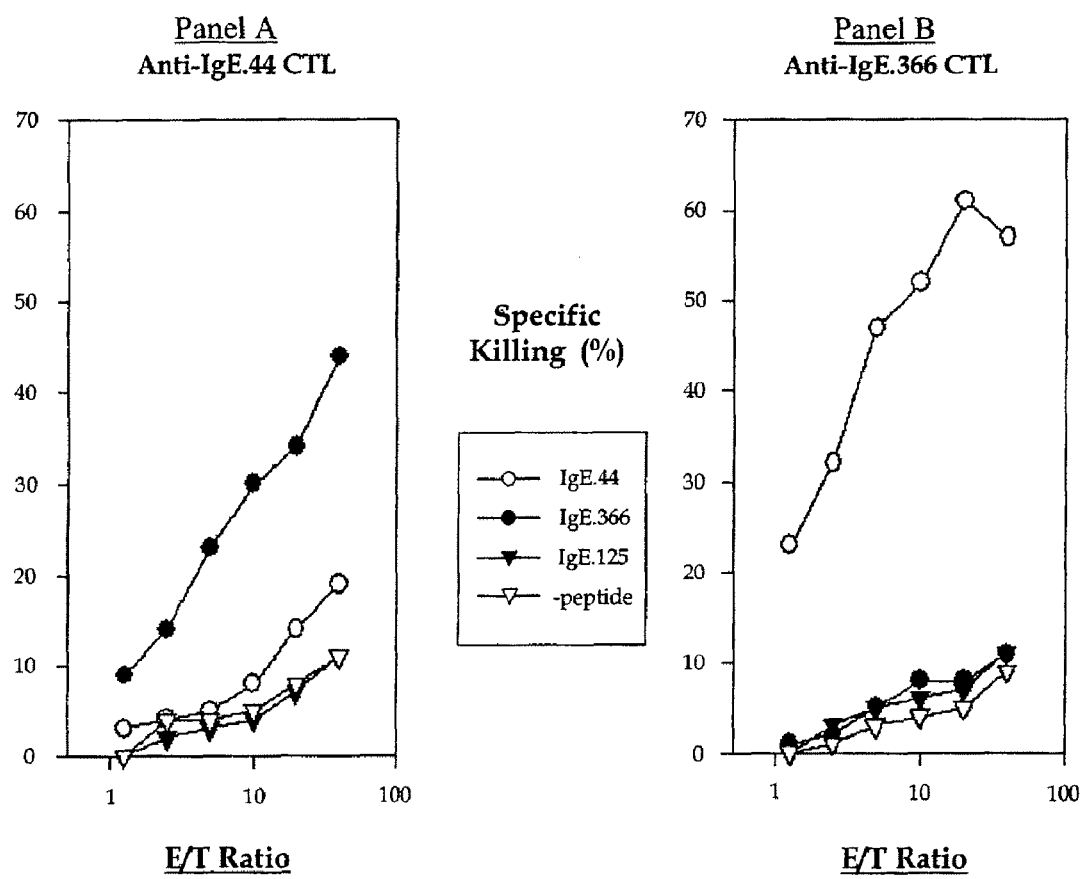

FIG. 13: Purified CD8$^+$ T cells from B6 mice were cultured with Drosophila cells transfected with $D^b$, B7-1 and ICAM-1 in the presence of Ig E.44 peptide (left panel) or Ig E.366 peptide (right panel). IL-2 (20 U/ml) was added to the culture on Days 3 and 5. CTL was harvested on Day 7 and their specific activity was measured against $^{51}$Cr labeled RMA.S target cells in the presence of indicated peptides.

Figure 14:
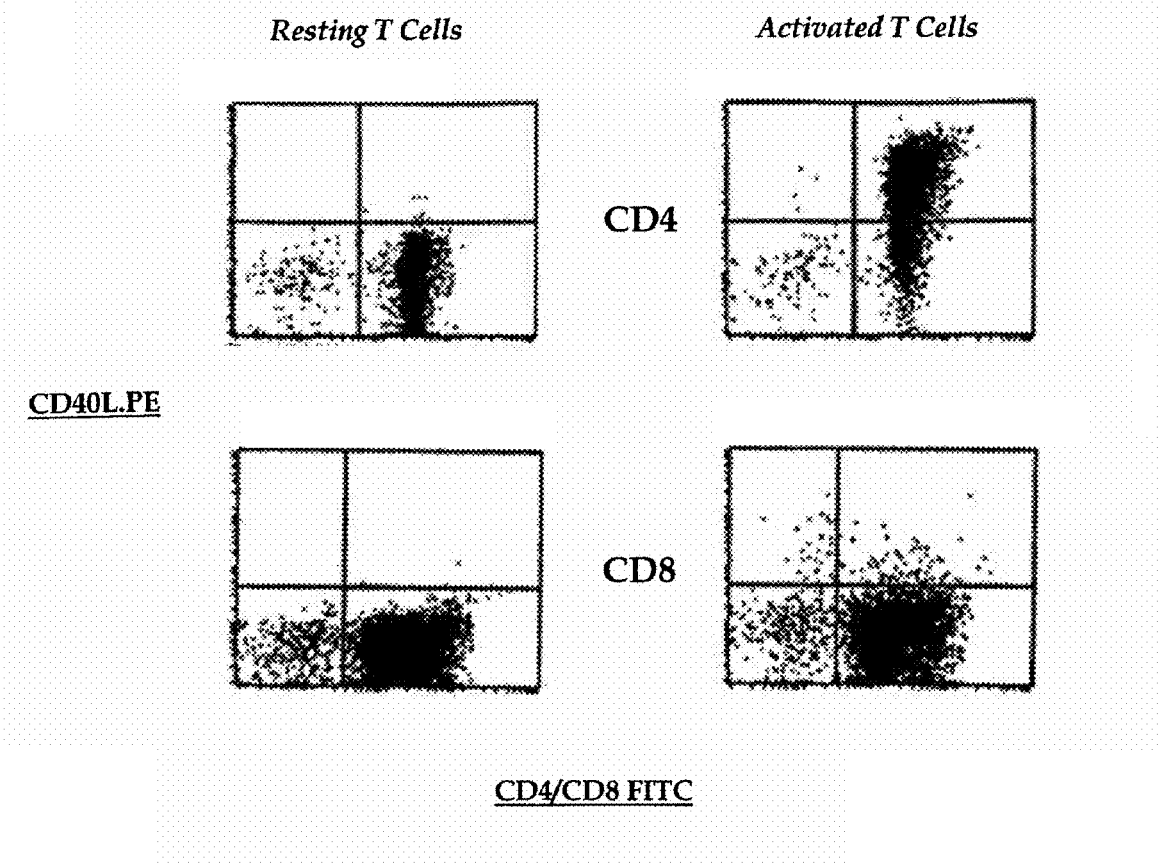

FIG. 14, Panels A and B:

Purified CD4 or CD8 T cells were activated with plate-bound anti-CD3 and anti-CD28 for forty hours (top panel) or for indicated time (bottom panel) and were stained with indicated mAb.1

Figure 15:
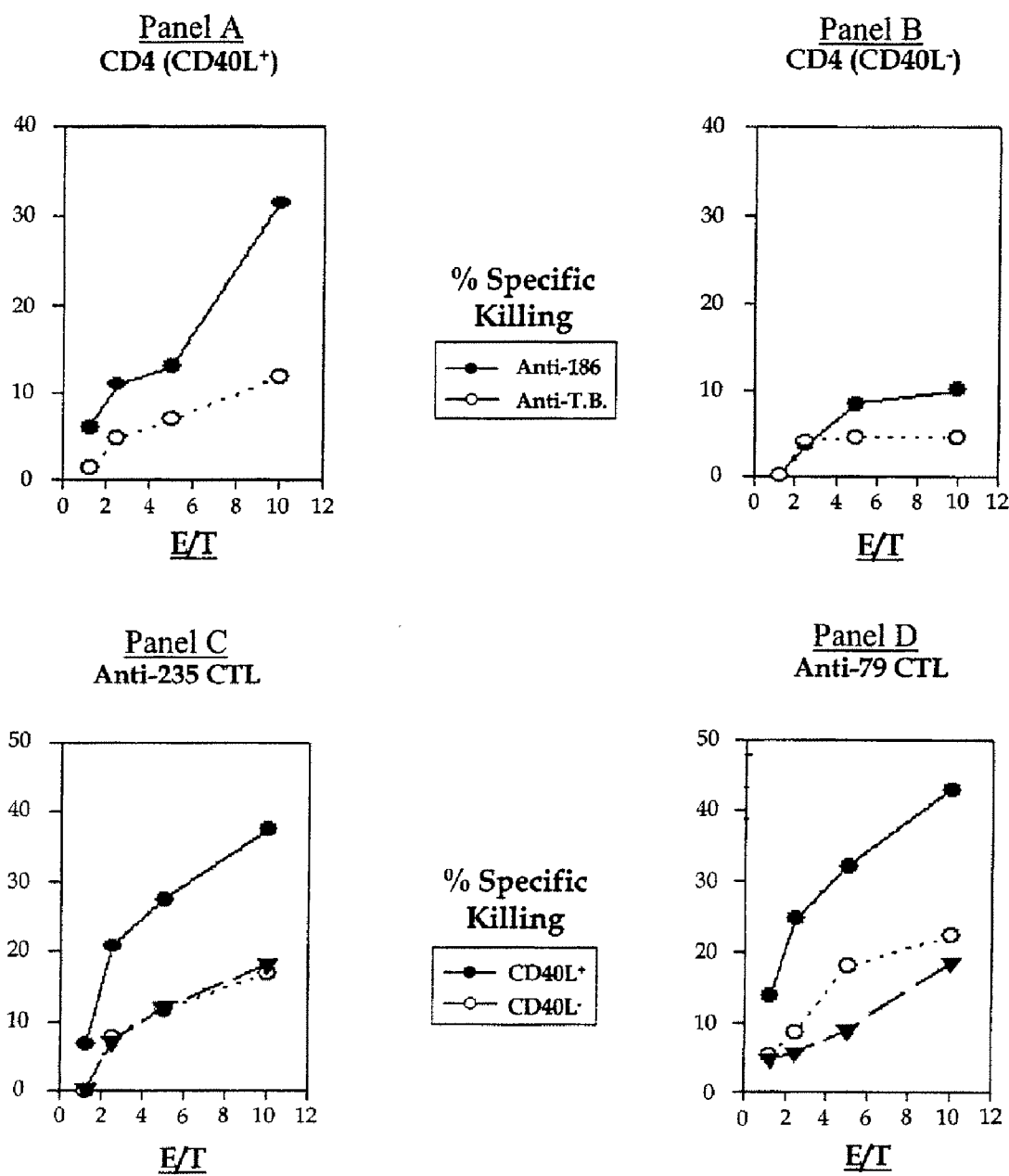

FIG. 15: CD40L specific CTL were generated as described in FIG. 2. CD4 cells used as targets were purified from wild type, CD40L$^{-/-}$ or µ2m$^{-/-}$ mice and activated with anti-CD3 and anti-CD28 for forty hours.

FIG. 16: B10.D2 (top panel) or B6 (bottom panel) were immunized with OVA+CFA and treated with Ab or CTL as indicated. The spleen cells were measured for OVA-producing B cells by ELISA spot at Day 21 after immunization.

Figure 17:
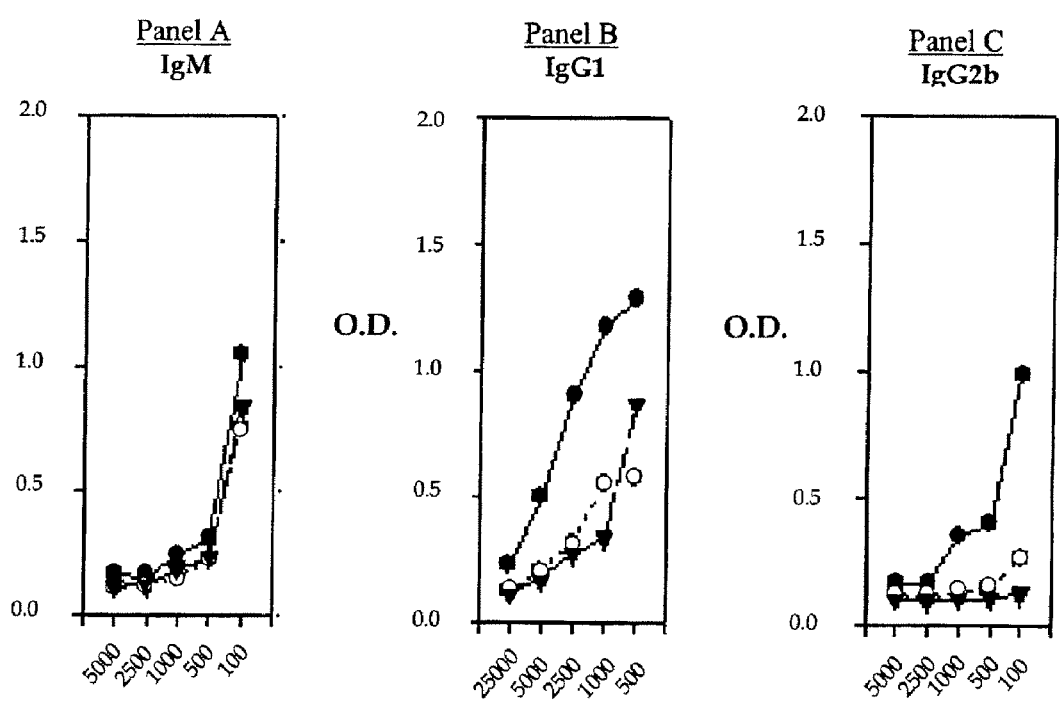

FIG. 17, Panels A, B, C, D and E

B10.D2 mice were immunized with OVA+CFA on Day 1. Anti-CD40L CTL or anti-CD40L Ab were given at Days 1, 3, 5. Serum was collected on Day 14 and OVA-specific immunoglobulins were measured by ELISA.

Figure 18:
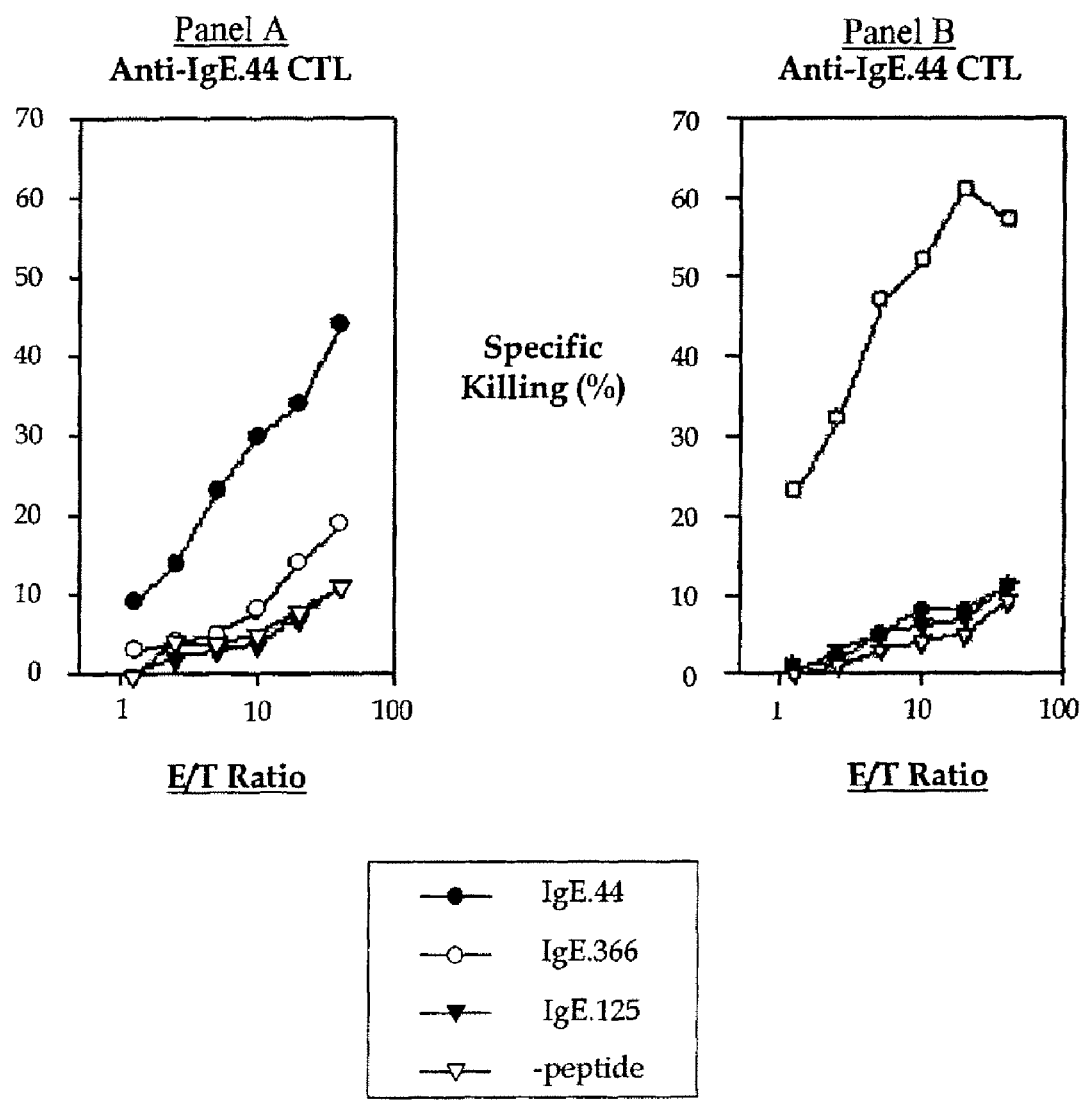
Figure 18:
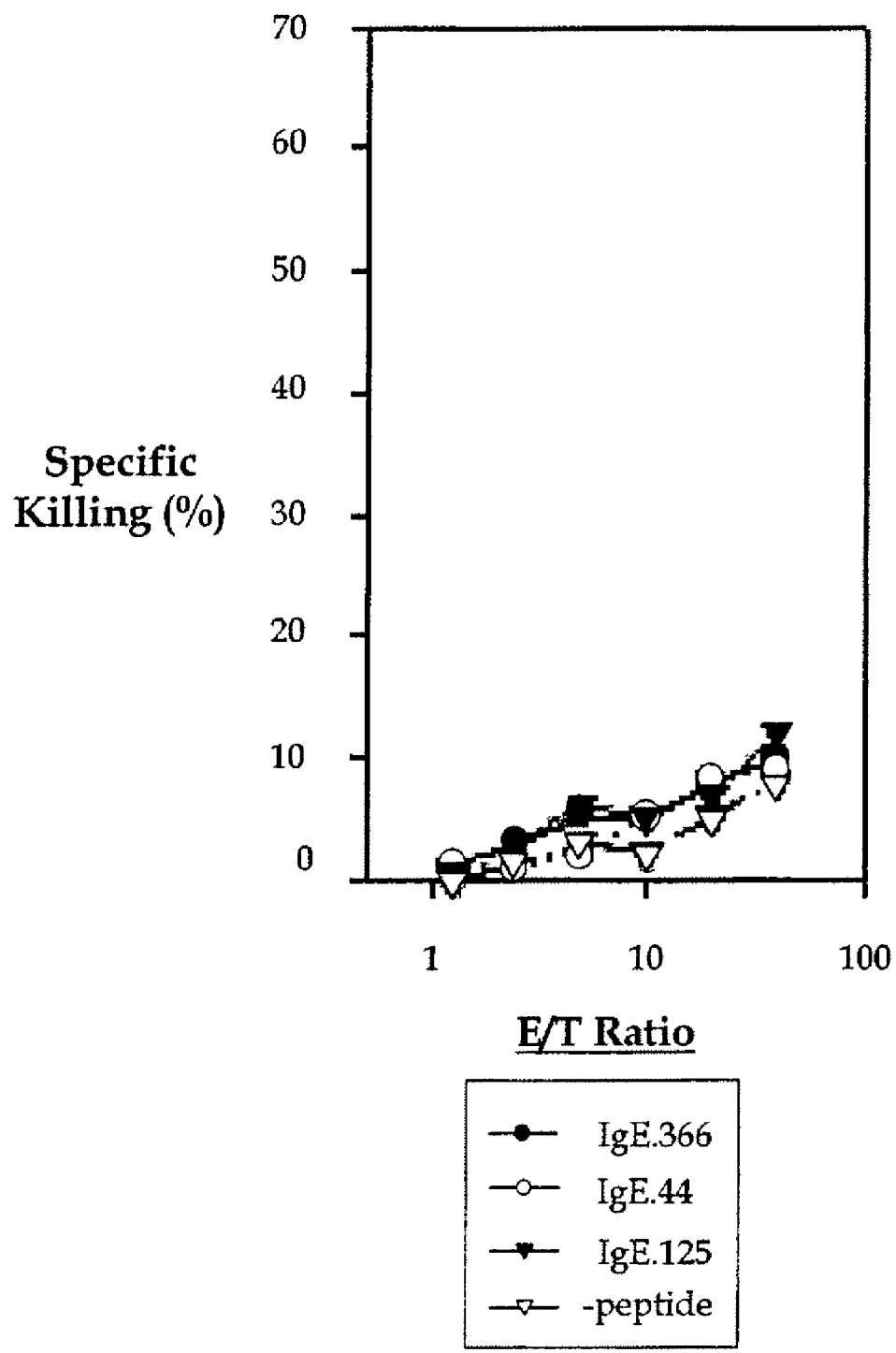

FIG. 18, Panels A, B and C:

CD8 T cells were purified from C57BL/6 mice and cultured with Drosophila cells transfected with $D^b$, B7-1 and ICAM-1 in the presence of IgE.44 peptide (A), IgE.366 peptide (B) and IgE.125 (C). IL-2 (20 units/ml) was added to the culture on Day 3 and 5. CTLs were harvested on Day 7 and their specific killing activity was measured against $^{51}$Cr labeled RMA.S target cells in the presence or absence of indicated peptides.

Figure 19:
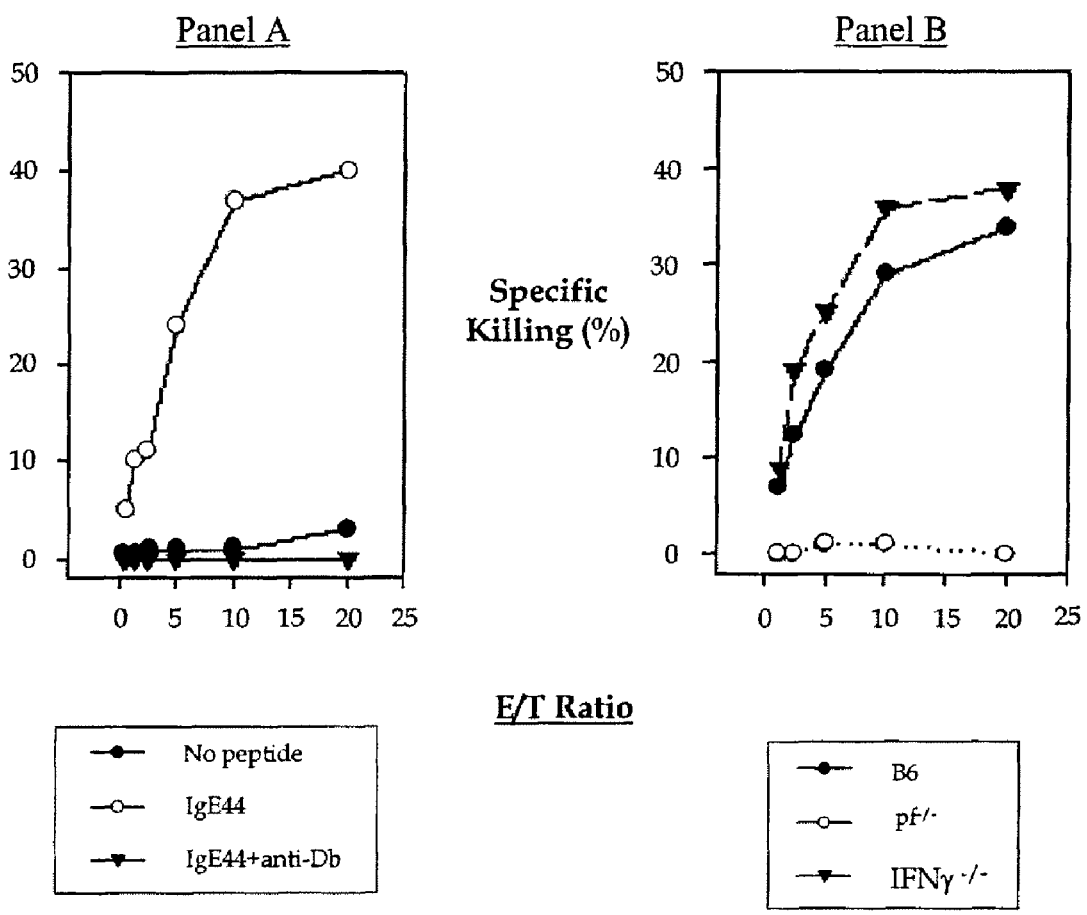

FIG. 19: CD8 T cells were purified from C57BL/6 (B6), perforin knock out mice (pf$^{-/-}$) and IFNγ knock out mice (IFNγ$^{-/-}$) were cultured with Drosophila cells transfected with Db, B7-1 and ICAM-1 in the presence of IgE.44 peptide. IL-2 (20 units/ml) was added to the culture on Day 3 and 5. CTLs were tasted on Day 7 and their specific killing activity was measured against $^{51}$Cr labeled RMA.S target cells in the presence or absence of IgE.44 peptide. In Panel A, CTL activity was measured in the presence or absence of 10 μg/ml of anti-$D^b$ monoclonal antibody.

FIG. 20: CD19$^+$ B cells were purified from human PBMC and cultured with IL-4 (100 ng/ml) and anti-CD40 mAb (5 mg/ml). Anti-IgE CTLs were generated as described on FIG. 9 in the presence of indicated IgE peptides (B) IgE47 and 96, (C) IgE 884 and 890. CTLs were added at Day 4 to the culture B and C. On Day 6, the culture supernatant was collected and human IgE was measured by ELISA. In culture A, no CTLs were added and no B cells in culture D.

DETAILED DESCRIPTION OF THE INVENTION

The present invention provides in one embodiment, a method for treating a subject with non-tumor self-antigen T cell epitopes comprising:
 a. preparing a naturally occurring antigen presenting cell (APC) or a non-naturally occurring antigen-presenting cell line (nnAPC), wherein said APC or said nnAPC is capable of presenting up to about fifteen different peptide molecules that is associated with allergic and/or autoimmune disease, preferably about ten different peptide-epitope molecules, simultaneously where each peptide is about six to twelve amino acids in length, preferably about eight to ten amino acids in length and in a concentration range of about 10 nM to 10 μM;
 b. harvesting CD8$^+$, cells from said subject or a suitable donor;
 c. stimulating said CD8$^+$ cells with said APC or said nnAPC cell line;
 d. adding said CD8$^+$ cells to media that contains a cytokine, such as, IL-2, IL-7 or CGM, preferably, IL-2, or IL-2 and IL-7 in combination;
 e. mixing unsuspended peripheral blood monocytes, or alternatively, CD8-depleted peripheral blood monocytes collected from said subject or a suitable donor with about 10 to 50 μg/ml of a peptide;
 f. irradiating said peripheral blood monocyte suspension with a sufficient dose of γ-radiation necessary to sterilize all components in the suspension, except the desired peripheral blood monocytes, such as a dose in the range of about 3,000 to 7,000 rads, preferably about 5,000 rads;
 g. isolating adherent peripheral blood monocytes;
 h. loading said adherent peripheral blood monocytes with about 10 ng/ml to 10 μg/ml of said each peptide;
 i. combining said CD8$^+$ cells with said adherent peripheral blood monocytes at a ratio of about ten CD8$^+$ cells to one peripheral blood monocyte;
 j. optionally stimulating said combined suspension of CD8$^+$ cells and peripheral blood monocytes for about six to seven days;
 k. optionally stimulating said suspension of CD8$^+$ cells and peripheral blood monocytes with IL-2 and IL-7 in media;
 l. optionally assaying CD8$^+$ suspension for suitable CTL activity, and optionally assaying for CTL purity, sterility and endotoxin content; and
 m. inoculating said subject with CD8$^+$ suspension.

Another embodiment of the present invention provides a method for treating a subject comprising,
 a. preparing a naturally occurring antigen presenting cell (APC) or a non-naturally occurring antigen-presenting cell line (nnAPC), wherein said APC or said nnAPC is capable of presenting up to about fifteen different peptide-epitope molecules that is associated with allergic and/or autoimmune disease, preferably about ten peptides, simultaneously where each peptide is eight to ten amino acids in length;
 b. harvesting CD8$^+$ cells from said subject;
 c. stimulating said CD8$^+$ cells with said APC or said nnAPC cell line for about six to seven days;
 d. stimulating said CD8$^+$ cells with IL-2 and IL-7 in media;
 e. mixing peripheral blood monocytes collected from said subject with about 20 μg/ml of each peptide;
 f. irradiating said CD8-depleted peripheral blood monocyte suspension with about 5,000 rads of γ-radiation;
 g. isolating adherent peripheral blood monocytes;
 h. loading said adherent peripheral blood monocytes with about 100 ng/ml of said epitope;
 i. combining said CD8$^+$ cells with said adherent peripheral blood monocytes at a ratio of about ten CD8$^+$ cells to one peripheral blood monocyte;
 j. stimulating said combined suspension of CD8$^+$ cells and peripheral blood monocytes for about six to seven days;
 k. stimulating said suspension of CD8$^+$ cells and peripheral blood monocytes with IL-2 and IL-7 in media;
 l. assaying CD8$^+$ suspension for suitable CTL activity, purity, sterility and endotoxin content; and
 m. inoculating said subject with CD8$^+$ suspension.

Another embodiment of the present invention provides a method for treating a subject with autoimmune disease, including, but not limited to, rheumatoid arthritis, lupus, psoriasis, autoimmune nephritis, multiple sclerosis, insulin dependent diabetes, autoimmune thyroiditis, Crohn's disease, inflammatory bowel disease, graft versus host disease and transplant rejection, and/or allergic diseases, including, but not limited to, food allergy, hay fever, allergic rhinitis, allergic asthma and venom allergy, comprising:
 a. preparing a naturally occurring antigen-presenting cell (APC) or a non-naturally occurring antigen-presenting cell line (nnAPC), wherein said APC or said nnAPC is capable of presenting up to about fifteen different peptide-epitope molecules that is associated with such diseases, preferably about ten peptides, simultaneously where each peptide is eight to ten amino acids in length;
 b. harvesting CD8$^+$ cells from said subject;
 c. stimulating said CD8$^+$ cells with said APC or said nnAPC cell line for about six to seven days;
 d. stimulating said CD8$^+$ cells with IL-2 and IL-7 in media;
 e. mixing peripheral blood monocytes collected from said subject with about 20 μg/ml of each peptide said APC or said nnAPC can present;
 f. irradiating said CD8-depleted peripheral blood monocyte suspension with about 5,000 rads of γ-radiation;
 g. isolating adherent peripheral blood monocytes;
 h. loading said adherent peripheral blood monocytes with about 100 ng/ml of said epitope;
 i. combining said CD8$^+$ cells with said adherent peripheral blood monocytes at a ratio of about ten CD8$^+$ cells to one peripheral blood monocyte;
 j. stimulating said combined suspension of CD8$^+$ cells and peripheral blood monocytes for about six to seven days;
 k. stimulating said suspension of CD8$^+$ cells and peripheral blood monocytes with IL-2 and IL-7 in media;

l. assaying CD8⁺ suspension for suitable CTL activity, purity, sterility and endotoxin content; and m. inoculating said subject with CD8⁺ suspension.

Another embodiment of the present invention is a method of treating allergic and/or autoimmune diseases wherein the nnAPC presents the following peptides, SEQ ID NO: 15 to SEQ ID NO: 49.

Another embodiment of the present invention is a method of treating a non-cancer disease or disease condition that results in an insufficient or inadequate immune response that is normally associated with Class I HLA molecules, wherein the treatment eliminates infected or transformed cells wherein said elimination has been demonstrated to be mediated by CTLs.

Another embodiment of the present invention is a method of treating a non-cancer disease or disease condition that results in an insufficient or inadequate immune response that is normally associated with Class I HLA molecules, wherein infected or transformed cells that have been shown to be susceptible to elimination by CTL are treated by the method comprising:

a. preparing a naturally occurring antigen presenting cell (APC) or a non-naturally occurring antigen-presenting cell line (nnAPC), wherein said APC or said nnAPC is capable of presenting up to about fifteen different peptide molecules that is associated with said disease or disease condition, preferably about ten different peptide epitope molecules, simultaneously where each peptide is about six to twelve amino acids in length, preferably about eight to ten amino acids in length and in a concentration range of about 10 nM to 100 µM;

b. harvesting CD8⁺ cells from said subject or a suitable donor;

c. stimulating said CD8⁺ cells with said APC or said nnAPC cell line;

d. adding said CD8⁺ cells to media that contains a cytokine, such as, IL-2, IL-7 or CGM, preferably, IL-2, or IL-2 and IL-7 in combination;

e. mixing unsuspended peripheral blood monocytes, or alternatively, CD8-depleted peripheral blood monocytes collected from said subject or a suitable donor with about 10 to 50 µg/ml of a peptide;

f. irradiating said peripheral blood monocyte suspension with a sufficient dose of γ-radiation necessary to sterilize all components in the suspension, except the desired peripheral blood monocytes, such as a dose in the range of about 3,000 to 7,000 rads, preferably about 5,000 rads;

g. isolating adherent peripheral blood monocytes;

h. loading said adherent peripheral blood monocytes with about 10 ng/ml to 10 µg/ml of said each peptide;

i. combining said CD8⁺ cells with said adherent peripheral blood monocytes at a ratio of about ten CD8⁺ cells to one peripheral blood monocyte;

j. optionally stimulating said combined suspension of CD8⁺ cells and peripheral blood monocytes for about six to seven days;

k. optionally stimulating said suspension of CD8⁺ cells and peripheral blood monocytes with IL-2 and IL-7 in media;

l. optionally assaying CD8⁺ suspension for suitable CTL activity, and optionally assaying for CTL purity, sterility and endotoxin content; and m. inoculating said subject with CD8⁺ suspension.

The present invention provides a non-naturally occurring antigen-presenting cell (nnAPC) derived from *Drosophila melanogaster* cells transfected with DNA for expression, wherein the nnAPC is capable of simultaneously presenting up to fifteen different peptide molecules associated with allergic and/or autoimmune disease, preferably ten peptide molecules that are encoded by the DNA.

The present invention provides a non-naturally occurring antigen-presenting cell (nnAPC) derived from *Drosophila melanogaster* cells transfected with human class I HLA, binding, and co-stimulatory molecule's DNA for expression, wherein the nnAPC is capable of presenting up to fifteen different peptide molecules associated with allergic and/or autoimmune disease, preferably ten peptide molecules that are encoded by the DNA simultaneously.

Another embodiment of the present invention provides a nnAPC that presents peptides that are associated with various desired functions that enhance the treatment of the subject. For example, in addition to peptides associated with the disease or disease condition being treated, the nnAPC can present peptides associated with accessory molecules such as, lymphocyte function antigens (LFA-1, LFA-2 and LFA-3), intercellular adhesion molecule 1 (ICAM-1), T-cell co-stimulatory factors (CD2, CD28, B7) enhance cell-cell adhesion or transduce additional cell activation signals.

Another embodiment of the present invention provides a nnAPC that presents peptides that are associated with allergic and/or autoimmune diseases. For example, the peptides associated or derived from IgE may be presented with peptides associated or derived from an allergen, or further in combination with CD40L peptides.

Another embodiment of the present invention provides a method for manufacturing non-naturally occurring antigen-presenting cell (nnAPC) capable of presenting up to ten different peptide molecules associated with allergic and/or autoimmune disease simultaneously, said method comprising of the step:

a. preparing a insect cell line from *Drosophila melanogaster* eggs; alternatively preparing an insect cell line, where cells are grown for twelve days, selected with peptides, preferably tetramers, that are capable of identifying the desired cells, and then expanding said desired cells with OKT3 and IL-2.

b. growing said insect cells a media that is suitable for growing insect cells, preferably Schneider™'s *Drosophila* Medium;

c. making a pRmHa-3 plasmid from a pRmHa-1 expression vector, where said pRmHa-3 plasmid includes a metallothionein promoter, metal response consensus sequences and an alcohol dehydrogenase gene bearing a polyadenylation signal isolated from *Drosophila melanogaster*;

d. inserting into said pRmHa-3 plasmid complementary DNA for human class I HLA A2.1, B7.1, B7.2, ICAM-1, β-2 microglobulin and LFA-3, wherein A2.1 can be substituted with any human class I DNA sequence;

e. transfecting said insect cells with a phshneo plasmid and said pRmHa-3 plasmid containing complementary DNA;

f. creating nnAPC by contacting said insect cells with $CuSO_4$ to induce expression of the transfected genes in said insect cells.

Professional antigen presenting cells, such as dendritic cells and macrophages, can be loaded with IgE peptides (Dalyot-Herman et al. (2000) supra) or IgE recombinant proteins (Paglia et al. (1996) supra) or transduced with virus encoding IgE or fragments of IgE (Yang et al., *Cellular Immunology* (2000) 204:29-37). These modified professional antigen-presenting cells can then be used to activate IgE specific CD8 T cells and generate IgE specific CTLs in vitro. Alternatively, non-professional antigen presenting cells can also be transfected or transduced with a number of genes that encode costimulation molecules plus the genes that encode IgE and a fragment of IgE. The modified non-professional antigen presenting cells thus can be used to stimulate IgE specific CD8 T cells for generation of IgE specific CTLs.

The insect cells of the present invention are grown in a media suitable for growing insects, hereinafter referenced to as "insect growth media". Insect growth media are commercially available from a number of vendors, such as, Schneider™'s *Drosophila* Medium, Grace's Insect Media, and TC-100 Insect Media. Alternatively, insect growth media can be prepared by one of ordinary skill in the art. Typically, the media will include components necessary to promote and sustain the growth of insects cells, such as, inorganic salts (for example, calcium chloride, magnesium sulfate, potassium chloride, potassium phosphate, sodium bicarbonate, sodium chloride, and sodium phosphate), amino acids various carbohydrate and chemical species (Imogene Schneider, *Exp. Zool.* (1964) 156(1):91-104). Alternatively, the media can also include vitamins, minerals, and other components that aid in the growth of insect cells.

Following is a list of abbreviations and definitions used in the present specification.

ABBREVIATIONS

| APC | Antigen-presenting cells |
|---|---|
| CD8+ | CD8+ T cells |
| CTL | Cytotoxic T lymphocyte |
| FAS | Also known as CD95, epitope on T cells |
| ICAM | Intercellular adhesion molecule |
| IL | Interleukin |
| LFA | Lymphocyte function antigens |
| MHC | Major histocompatibility complex |
| nnAPC | Non-naturally occurring antigen-presenting cell |
| PBMC | Peripheral blood mononuclear cell |
| PBS | Phosphate-buffered saline |
| PCR | Polymerase chain reaction |
| RPMI | Roswell Park Memorial Institute |
| RWJPRI | The R.W. Johnson Pharmaceutical Research Institute |
| T | Target |
| TCR | T cell antigen receptor |

Following is a list of abbreviations used in the present specification for various peptide epitopes. The individual amino acid residues are identified according to a single letter code that is readily known and used by those of ordinary skill in the art.

| | ABBREVIATIONS | |
|---|---|---|
| AMINO ACID | 3-Letter | 1-Letter |
| alanine | ala | A |
| valine | val | V |
| leucine | leu | L |
| isoleucine | ile | I |
| proline | pro | P |
| phenylalanine | phe | F |
| trytophan | tyr | W |
| methionine | met | M |
| glycine | gly | G |
| serine | ser | S |
| threonine | thr | T |
| cysteine | cys | C |
| tyrosine | tyr | Y |

-continued

| | ABBREVIATIONS | |
|---|---|---|
| AMINO ACID | 3-Letter | 1-Letter |
| asparagine | asn | N |
| glutamine | gln | Q |
| aspartic acid | asp | D |
| glutamic acid | glu | E |
| lysine | lys | K |
| arginine | arg | R |
| histidine | his | H |

Peptide Epitope Abbreviations

As used herein the term IgE 11 refers to the amino acid sequence KPCKGTASM (SEQ ID NO: 1).

As used herein the term IgE 209 refers to the amino acid sequence IPPSPLDLY (SEQ ID NO: 2).

As used herein the term IgE 366 refers to the amino acid sequence GSNQGFHF (SEQ ID NO: 3).

As used herein the term IgE 29 refers to the amino acid sequence FPNPVTVTW (SEQ ID NO: 4).

As used herein the term IgE 105 refers to the amino acid sequence HSSCDPNAF (SEQ ID NO: 5).

As used herein the term IgE 114 refers to the amino acid sequence HSTIQLYCF (SEQ ID NO: 6).

As used herein the term IgE 363 refers to the amino acid sequence KSNGSNQGF (SEQ ID NO: 7).

As used herein the term IgE 307 refers to the amino acid sequence RSAPEVYVF (SEQ ID NO: 8).

As used herein the term IgE 44 refers to the amino acid sequence MSTVNFPAL (SEQ ID NO: 9).

As used herein the term IgE 411 refers to the amino acid sequence TSLGNTSLR (SEQ ID NO: 10).

As used herein the term IgE 16 refers to the amino acid sequence TASMTLGCL (SEQ ID NO: 11).

As used herein, the term IgE 159 refers to the amino acid sequence of ASTCSKLNI (SEQ ID NO: 12).

As used herein, the term IgE 125 refers to the amino acid sequence of GHILNDVSV (SEQ ID NO: 13).

As used herein the term CD40L 17 refers to the amino acid sequence LPASMKIFM (SEQ ID NO: 15).

As used herein the term CD40L 186 refers to the amino acid sequence RPFIVGLWL (SEQ ID NO: 16).

As used herein the term CD40L 118 refers to the amino acid sequence DPQIAAHVV (SEQ ID NO: 17).

As used herein the term CD40L 220 refers to the amino acid sequence QSVHLGGVF (SEQ ID NO: 18).

As used herein the term CD40L 9 refers to the amino acid sequence SPRSVATGL (SEQ ID NO: 19).

As used herein the term CD40L 195 refers to the amino acid sequence KPSIGSERI (SEQ ID NO: 20).

As used herein the term CD40L 252 refers to the amino acid sequence FSSFGLLKL (SEQ ID NO: 21).

As used herein the term CD40L 7 refers to the amino acid sequence QPSPRSVAT (SEQ ID NO: 22).

As used herein the term CD40L 181 refers to the amino acid sequence EPSSQRPFI (SEQ ID NO: 23).

As used herein the term CD40L 79 refers to the amino acid sequence LSLLNCEEM (SEQ ID NO: 24).

As used herein, the term CD40L 152 refers to the amino acid sequence of VMLENGKQL (SEQ ID NO: 25).

As used herein, the term CD40L 146 refers to the amino acid sequence of TMKSNLVML (SEQ ID NO: 26).

As used herein, the term CD40L 235 refers to the amino acid sequence of SVFVNVTEA (SEQ ID NO: 27).

As used herein, the term CD40L 38 refers to the amino acid sequence of GSVLFAVYL (SEQ ID NO: 28).

As used herein, the term CD40L 19 refers to the amino acid sequence of ASMKIFMYL (SEQ ID NO: 29).

As used herein the term CD40L 24 refers to the amino acid sequence FMYLLTVFL (SEQ ID NO: 30).

As used herein the term CD40L 167 refers to the amino acid sequence GLYYIYAQV (SEQ ID NO: 31).

As used herein the term CD40L 22 refers to the amino acid sequence KIFMYLLTV (SEQ ID NO: 32).

As used herein the term CD40L 36 refers to the amino acid sequence MIGSALFAV (SEQ ID NO: 33).

As used herein the term CD40L 58 refers to the amino acid sequence NLHEDFVFM (SEQ ID NO: 34).

As used herein the term CD40L 170 refers to the amino acid sequence YIYAQVTFC (SEQ ID NO: 35).

As used herein the term CD40L 26 refers to the amino acid sequence YLLTVFLIT (SEQ ID NO: 36).

As used herein the term CD40L 231 refers to the amino acid sequence LQPGASVFV (SEQ ID NO: 37).

As used herein the term CD40L 45 refers to the amino acid sequence YLHRRLDKI (SEQ ID NO: 38).

As used herein the term CD40L 147 refers to the amino acid sequence TMSNNLVTL (SEQ ID NO: 39).

As used herein, the term CD40L 229 refers to the amino acid sequence of FELQPGASV (SEQ ID NO: 40).

As used herein, the term CD40L 160 refers to the amino acid sequence of QLTVKRQGL (SEQ ID NO: 41).

As used herein, the term CD40L 35 refers to the amino acid sequence of QMIGSALFA (SEQ ID NO: 42).

As used herein, the term CD40L 185 refers to the amino acid sequence of SQAPFIASL (SEQ ID NO: 43).

As used herein, the term CD40L 19 refers to the amino acid sequence of ISMKIFMYL (SEQ ID NO: 44).

As used herein, the term CD40L 153 refers to the amino acid sequence of VTLENGKQL (SEQ ID NO: 45).

As used herein, the term CD40L 126 refers to the amino acid sequence of VISEASSKT (SEQ ID NO: 46).

As used herein, the term CD40L 227 refers to the amino acid sequence of GVFELQPGA (SEQ ID NO: 47).

As used herein, the term CD40L 20 refers to the amino acid sequence of SMKIFMYLL (SEQ ID NO: 48).

As used herein, the term CD40L 165 refers to the amino acid sequence of RQGLYYIYA (SEQ ID NO: 49).

As used herein, the term IgE 47 refers to the amino acid sequence of SLNGTTMTL NO: 50).

As used herein, the term IgE 96 refers to the amino acid sequence of WVDNKTFSV (SEQ ID NO: 51).

As used herein, the term IgE 185 refers to the amino acid sequence of WLSDRTYTC (SEQ ID NO: 52).

As used herein, the term IgE 309 refers to the amino acid sequence of ALSDRTYTC (SEQ ID NO: 53).

As used herein, the term IgE 876 refers to the amino acid sequence of SLLTVSGAWA (SEQ ID NO: 54).

As used herein, the term IgE 883 refers to the amino acid sequence of WLEDGQVMDV (SEQ ID NO: 55).

As used herein, the term IgE 884 refers to the amino acid sequence of TLTVTSTLPV (SEQ ID NO: 56).

As used herein, the term IgE 887 refers to the amino acid sequence of QMFTCRVAHT (SEQ ID NO: 57).

As used herein, the term IgE 890 refers to the amino acid sequence of YATISLLTV (SEQ ID NO: 58).

As used herein, the term IgE 895 refers to the amino acid sequence of TLACLIQNFM (SEQ ID NO: 59).

As used herein, the term IgE 898 refers to the amino acid sequence of QVMDVDLSTA (SEQ ID NO: 60).

Terms and Definitions

As used herein, the term "adoptive immunotherapy" refers the administration of donor or autologous T lymphocytes for the treatment of a disease or disease condition, wherein the disease or disease condition results in an insufficient or inadequate immune response that is normally associated with Class I HLA molecules. Adoptive immunotherapy is an appropriate treatment for any disease or disease condition where the elimination of infected or transformed cells has been demonstrated to be achieved by CTLs. For example, disease or disease conditions include but are not limited to cancer and/or tumors, such as, melanoma, prostate, breast, colo-rectal, stomach, throat and neck, pancreatic, cervical, ovarian, bone, leukemia and lung cancer; viral infections, such as, hepatitis B, hepatitis C, human immunodeficiency virus; and bacterial infections, such as, malaria; tuberculosis, and lysteria monocytogenesis.

As used herein, the term "B7.1" refers to a co-stimulatory molecule associated with antigen-presenting cells.

As used herein, the term "BCNU" refers to carmustine, also known as, 1,3-bis (2chloroethyl)-1-nitrosourea.

As used herein, the term "BSE" refers to bovine spongiform encephalitis.

As used herein, the term "CD" refers to clusters of differentiation, T lymphocytes (originally), B lymphocytes, monocytes, macrophages, and granulocytes grouped by antigen epitopes and function.

As used herein, the term "DTIC" refers to dacarbazine, 5-(3,3-dimethyl-1-triazeno)-imidazole-4-carboxamide.

As used herein, the term "ex vivo" or "ex vivo therapy" refers to a therapy where biological materials, typically cells, are obtained from a patient or a suitable alternate source, such as, a suitable donor, and are modified, such that the modified cells can be used to treat a pathological condition which will be improved by the long-term or constant delivery of the therapeutic benefit produced by the modified cells. Treatment includes the re-introduction of the modified biological materials, obtained from either the patient or from the alternate source, into the patient. A benefit of ex vivo therapy is the ability to provide the patient the benefit of the treatment, without exposing the patient to undesired collateral effects from the treatment. For example, cytokines are often administered to patients with cancer or viral infections to stimulate expansion of the patient's CTLs. However, cytokines often cause the onset of flu like symptoms in the patients. In an ex vivo procedure, cytokines are used to stimulate expansion of the CTLs outside of the patient's body, and the patient is spared the exposure and the consequent side effects of the cytokines. Alternatively under suitable situations, or conditions, where appropriate and where the subject can derive benefit, the subject can be treated concurrently with low level dosages of a interferon.

As used herein, the term "HEPES" refers to N-2-hydroxyethylpiperazine-N'2-ethanesulfonic acid buffer.

As used herein, the term "HLA-A2.1" refers to a HLA Class I molecule found in approximately 45% of Caucasians.

As used herein, the term "MPC-10" refers to a magnetic particle concentrator.

As used herein, the term "NK cells" refers to natural killer cells.

As used herein, the term "OKT3" refers to ORTHOCLONE OKT3, muromonab-CD3, anti-CD3 monoclonal antibody.

As used herein, the term "TAP-1, 2" refers to Transporter Associated with Antigen Processing-1, 2.

As used herein, the term "Th cells" refers to Helper T cells, CD4$^+$.

As used herein, the term "C-lectin" refers to a peptide of the sequence that has been found to be associated with ovarian cancer.

As used herein, the term "major histocompatibility complex" or "MHC" is a generic designation meant to encompass the histocompatibility antigen systems described in different species including the human leucocyte antigens (HLA).

As used herein, the terms "epitope," "peptide epitope," "antigenic peptide" and "immunogenic peptide" refers to a peptide derived from an antigen capable of causing a cellular immune response in a mammal. Such peptides may also be reactive with antibodies from an animal immunized with the peptides. Such peptides may be about five to twenty amino acid in length preferably about eight to fifteen amino acids in length, and most preferably about nine to ten amino acids in length.

As used herein, the term "analog" includes any polypeptide having an amino acid residue sequence substantially identical to the polypeptide sequence of the present invention in which one or more residues have been conservatively substituted with a functionally similar residue and which displays the functional aspects of the present invention as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

As used herein, the term "conservative substitution" also includes the use of a chemically derivatized residue in place of a non-derivatized residue.

As used herein, the term "chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded is the corresponding nucleic sequence of the present invention, so long as the requisite activity is maintained.

Cytolytic T cells ($CD8^+$) are the main line of defense against viral infections. $CD8^+$ lymphocytes specifically recognize and kill host cells that are infected by a virus. Theoretically, it should be possible to harness the immune system to combat other types of diseases including cancer. However, few in vitro/ex vivo procedures have been available for specifically activating CTLs. The identification of key allergic and/or autoimmune antigens noted herein and a method for specific in vitro activation CTLs described below now allow testing of the concept of adoptive immunotherapy of allergic and/or autoimmune diseases.

All naive T cells require two signals for activation to elicit an immune response. For $CD8^+$ lymphocytes (CTLs), the first signal, which imparts specificity, consists of presentation to the $CD8^+$ cell of an immunogenic peptide fragment (epitope) of the antigen bound to the Class I MHC (HLA) complex present on the surface of antigen-presenting cells (APCs). This complex is recognized specifically by a T cell antigen receptor (TCR), which communicates the signal intracellularly.

Binding to the T cell receptor is necessary but not sufficient to induce T cell activation, and usually will not lead to cell proliferation or cytokine secretion. Complete activation requires a second co-stimulatory signal(s), these signals serve to further enhance the activation cascade. Among the co-stimulatory molecules on antigen-presenting cells, B7 and cell adhesion molecules (integrins) such as ICAM-1 assist in this process by binding to CD28 and LFA-1, respectively, on the T cell. When a $CD8^+$ cell interacts with an antigen-presenting cell bearing an immunogenic peptide (epitope) bound by a Class I MHC molecule in the presence of appropriate co-stimulatory molecule interactions, the $CD8^+$ cell becomes a fully activated cytolytic T cell.

Lymphocyte-mediated cell killing involves a sequence of biological events beginning with the binding of the $CD8^+$ CTL to an antigen-bearing target (tumor) cell by means of the recognition process described above for T cell activation. The interaction begins with the binding of antigen in association with an MHC Class I molecule on the APC or target cell to the T cell antigen receptor (TCR). Accessory molecules such as lymphocyte function antigens (LFA-1, LFA-2 and LFA-3), intercellular adhesion molecule 1 (ICAM-1), T cell co-stimulatory factors (CD2, CD28, B7) enhance cell-cell adhesion or transduce additional cell activation signals.

After cell-cell interaction, the CTL kills the target cell through the action of soluble cytolytic mediators (perforin and granzymes stored in cytoplasmic granules in the T cell) and a CTL surface molecule (FAS ligand). After the cytolytic attack, target cells die by necrosis (membrane perforation and organelle destruction) or apoptosis (chromatin condensation, DNA fragmentation and membrane blebbing).

Figure 2:
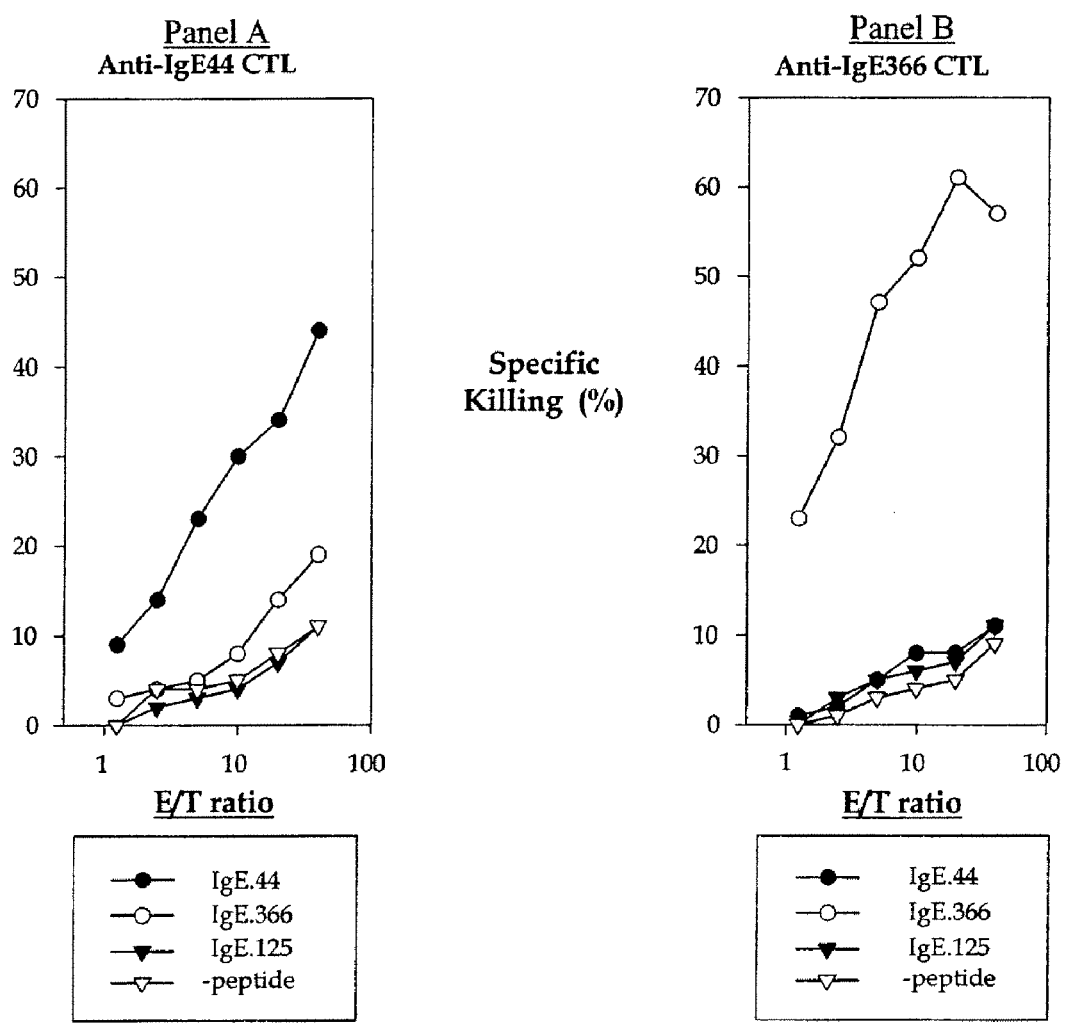
FIG. 2, Panels A, B, C and D.
Figure 2:
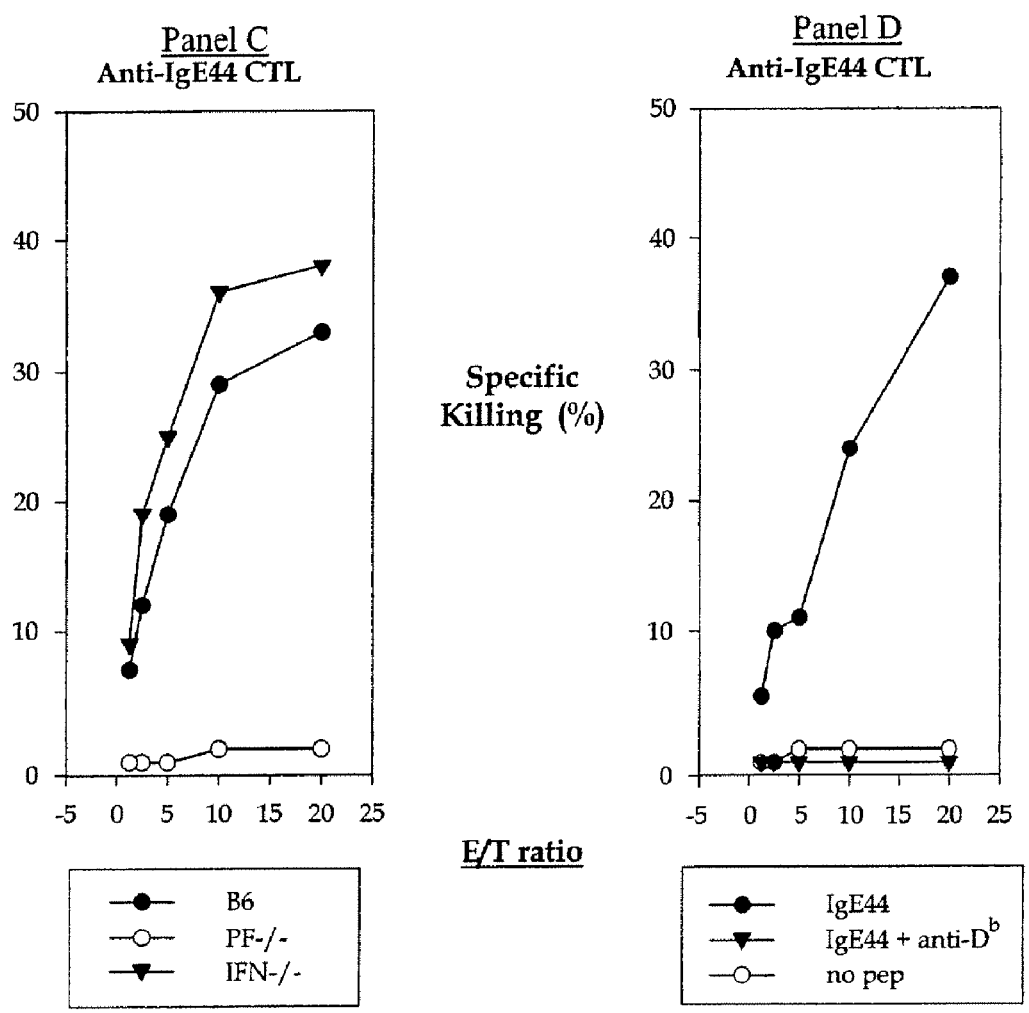

The mechanisms of lymphocyte-mediated cytolysis is graphically depicted in FIG. 2. In Panel A of FIG. 2, after binding to the target cell, cytoplasmic granules in the CTL are rapidly reoriented toward the target cell for release of granules containing perforin and granzymes into the intercellular space. These proteolytic enzymes form pores in the plasma membrane of the target cell eventually leading to cell necrosis. In Panel B, after binding to the target cell, the level of FAS expression on the CTL increases. The interaction of FAS and the FAS receptor on the target cell leads to apoptosis. Proteases such as CPP32 and others related to IL-1b-converting enzyme (ICE) have been implicated in the induction of apoptosis.

It is possible to use naturally-occurring antigen-presenting cells, for example, dendritic cells, macrophages, autologous tumor cells for in vitro $CD8^+$ activation. However, the efficiency of activation following this approach is low. This is because the Class I molecules of native APCs contain many other types of peptide epitopes besides tumor epitopes. Most of the peptides are derived from normal innocuous cell proteins, resulting in a dilution of the number of active native APCs that would actually be effective against a tumor (Allison et al., *Curr. Op. Immunol.* (1995) 7:682-686).

A more direct and efficient approach to this problem is to specifically activate CD8+ cells only with those epitopes relevant to combating a specific disease, (such as allergic and/or autoimmune disease). To this end, an artificial antigen presenting cell is created by expressing MHC Class I molecules in *Drosophila melanogaster* (fruit fly) cells. Since *Drosophila* does not have an immune system, the TAP-1,2 peptide transporters involved in loading peptide epitopes onto class I molecules are absent. As a result, the class I molecules appear on the *Drosophila* cell surface as empty vessels. By incubating these transfected *Drosophila* cells with exogenous peptides that bind to the class I molecules, such as, cancer or tumor specific epitopes, including but not limited to, melanoma specific epitopes, it is possible to occupy every class I molecule with the same peptide. High density expression of class I molecules containing a single peptide in these *Drosophila* APCs permit generation of cytotoxic CD8+ T cells in vitro which are completely specific for the antigen peptide. Methods and procedures for preparing *Drosophila* cells are taught in U.S. Pat. No. 5,529,921 issued Jun. 25, 1996 entitled "In Vitro Activation of Cytotoxic T-Cells Using Insect Cells Expressing Human Class I MHC and β2-Microglobulin", and U.S. Pat. No. 5,314,813 issued May 24, 1994 entitled "*Drosophila* Cell Lines Expressing Genes Encoding MHC Class I Antigens And β2-Microglobulin and Capable of Assembling Empty Complexes and Methods of Making Said Cell Lines". In particular, U.S. Pat. No. 5,529,921 discloses at column 26, line 56 to column 28, line 22 various methods of separating out and/or enriching cultures of precursor cells.

Additionally, this feature eliminates the need for in vivo stimulation of the immune system with various cytokines. Thereby resulting in a treatment that fore goes the side effects caused by cytokines. Alternatively under suitable situations, or conditions, where appropriate and where the subject can derive benefit, the subject can be treated concurrently with low level dosages of α interferon.

Eliminating the need for in vivo stimulation with cytokines provides an improvement to the quality of patient care. Treatment regimes that include the administration of cytokines to patients often result in the patient developing flu-like symptoms, such as nausea, vomiting, and fever. These side reactions are generally not life threatening, although a particularly severe reaction occurring in a patient who is already in a weaken condition could result in a life endangering situation. Another consideration is the adverse impact such side reactions have on patient acceptance and compliance of an otherwise beneficial treatment regime. Removing the need for in vivo stimulation with cytokines results in a treatment regime that improves the comfort of the patient, and provides the clinician with an effective method of treatment that his or her patient is more likely to comply with.

The utility of this method for adoptive immunotherapy has been demonstrated in mice using transfected *Drosophila* cells as APCs and CD8+ cells from the 2C line of T cell receptor (TCR) transgenic mice. In this system, purified CD8+ 2C cells are highly responsive to in vitro peptides presented by MHC Class I ($L^d$)-transfected *Drosophila* cells also bearing the co-stimulatory molecules B7-1 and ICAM-1. Transfected *Drosophila* cells as a probe for defining the minimal requirements for stimulating unprimed CD8+ T cells (Cai et al., *P.N.A.S. USA* (1996) 93:14736-14741). Alternatively, when un-separated mouse spleen cells are used as responders in place of purified 2C cells, the need for co-stimulatory molecules does not apply. In this instance, the CD8+ cells in the spleen population receive "bystander" co-stimulation from activated B cells. Utilizing this finding, it has been possible to show that MHC Class I ($L^d$)-transfected *Drosophila* cells are able to induce normal DBA/2 mouse spleen cells to respond to syngeneic P815 mastocytoma tumor-specific peptides in vitro in the absence of added lymphokines. Injection of these CTLs into DBA/2 mice bearing P815 mastocytoma led to rapid tumor regression (Sun et al., *Immunity* (1996) 4:555-564).

The use of any natural, or artificial, antigen presenting cell (APC) system to generate cytotoxic T lymphocytes in vitro is limited by the antigen specificities these systems are capable of generating.

The following APC systems have been utilized to generate antigen-specific CTL's to single epitopes:
1. Human dendritic cells (DC) pulsed with defined peptides;
2. Peripheral blood mononuclear cells (PBMCs) which have been driven to lymphoblasts and pulsed with peptides;
3. Lymphoblastoid cell lines (LCL) where the natural peptides are acid-stripped and loaded with the peptides of interest;
4. *Drosophila* cells engineered to express empty class I molecules; and Mouse 3T3 cells transfected with human class I and co-stimulatory molecules. (J-B. Latouche and M. Sadelain, *Nature Biotech* (2000) 18:405-409).

Dendritic cells (DCs) are considered the primary antigen presenting cell system in humans because of their wide application in presenting primary antigen cells. Self or foreign proteins are processed within a DC. The resultant peptide epitopes are presented by HLA molecules, and are transported to the surface of the DC. However, it was found that DCs would not consistently generate in vitro, CTLs directed against four different peptides. This would have provided CTLs having activity corresponding to each of the four peptides. In addition, it was also found that the phenotype of the DC at the time of peptide pulsing, mature or immature, did not effect the outcome.

Alternatively, *Drosophila* cell stimulation usually resulted in CTLs directed against up to ten different types of peptides. This provides CTLs that are active to each of the ten peptides.

The ability of *Drosophila* cells and DC to elicit CTL responses were evaluated, initially to a single peptide epitope, following the standard stimulation protocols for each, in order to compare DCs and transfected *Drosophila* cells. Immature DCs were generated by culturing for one week autologous monocytes in the presence of IL-4 and GM-CSF. Mature DCs were obtained from immature DCs by addition of TNF α to the culture medium twenty-four hours prior to harvesting. DCs (immature and mature) were harvested, pulsed with peptides and mixed with purified CD8 cells following the procedure used for the stimulation of CD8 cells and peptide-pulsed *Drosophila* cells. *Drosophila* cells were found to be generally better stimulators than DC. Further, DCs displaying either the immature or mature phenotype were not as efficient as *Drosophila* cells in eliciting specific CTL responses when defined peptides were used to pulse the APCs. This is particularly surprising, because of the dominant role played by DCs in the immune system.

Preparation Of Cytotoxic Lymphocytes

CD8+ cells isolated from leukapheresis samples by positive selection with anti-CD8 antibody are stimulated against IgE and/or CD40L associated peptides presented by *Drosophila* cells expressing Human Class I molecules (HLA-A2.1), B7.1, ICAM-1, LFA-3 and B7.2. CD8+ cells are re-stimulated for two rounds with autologous monocytes loaded with the peptide epitope in the presence of IL-2 and IL-7. CTLs are non-specifically expanded with OKT3 and IL-2. CTL activity is measured against cells and purity of CD8+ T cells is assessed by flow cytometry.

The manufacturing processes and protocols are done according to Good Laboratory Practices and Good Manufacturing Practices. "Good Laboratory Practices" and "Good Manufacturing Practices" are standards of laboratory and manufacturing practices, which are set by United States Food and Drug Administration, and are readily known to those of skill in the art. The CTLs are monitored for identity, viability, CTL activity, sterility, and endotoxin content.

The following examples are intended to illustrate but not limit the present invention.

EXAMPLE 1

Manufacture of Drosophila Antigen-Presenting Cells

The Schneider S2 cell line was prepared from Drosophila melanogaster (Oregon-R) eggs according to published procedures and has been deposited with the American Type Culture Collection (CRL 10974). S2 cells are grown in commercial Schneider's Drosophila medium supplemented with 10% fetal bovine serum.

The pRmHa-3 plasmid vector for expressing MHC Class I and co-stimulatory proteins in S2 cells was derived from the pRmHa-1 expression vector constructed as described in the literature. It contains a metallothionein promoter, metal response consensus sequences and an alcohol dehydrogenase gene bearing a polyadenylation signal isolated from Drosophila melanogaster.

Complementary DNAs for Transfection were Prepared as Follows:

HLA-A2.1 and β-2 microglobulin: Reverse transcription-PCR from K562 cells using primers derived from the published sequence.
B7.1: Reverse transcription-PCR from K562 cells using primers derived from the published sequence.
ICAM-1: Reverse transcription-PCR from K562 cells using primers derived from the published sequence.
B7.2: Reverse transcription-PCR from HL-60 cells (ATCC CCL-240) using primers derived from the published sequence.
LFA-3: Reverse transcription-PCR from HL-60 cells (ATCC CCL-240) using primers derived from the published sequence.

Complementary DNAs were individually inserted into the pRmHa-3 vector. S2 cells were transfected with a mixture of HLA-A2.1, B7.1 and ICAM-1 plasmid DNAs and the phshneo plasmid using the calcium phosphate precipitation method. Stably transfected cells were selected by culturing in Schneider's medium containing geneticin. Twenty-four hours before use, expression of the transfected genes was induced by addition of $CuSO_4$. The level of expression was assessed by flow cytometry using anti-HLA-A2.1, anti-B7.1 and anti-ICAM-1 antibodies. HLA expression by greater than 30% of the cells is necessary for efficient in vitro activation of CD8+ lymphocytes.

Isolation of Human CD8+ Cells

CD8+ cells are isolated from leukapheresis samples by positive selection using the Dynabeads™ isolation procedure (Dynal). An anti-human CD8 mouse monoclonal antibody (50 µg/ml in human gamma globulin [Gammagard®]) is added to washed cells in Dulbecco's PBS supplemented with 1% human serum albumin (Baxter-Hyland) and 0.2% Na citrate. After incubation at 4° C. for forty-five minutes with gentle mixing, the cells are washed and re-suspended in the same buffer containing Dynal magnetic beads (Dynabeads™) coated with sheep anti-mouse IgG at a bead to cell ratio of 1:1. The cells and beads are placed into a sterile tube and gently mixed at 4° C. for forty-five minutes. At the end of this time, the antibody-bound cells are removed magnetically using the MPC-1® separator according to the manufacturer's instructions (Dynal). Dissociation of the CD8 cell-bead complex is achieved by incubation at 37° C. for forty-five minutes in the presence of CD8 peptide$_{59-70}$ (AAEGLDTQRFSG, SEQ.ID.NO.:52). Free beads are removed magnetically and the CD8 cells are counted and analyzed by flow cytometry to evaluate purity. Recovery of CD8+ cells is typically greater than 80%. Table 1 summarizes the cell composition of fourteen separate CD8+ preparations from normal human PBMC preparations by positive selection with anti-CD8 antibody.

TABLE 1

Purification of CD8+ Cells by Positive Selection Analyzed by Flow Cytometry

| CELL TYPE | PBMC | | POST SELECTION | |
| --- | --- | --- | --- | --- |
| | Mean % | (Range) | Mean % | (Range) |
| CD8 T cells | 15% | (7-24) | 82% | (56-95) |
| CD4 T cells | 36% | (14-52) | 2% | (0.1-10) |
| CD 14 Monocytes | 15% | (7-26) | 0.8% | (0.2-2) |
| CD15 Neutrophils | 12% | (8-21) | 0.6% | (0.1-3) |
| CD19 B cells | 2% | (0.4-7) | 3% | (0.5-9) |
| CD56 NK cells | 6% | (2-17) | 6% | (0.1-20) |

In Vitro Immunization of Purified Human CD8+ Cells

Primary Stimulation Transfected Drosophila S2 cells are incubated in Schneider's medium ($10^6$ cells/ml) supplemented with 10% fetal calf serum and $CuSO_4$ at 27° C. for twenty-four hours. Cells are harvested, washed and re-suspended in Insect X-press medium (BioWhittaker) containing 100 µg/ml human tyrosinase$_{369-377}$ (RWJPRI). Following incubation at 27° C. for three hours, the S2 cells are mixed with CD8+ cells at a ratio of 1:10 in RPMI medium (Gibco) supplemented with 10% autologous serum. The cell mixture is incubated for four days at 37° C. during which the Drosophila cells die off. On Day 5, IL-2 (20 U/ml) and IL-7 (30 U/ml) are added with a media change to selectively expand the tyrosinase-specific CTL population.

Re-stimulation: Frozen, autologous, CD8-depleted PBMCs, obtained at the time of leukapheresis, are thawed, washed and re-suspended at $10^6$ cells/ml in RPMI medium containing 10% autologous serum (as a source of β2 microglobulin) and 20 µg/ml of peptide epitope. Following γ-irradiation (5,000 rads), the cells are incubated at 37° C. for two hours.

Non-adherent cells are removed by washing with Dulbecco's PBS. Adherent monocytes are loaded with the tyrosinase epitope by incubation for 90 minutes in Hepes-buffered RPMI medium containing 10% autologous serum and 10 µg/ml of peptide epitope. The supernatant is removed and the Drosophila-activated CD8+ cell suspension ($3 \times 10^6$ cells/ml in RPMI medium with 10% autologous serum) is added at a ratio of ten CD8+ cells to one adherent monocyte. After three to four days of culture at 37° C., IL-2 (20 U/ml) and IL-7 (30 U/ml) are added with a medium change to selectively expand the epitope-specific CTL population.

Non-specific Expansion: CD8's non-specifically expanded and culturing them in RPMI medium supplemented with autologous serum, anti-CD3 monoclonal antibody (OKT®3), IL-2 and γ irradiated autologous PBMCs.

Assays for Activity and Purity

CTL Assay: Epitope-bearing (target) cells are used as target cells in a $^{51}$Cr release assay. 5×10$^6$ target cells in RPMI medium containing 4% fetal calf serum, 1% HEPES buffer and 0.25% gentamycin are labeled at 37° C. for one hour with 0.1 mCi $^{51}$Cr. Cells are washed four times and diluted to 10$^5$ cells/ml in RPMI with 10% fetal bovine serum (HyClone). In a 96-well microtiter plate, 100 µl effector CTLs and 100 µl peptide-loaded, $^{51}$Cr-labeled target cells are combined at ratios of 100:1, 20:1 and 4:1 (effector:target). K562 cells are added at a ratio of 20:1 (K562) to reduce natural killer cell background lysis. Non-specific lysis is assessed using cells labeled with $^{51}$Cr as described above, but not bearing the epitope cell line. Controls to measure spontaneous release and maximum release of $^{51}$Cr are included in duplicate. After incubation at 37° C. for six hours, the plates are centrifuged and the supernatants counted to measure $^{51}$Cr release. Percent specific lysis is calculated using the following equation:

$$\frac{cpm \text{ sample} - cpm \text{ spontaneous release}}{cpm \text{ maximum release} - cpm \text{ spontaneous release}} \times 100$$

Flow Cytometry: CD8$^+$ cells, before and after in vitro activation, were analyzed for a number of cell surface markers using fluorescent monoclonal antibodies and FACS analysis. Results from a typical activation protocol using cells from a healthy donor is shown in Table 2.

TABLE 2

Flow Cytometry Analysis of In Vitro Activated CD8$^+$ Cells

| MARKER/CELL TYPE | PRE-ACTIVATION Mean % | POST-ACTIVATION Mean % |
| --- | --- | --- |
| CD8 T cell | 98 | 99 |
| TCRαβ T cell receptor | 98 | 92 |
| CD 44 lymph node homing receptor | 91 | 99 |
| CD45RO memory T cell | 58 | 88 |
| CD45RA | 41 | 31 |
| CD62L HEV homing receptor | 24 | 38 |
| CD56 NK cell | 1 | 11 |
| CD25 activated T cell | 0.1 | 29 |

In addition to activity and purity, CTL preparations will be assayed for sterility and endotoxin content.

Reagents

| REAGENT | SUPPLIER | GRADE | NOTES |
| --- | --- | --- | --- |
| Rh IL-2 | Chiron | USP | sterile solution |
| Rh IL-7 | Genzyme | Research | lyophilized, sterile solution |
| Peptide | RWJPRI | Research | |
| Dynabeads ® M-450 | Dynal | GMP | sheep anti-mouse IgG magnetic beads |
| Human serum albumin | Baxter | USP | sterile, non-pyrogenic hepatitis virus-free, 25% solution |
| Fetal bovine serum | Gemini | Research | sterile, BSE-, endotoxin-mycoplasma-free |
| Gammagard ® | Baxter | USP | sterile, human immune globulin solution for injection |
| Anti-CD8 antibody | RWJPRI | Research | mouse anti-human CD8 monoclonal antibody |
| CD8 peptide$_{59-70}$ | RWJPRI | Research | release of CD8$^+$ cells from magnetic beads |
| W6/32 | ATCC | Research | mouse anti-human HLA-A, B, C monoclonal antibody |

Cell Lines

| CELL LINE | SUPPLIER | NOTES |
| --- | --- | --- |
| Drosophila S2 | ATCC | CRL 10974 |
| M14 | UCSD | HLA-A2.1 human melanoma |
| K562 | ATCC | Human erythroleukemic cell line; target for NK cells |
| JY cells | ATCC | EBV-transformed, human B cell line expressing HLA-A2.1 and B7 |
| P815 and P1024 | ATCC | DBA/2 mouse mastocytoma cell lines |
| Jurkat A2.1 | ATCC | acute T cell leukemia transfected with human HLA-A2.1 |

ATCC: American Type Culture Collection

EXAMPLE 2

Trial of Cytotoxic T Cell Infusions Against IgE Producing Cells

Purpose of Trial

This example teaches the effectiveness of cytotoxic T Cell infusions in the treatment of allergic diseases as assessed according to the following factors:

1. Safety and toleration of re-infused autologous CTLs after in vitro immunization;
2. Kinetics of infused CTLs in the systemic circulation factoring in limiting dilution analysis;
3. Whole body disposition of CTLs by radioscintigraphy;
4. Cell composition of biopsied nodules by immunohistology (CTLs, TH, NK, B cells); and
5. Regression of measurable lesions and duration of response over two months.

Treatment with Ex Vivo Generated Autologous CTLs

All patients will receive, at least, a single infusion of autologous CTLs. The number of cycles and the dose of cells administered to each patient are summarized in Table 1. The number of cells generated in vitro is dependent on patient-related factors such as the numbers of PBMCs isolated from the aphaeresis procedure and the number of CD8$^+$ T cells present in each PBMC preparation. Since all of the cells generated in vitro are re-infused into the donor, doses administered to each patient are necessarily varied. In an attempt to normalize the doses between patients, a calculated "potency" score is recorded for each dose. The value is obtained by multiplying the total number of cells by the lytic activity obtained with peptide-loaded target cells. Patients are entered into a second, third or fourth cycle of treatment based on their clinical status at the end of each cycle. The total number of naïve CD8⁺ T cells isolated is dependent on its percentage in each of the PBMC preparations. The percent of CD8⁺ T cells varies among the patients. The procedure for generating CTLs ex vivo is taught in the Specification and Example 1, above.

Up-Regulation of Class I and Melanoma-Associated Antigens in Response to IFNα-2b In an attempt to enhance the ability of the antigen-specific CTLs to lyse IgE producing cells in vivo, low dose IFNα-2b is administered for five consecutive days prior to the CTL infusion, and thrice weekly for an additional four weeks. One way to measure an in vivo response to the cytokine is to evaluate biopsies obtained at serial time points by immunohistochemical analysis for positive staining with specific antibodies.

Antigenic Specificity of Ex Vivo-Generated CTLs

CTLs generated from all patients are evaluated on the day of release against peptide-loaded T2 targets, an HLA-A2 IgE producing M-14 clone 4 cell line and an autologous M-14 cell line, if biopsy material was available to establish a line. Each prepared dose of cells is evaluated for its cytolytic activity. Peptide-loaded T2 cells, presenting either each peptide alone, or all peptides simultaneously, are used to determine the specificity of the CTL response generated for each patient. The ability to lyse endogenously-expressed, HLA-A2-associated, antigen-bearing cells is assessed with an HLA-A2 matched line or an autologous cell line. In addition to cytolytic activity, antigen-specificity is evaluated with an established method for detecting intracellular gamma interferon production, made in response to a specific peptide stimulus. The CTLs generated at the end of the ex vivo protocol are evaluated by this method. The percent of cells specific for each of the peptides is recorded individually. The total number of specific cells in each bulk CD8 culture from a patient is calculated by adding each of the peptide specificities detected in that population of T cells. An increase in the total number of specific cells is detected with each successive treatment cycle.

Presence of Anergic State Did Not Preclude Ability to Generate CTLs or Prevent a Clinical Response Most of the patients treated under this protocol receive previous medical intervention. A pretreatment skin test is performed to determine if an anergic response to a panel of seven common antigens correlates with either an inability to generate CTLs ex vivo, or prevent a documented clinical response. The ability to generate CTLs ex vivo does not correlate with the patient's pretreatment skin test results.

EXAMPLE 3

IgE plays an essential role in the pathogenesis of allergic asthma. Here, we show that cytotoxic T lymphocytes (CTLs) specific for antigenic peptides derived from IgE molecule can be generated in vitro by stimulating resting naive CD8 T cells with IgE peptides presented by artificial antigen presenting cells. The IgE specific CTLs lyse the target cells loaded with IgE peptides in vitro and inhibit antigen specific IgE response in vivo. In addition, adoptive transfer of the IgE specific CTL to an asthmatic mouse model can inhibit the development of lung inflammation and airway hypersensitivity. Thus, IgE specific CTL may provide a treatment for allergic asthma and other IgE-mediated allergic diseases.

Cytotoxic T lymphocytes are derived from resting naïve CD8 T cells. In the present of antigens and co-stimulations, resting naïve CD8 T cells can be activated and differentiated into armed cytotoxic T cells, which can destroy the target cells that express the antigens.

CTLs play an essential role in immunity against virus and intracellular pathogens by lysis the infected cells and/or through the effect of cytokines CTL produced.

Identification of Antigenic Peptides from IgE Protein Sequence:

Two alleles of mouse IgE (IgE$^a$ and IgE$^b$) have been described previously (P06336). The alignment of the amino acid sequences of the IgE$^a$ and IgE$^b$ shown that 95% of the amino acid sequences are identical. A fourteen amino acids differences are located at the junction region between CH1 and CH2 region and another five amino acid differences are located at the junction region between the CH3 and CH4 region. The amino acid sequence of IgE$^b$ was analyzed for 9 mer peptide sequences that contain binding motifs for L$^d$ and D$^b$ MHC class I molecules by using the software of the Bioinformatics & Molecular Analysis Section available at http://bimas.dcrt.nih.gov/molbio/hla_bind/. This program ranks potential nonapeptides based on a predicted half-time of dissociation to MHC class I molecules. Based on the ranking analysis, eight peptides with L$^d$ binding motifs and five peptides with D$^b$ binding motifs were selected for synthesis (Table 1).

The binding capacity of these synthetic peptides to L$^d$ and D$^b$ class I molecules were tested in an MHC class I stabilization assay (Cai et al. (1996) supra). Antigen-transporting deficient (TAP⁻) RMAS cells (H-2$^b$) or L$^d$ transfected RMAS (RMAS-L$^d$) cells were cultured in the presence of a titrated concentration of peptides at 27° C. After overnight culturing at 27° C., these cells were further cultured for two hours at 37° C. and the surface expression of L$^d$ or D$^b$ on the cells were analyzed by flow cytometry. As shown in Table 1, two IgE peptides, IgE 11 and IgE366 bind to L$^d$ strongly, whereas IgE 114 binds L$^d$ weakly. Of the five peptides predicted bind to D$^b$, only IgE44 binds D$^b$ strongly and two peptides, IgE16 and IgE125, bind D$^b$ weakly. Interestingly, IgE366 originally predicted binding L$^d$ binds both L$^d$ and D$^b$. Thus, a total of six peptides were identified that bind to either L$^d$ or D$^b$ MHC class I molecules.

TABLE 1

Mouse IgE$^a$ amino acid sequence: SEQ ID NO: 14

```
  1 sirnpqlypl kpckgtasmt lgclvkdyep npvtvtwysd
    slnmstvnfp 51 algselkvtt sqvtswgksa knftchvthp psfnesrtil
    vrpvnitept 101 lellhsscdp nafhstiqly cfiyghilnd vsvswlmddr
    eitdtlaqtv 151 likeegklas tcsklniteq qwmsestftc kvtsqgvdyl
    ahtrrcpdhe 201 prgvitylip pspldlyqng apkltclvvd leseknvnvt
    wnqekktsvs 251 asqwytkhhn nattsitsil pvvakdwieg ygyqcivdhp
    dfpkpivrsi 301 tktpgqrsap evyvfpppee esedkrtltc liqnffpedi
    svqwlgdgkl 351 isnsqhsttt plksngsnqg ffifsrleva ktlwtqrkqf
    tcqvihealq 401 kprklektis tslgntslpr s
```

TABLE 1

Identification of Antigenic Peptides of Mouse IgE

| Peptide name | MHC Selected | Peptide sequence | Sequence Identification Number | Score[a] | Stabilization of MHC[b] |
|---|---|---|---|---|---|
| IgE 11  | $L^d$ | KPCKGTASM | SEQ ID NO: 1  | 195 | ++ |
| IgE 209 | $L^d$ | IPPSPLDLY | SEQ ID NO: 2  | 90  | − |
| IgE 366 | $L^d$ | GSNQGFFIF | SEQ ID NO: 3  | 65  | ++[c] |
| IgE 29  | $L^d$ | FPNPVTVTW | SEQ ID NO: 4  | 60  | − |
| IgE 105 | $L^d$ | HSSCDPNAF | SEQ ID NO: 5  | 50  | − |
| IgE 114 | $L^d$ | HSTIQLYCF | SEQ ID NO: 6  | 50  | + |
| IgE 363 | $L^d$ | KSNGSNQGF | SEQ ID NO: 7  | 50  | − |
| IgE 307 | $L^d$ | RSAFEVYVF | SEQ ID NO: 8  | 50  | − |
| IgE 44  | $D^b$ | MSTVNFPAL | SEQ ID NO: 9  | 937 | ++ |
| IgE 411 | $D^b$ | TSLGNTSLR | SEQ ID NO: 10 | 44  | − |
| IgE 16  | $D^b$ | TASMTLGCL | SEQ ID NO: 11 | 22  | + |
| IgE 159 | $D^b$ | ASTCSKLNI | SEQ ID NO: 12 | 19  | − |
| IgE 125 | $D^b$ | GHILNDVSV | SEQ ID NO: 13 | 30  | + |

[a]Calculated score in arbitrary units.
[b]The ratio of fluorescence intensity with peptides − without peptide/without peptides less than two-fold is scored as "+" and more than two fold is calculate as "++".
[c]IgE 366 also stabilizes $D^b$ class I molecules.

Generation of IgE Peptide Specific CTLs In Vitro

The ability of these IgE peptides in eliciting CTL responses was evaluated in vitro. As previously described, *Drosophila* cells transfected with MHC class I plus B7-1 and ICAM-1 are potent antigen presenting cells (APC) in activation of resting naïve CD8 T cells in vitro. Resting naïve CD8 T cells were purified from mouse lymph nodes and cultured with peptide loaded *Drosophila* cells transfected with $L^d$ or $D^b$ plus B7-1 and ICAM-1 in the absence of cytokines. IL-2 (20 units/ml) was added at Day 3 and every other day thereafter. The CTL activity towards peptides loaded RMAS ($K^b$, $D^b$) cells or RMAS-$L^d$ cells were measured on Day 9. As shown in FIG. 1, CTLs induced by IgE 44 peptide specifically lysed the RMAS cells loaded with IgE 44 peptides, neither the target cells alone nor the target cells loaded with other IgE peptides were recognized by the IgE44 specific CTLs.

No specific CTL activity was induced by IgE 16 or IgE 125 peptides, which have been show to bind $D^b$. IgE366 was originally identified as $L^d$ binding peptide, interestingly, in addition to inducing $L^d$ restricted CTLs by IgE366, IgE366 also induce $D^b$ restricted CTLs (FIG. 2, Panel B). Of the three $L^d$ binding peptides, in addition to IgE366, IgE11 also induces antigen specific CTLs. The killing of IgE specific CTL is poreforin dependent and is independent of the expression of IFNγ (FIG. 2, Panel C). Moreover, the CTL induced by IgE peptides are MHC restricted because the killing of IgE44 loaded RMAS targets by IgE44 specific CTL was completely blocked by anti-$D^b$ mAb (FIG. 2, Panel D). FACS analysis of these CTL revealed that they are αβ TCR positive CD8⁺ T cells and no expression of NK cell marker (DX5 or NK1.1) were detected on these cells (data not shown).

Inhibition of IgE Responses by Anti-IgE Specific CTLs.

Because CTLs induced by IgE peptides kills the target cell specifically in vitro, we were interested in seeing if these CTLs could inhibit the IgE responses in vivo. Mice have very low serum IgE and do not develop allergic response spontaneously. Ovalbumin precipitated with Alum Hydroxyde has been used to induce antigen specific IgE responses in mice. As shown in FIG. 3, after two immunizations with OVA plus alum hydroxyde, both total serum IgE and ova-specific IgE in the immunized mice were high and the IgE level was further increased after intranasal challenge of these mice with OVA.

TABLE 2

The Effect of Anti-IgE CTL on Airway Inflammation[a]

| Treatment | Inflammation[b] | Eosinophilic infiltration | Hyperplasia of BALT[c] |
|---|---|---|---|
| PBS (5)          | 3, 1, 2, 2, 0 | 2, 0, 2, 3, 0 | 2, 0, 2, 3, 0 |
| Anti-IgE CTL (5) | 0, 0, 0, 1, 0 | 0, 0, 0, 0, 0 | 0, T, 0, 1, 0 |
| Control CTL (4)  | 3, 3, 2, 3    | 2, 3, 3, 1    | 3, 2, 2, 2    |
| Normal mice (4)  | 0, 0, 0, 0    | 0, 0, 0, 0    | 0, 0, 0, 0    |

[a]Adult CBF1/J mice were immunized with 50 μg ovalbumin (OVA) plus Alum hydroxide intraperitoneally on Day 1 and Day 14. Two weeks after the second immunization, 5 × 10⁶ anti-IgE CTL or a control CTL or PBS were given every other day for three times. Three weeks after the last CTL treatment, the mice were challenged with OVA intranasally every other day for three times. One day after the last challenge, bronchial alveolar lavage was collected and lung tissue was collected from each mice and stained with HE staining. The lung inflammation of each mouse was independently evaluated by a pathologist.
[b]Score: O = Normal; T = trace; 1 = mild; 2 = mild to moderated; 3 = moderate; 4 = severe
[c]BALT = Bronchial Associated Lymphoid Hyperplasia.

TABLE 3

HLA-A2 Peptide Motif Search for Human IgE

| Rank | Start Position | Subsequence Residue Listing | Score (Estimate Half Time of Disassociation of HLA-2 Containing this Subsequence) |
|---|---|---|---|
| 1  | 185 | WLSDRTYTC | 93.696 |
| 2  | 96  | WVDNKTFSV | 64.948 |
| 3  | 71  | LLTVSGAWA | 46.451 |
| 4  | 365 | QLPDARHST | 30.553 |
| 5  | 3   | TQSPSVFPL | 28.893 |
| 6  | 309 | ALMRSTTKT | 27.572 |
| 7  | 59  | TLTLSGHYA | 27.324 |
| 8  | 54  | TLPATTLTL | 21.362 |
| 9  | 47  | SLNGTTMTL | 21.362 |
| 10 | 61  | TLSGHYATI | 15.649 |
| 11 | 52  | TMTLPATTL | 15.428 |
| 12 | 178 | LTLSQKHWL | 10.264 |

TABLE 3-continued

HLA-A2 Peptide Motif Search for Human IgE

| Rank | Start Position | Subsequence Residue Listing | Score (Estimate Half Time of Disassociation of HLA-2 Containing this Subsequence) |
|---|---|---|---|
| 13 | 66 | YATISLLTV | 10.220 |
| 14 | 154 | QVMDVDLST | 9.892 |
| 15 | 17 | NIPSNATSV | 9.563 |
| 16 | 133 | LLCLVSGYT | 9.058 |
| 17 | 403 | FICRAVHEA | 7.227 |
| 18 | 236 | TITCLVVDL | 6.756 |
| 19 | 356 | SVQWLHNEV | 6.086 |
| 20 | 155 | VMDVDLSTA | 5.612 |

TABLE 4

HLA-A2 Peptide Motif Search for Human IgE by Neuro-Network

| Net Output | C150 | Start | End | Sequence |
|---|---|---|---|---|
| 0.747555 | 5.71921 | 223 | 231 | RPSPFDLFI |
| 0.695169 | 8.21283 | 349 | 357 | NFMPEDISV |
| 0.628452 | 13.021 | 358 | 366 | QWLHNEVQL |
| 0.60628 | 15.1782 | 33 | 41 | QYFPEPVMV |
| 0.53619 | 24.6281 | 54 | 62 | TLPATTLT |
| 0.45981 | 41.7417 | 108 | 116 | DFTPPTVKI |
| 0.406526 | 60.3147 | 229 | 237 | LFIRKSPTI |
| 0.382602 | 71.153 | 96 | 104 | WVDNKTFSV |
| 0.373791 | 75.6184 | 148 | 156 | TWLEDGQVM |
| 0.34985 | 89.2174 | 61 | 69 | TLSGHYATI |
| 0.348214 | 90.2317 | 396 | 404 | EWEQKDEFI |
| 0.344683 | 92.4594 | 278 | 286 | LTVTSTLPV |
| 0.317372 | 111.656 | 128 | 136 | PPTIQLLCL |
| 0.29653 | 128.947 | 170 | 178 | ELASTQSEL |
| 0.292132 | 132.924 | 236 | 244 | TITCLVVDL |
| 0.272911 | 151.798 | 106 | 114 | SRDFTPPTV |
| 0.26747 | 157.612 | 213 | 221 | NPRGVSAYL |
| 0.252711 | 174.529 | 10 | 18 | PLTRCCKNI |
| 0.227935 | 207.107 | 147 | 155 | ITWLEDGQV |
| 0.220931 | 217.374 | 234 | 242 | SPTITCLVV |
| 0.219179 | 220.02 | 47 | 55 | SLNGTTMTL |
| 0.218951 | 220.368 | 384 | 392 | FFVFSRLEV |
| 0.199355 | 252.309 | 139 | 147 | GYTPGTINI |
| 0.188573 | 271.82 | 123 | 131 | GGGHFPPTI |
| 0.170795 | 307.296 | 245 | 253 | APSKGTVNL |
| 0.136633 | 389.134 | 302 | 310 | THPHLPRAL |
| 0.124225 | 423.96 | 284 | 292 | LPVGTRDWI |
| 0.115665 | 449.785 | 378 | 386 | KTKGSGFFV |

EXAMPLE 4

In the presence of specific antigen and constimulation, resting CD8 T cells can be activated and differentiated into CTL, which plays an essential role in anti-virus immune response. Recently, it has also been shown that tumor associated antigens specific CTL generated in vitro can be used in treating cancer patients. Here we show that antigenic peptides identified from non-tumor self-antigens can induce specific cytotoxic T lymphocyte (CTL) in vitro. The CTL induced by peptides identified from CD40L, a self antigen transiently expressed on activated CD4 T cells, can kill activated CD4 T cells and the killing can be blocked either by the antibody (Ab) specific for the restricting class I molecule or by the Ab recognizing CD8 molecule. In addition, neither activated CD4 T cells generated from CD40L$^{-/-}$ mice nor from 2 m$^{-/-}$ mice are killed by the CD40L specific CTL, demonstrating that the killing of activated CD4 T cells by CD40L specific CTL is antigen-dependent and MHC restricted. Importantly, in vitro generated CTL specific for CD40L inhibit CD4-dependent antibody responses of all isotypes in vivo. In contrast, CTL induced by antigenic peptides derived from IgE specifically inhibit IgE responses and adoptive transfer of CD40L-specific CU to NOD mice at early age delay the development of diabetes in NOD mice. Thus, in vitro generated CTL specific for non-tumor self-antigens expressed on activated CD4 T cells can regulate immune responses in vivo.

Allergic diseases, such as hay fever, asthma and systemic anaphylaxis, are immune responses to innocuous substances. The hallmark of the diseases is activation of CD4 cells and over production of IgE by B cells. The current therapies have been focused on the treatment of symptoms and do not prevent the development and progression of the diseases. Because allergen-activated CD4 cells and IgE producing B cells play a central role in the pathogenesis of allergy, our strategy is to use autologous CTL to eliminate activated CD4 T cells and IgE producing B cells, thus preventing the development and progression of the diseases. Two molecules, CD40 ligand (CD40L) and IgE, were selected as target antigens for CU therapy. Three antigenic peptides from CD40L and two antigenic peptides from IgE were identified. CTLs specific for these peptides have been generated and the function of these CTLs has been evaluated both in vitro and in vivo.

Three antigenic epitopes from CD40L and two epitopes from IgE molecules were identified. Synthetic peptides of the antigenic epitopes were able to bind to class I molecules and to activate resting naive CD8 T cells in vitro.

CTLs were generated by stimulation of CD8 T cells with CD40L or IgE peptides presented by *Drosophila* cells expressing MHC class I, B7-1 and ICAM-1 molecules. The CTLs thus generated in vitro killed peptide-loaded target cells specifically. CD40L-peptide specific CTL killed activated CD4 T cells and the recognition was dependent on the expression of CD40L and MHC class I molecules.

The function of CD40L-specific CTL were also evaluated in vivo. Antigen-specific antibody response was inhibited by anti-CD40L CTL. The effect of anti-CD40L CTL and anti-IgE CTL on allergy and autoimmune diseases will be investigated in animal models.

TABLE 5

MCH Class I Binding Motif Search for Mouse CD40L

| Rank | Start Position | AA Sequence | Sequence Identification Number | Score Number |
|---|---|---|---|---|
| 1 | 17 | LPASMKIFM | SEQ ID NO: 15 | 150.00 ($L^d$) |
| 2 | 186 | RPFIVGLWL | SEQ ID NO: 16 | 150.00 ($L^d$) |
| 3 | 118 | DPQIAAHVV | SEQ ID NO: 17 | 90.00 ($L^d$) |
| 4 | 220 | QSVHLGGVF | SEQ ID NO: 18 | 50.00 ($L^d$) |
| 5 | 9 | SPRSVATGL | SEQ ID NO: 19 | 45.00 ($L^d$) |
| 6 | 195 | KPSIGSERI | SEQ ID NO: 20 | 39.00 ($L^d$) |

TABLE 5-continued

MCH Class I Binding Motif Search for Mouse CD40L

| Rank | Start Position | AA Sequence | Sequence Identification Number | Score Number |
|---|---|---|---|---|
| 7 | 252 | FSSFGLLKL | SEQ ID NO: 21 | 32.50 ($L^d$) |
| 8 | 7 | QPSPRSVAT | SEQ ID NO: 22 | 30.00 ($L^d$) |
| 9 | 181 | EPSSQRPFI | SEQ ID NO: 23 | 30.00 ($L^d$) |
| 10 | 79 | LSLLNCEEM | SEQ ID NO: 24 | 25.00 ($L^d$) |
| 1 | 79 | LSLLNCEEM | SEQ ID NO: 24 | 5713.03 ($D^b$) |
| 2 | 152 | VMLENGKQL | SEQ ID NO: 25 | 5160.15 ($D^b$) |
| 3 | 146 | TMKSNLVML | SEQ ID NO: 26 | 2648.88 ($D^b$) |
| 4 | 235 | SVFVNVTEA | SEQ ID NO: 27 | 95.12 ($D^b$) |
| 5 | 38 | GSVLFAVYL | SEQ ID NO: 28 | 46.87 ($D^b$) |
| 6 | 19 | ASMKIFMYL | SEQ ID NO: 29 | 46.87 ($D^b$) |

Estimate of half time of disassociation of a molecule containing this subsequence.

TABLE 6

| Rank | Start Position | Subsequence Residue Listing | Sequence Identification Number | Score (Estimate of Half-Time of Disassociation of a Molecule Containing this Subsequence) |
|---|---|---|---|---|
| 1 | 24 | FMYLLTVFL | SEQ ID NO: 30 | 1249.083 |
| 2 | 167 | GLYYIYAQV | SEQ ID NO: 31 | 333.850 |
| 3 | 22 | KIFMYLLTV | SEQ ID NO: 32 | 284.846 |
| 4 | 36 | MIGSALFAV | SEQ ID NO: 33 | 216.879 |
| 5 | 58 | NLHEDFVFM | SEQ ID NO: 34 | 212.854 |
| 6 | 170 | YIYAQVTFC | SEQ ID NO: 35 | 127.199 |
| 7 | 26 | YLLTVFLIT | SEQ ID NO: 36 | 98.803 |
| 8 | 231 | LQPGASVFV | SEQ ID NO: 37 | 65.934 |
| 9 | 45 | YLHRRLDKI | SEQ ID NO: 38 | 54.086 |
| 10 | 147 | TMSNNLVTL | SEQ ID NO: 39 | 35.485 |
| 11 | 229 | FELQPGASV | SEQ ID NO: 40 | 23.018 |
| 12 | 160 | QLTVKRQGL | SEQ ID NO: 41 | 21.362 |
| 13 | 35 | QMIGSALFA | SEQ ID NO: 42 | 19.734 |
| 14 | 185 | SQAPFIASL | SEQ ID NO: 43 | 18.930 |
| 15 | 19 | ISMKIFMYL | SEQ ID NO: 44 | 9.166 |
| 16 | 153 | VTLENGKQL | SEQ ID NO: 45 | 7.652 |

TABLE 6-continued

| Rank | Start Position | Subsequence Residue Listing | Sequence Identification Number | Score (Estimate of Half-Time of Disassociation of a Molecule Containing this Subsequence) |
|---|---|---|---|---|
| 17 | 126 | VISEASSKT | SEQ ID NO: 46 | 7.142 |
| 18 | 227 | FVFELQPGA | SEQ ID NO: 47 | 6.594 |
| 19 | 20 | SMKIFMYLL | SEQ ID NO: 48 | 4.720 |
| 20 | 165 | RQGLYYIYA | SEQ ID NO: 49 | 4.156 |

TABLE 7

Summary of CTL Activity Generated From PBMC in Different Donors

| IgE Peptide | AA Sequence | Sequence Identification Number | Specific Killing* |
|---|---|---|---|
| 47 | SLNGTTMTL[1] | SEQ ID NO: 50 | 7/8 |
| 96 | WVDNKTFSV[1] | SEQ ID NO: 51 | 3/8 |
| 185 | WLSDRTYTC | SEQ ID NO: 52 | 0/8 |
| 308 | ALSDRTYTC | SEQ ID NO: 53 | 0/3 |
| 876 | SLLTVSGAWA | SEQ ID NO: 54 | 0/5 |
| 883 | WLEDGQVMDV | SEQ ID NO: 55 | 1/5 |
| 884 | TLTVTSTLPV[2] | SEQ ID NO: 56 | 8/8 |
| 887 | QMFTCRVAHT | SEQ ID NO: 57 | 1/4 |
| 890 | YATISLLTV1 | SEQ ID NO: 58 | 4/5 |
| 895 | TLACLIQNFM[2] | SEQ ID NO: 59 | 3/4 |
| 898 | QVMDVDLSTA[2] | SEQ ID NO: 60 | 3/4 | x/N x: number of donor from whom anti-IgE CTL was generated; N: number of donor tested CD8+ T cells were purified from PBMC and cultured with Drosophila cells transfected with A2.1, B7.1 and ICAM-1 in the presence of IgE peptides. Statistics indicated the capability of IgE peptide to generate specific CTL response from different donors. [1] and [2] indicate anti-IgE CTL was generated from 9-mer and 10-mer respectively.

What is claimed is:

1. A non-naturally occurring antigen-presenting cell derived from *Drosophila melanogaster* comprising cell surface MHC class I and at least one antigenic peptide from human CD40L wherein the antigen presenting cell is capable of activating CD8+ cells and wherein at least one human CD40L peptide is selected from the group consisting of: FELQPGASV (SEQ ID NO: 40~), QLTVKRQRL (SEQ ID NO: 41), QMIGSALFA (SEQ ID NO: 42), SQAPFIASL (SEQ ID NO: 43), ISMKIFMYL (SEQ ID NO: 44), VTLENGKQLL (SEQ ID NO: 45), VISEASSKT (SEQ ID NO: 46), GVFELQPGA (SEQ ID NO: 47), SMKIFMYLL (SEQ ID NO: 48), and RQGLYYIYA (SEQ ID NO: 49).

* * * * *